US008110365B2

(12) United States Patent
Dworkin et al.

(10) Patent No.: US 8,110,365 B2
(45) Date of Patent: Feb. 7, 2012

(54) COMPOSITIONS AND METHODS FOR DETECTING AND TREATING RENAL INJURY AND INFLAMMATION

(75) Inventors: Lance Dworkin, Providence, RI (US); Rujun Gong, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 1347 days.

(21) Appl. No.: 11/731,250

(22) Filed: Mar. 29, 2007

(65) Prior Publication Data

US 2008/0085324 A1   Apr. 10, 2008

Related U.S. Application Data

(60) Provisional application No. 60/828,378, filed on Oct. 5, 2006.

(51) Int. Cl.
*G01N 31/00* (2006.01)
*G01N 33/53* (2006.01)

(52) U.S. Cl. .......... 435/7.1; 435/4; 435/287.9; 436/501; 436/518; 436/525; 436/529; 436/535; 436/809; 427/287; 427/337; 427/338; 422/50; 530/300; 530/350

(58) Field of Classification Search .................. None
See application file for complete search history.

(56) References Cited

U.S. PATENT DOCUMENTS

| 2005/0074812 A1 | 4/2005 | Ruoslahti et al. |
| 2005/0153337 A1 | 7/2005 | Manoharan |

FOREIGN PATENT DOCUMENTS

WO   WO02/24941   3/2002

OTHER PUBLICATIONS

Aleksandrov and Speranskaia, Time course of carrageenin inflammation under treatment with lithium hydroxybutyrate, Biull Eksp Biol Med 106:233-5 (1988).
Ali et al., Glycogen synthase kinase-3: properties, functions, and regulation. Chem. Rev. 101:2527-40 (2001).
Austen, The role of arachidonic acid metabolites in local and systemic inflammatory processes. Drugs 33(1):10-7 (1987).
Bohle et al., The long-term prognosis of the primary glomerulonephritides. A morphological and clinical analysis of 1747 cases. Pathol. Res. Pract. 188:908-24 (1992).
Buss et al. Phosphorylation of serine 468 by GSK-3β negatively regulates basal p65 NF-κB activity. J. Biol. Chem. 279:49571-4 (2004).
Cao and Cooper, Role of angiotensin II in tubulointerstitial injury. Semin. Nephrol. 21:554-62 (2001).
Cho and Johnson, Primed phosphorylation of tau at Thr231 by glycogen synthase kinase 3β (GSK3β) plays a critical role in regulating tau's ability to bind and stabilize microtubules. J. Neurochem. 88:349-58 (2004).

Cohen and Frame, The renaissance of GSK3. Nat. Rev. Mol. Cell. Biol. 2:769-76 (2001).
Cohen and Goedert, GSK3 inhibitors: development and therapeutic potential. Nat. Rev. Drug Discov. 3:479-87 (2004).
Daha and vanKooten, Is the proximal tubular cell a proinflammatory cell? Nephron. Exp. Nephrol. 15:41-43 (2000).
de Haij et al., Mechanism of steroid action in renal epithelial cells. Kidney Int. 65:1577-88 (2004).
Demarchi et al., Glycogen synthase kinase-3β regulates NF-κB1/p105 stability. J. Biol. Chem. 278:39583-90 (2003).
Deng et al., Crossregulation of NF-κB by the APC/GSK-3β/β-catenin pathway. Mol. Carcinog. 39:139-46 (2004).
Doble and Woodgett, GSK-3: tricks of the trade for a multi-tasking kinase. J. Cell. Sci. 116:1175-86 (2003).
Dugo et al., Glycogen synthase kinase-3beta inhibitors protect against the organ injury and dysfunction caused by hemorrhage and resuscitation. Shock 25:485-91 (2006).
Dugo et al., GSK-3β inhibitors attenuate the organ injury/dysfunction caused by endotoxemia in the rat. Crit. Care Med. 33:1903-12 (2005).
Dworkin et al., Hepatocyte growth factor ameliorates progression of interstitial fibrosis in rats with established renal injury. Kidney Int. 65:409-19 (2004).
Eddy, Molecular basis of renal fibrosis. Pediatr. Nephrol. 15:290-301 (2000).
Eddy, Proteinuria and interstitial injury. Nephrol. Dial. Transplant 19:277-81 (2004).
Fink, What do insulin, estrogen, valproic acid, and TDZD-8 have in common? Crit Care Med 33:2115-7 (2005).
Fujihara et al., Mycophenolate mofetil attenuates renal injury in the rat remnant kidney. Kidney Int. 54:1510-9 (1998).
Gitlin, Lithium and the kidney: an updated review. Drug Safety 20:231-43 (1999).
Gomez-Garre et al., Activation of NF-κB in tubular epithelial cells of rats with intense proteinuria: role of angiotensin II and endothelin-1. Hypertension 37:1171-8 (2001).
Gong et al., Activation of PI3K-Akt-GSK3β pathway mediates hepatocyte growth factor inhibition of RANTES expression in renal tubular epithelial cells. Biochem. Biophys. Res. Commun. 330:27-33 (2005).
Gong et al., Hepatocyte growth factor (HGF) suppresses acute renal inflammation by inhibition of endothelial E-selectin. J. Am. Soc. Nephrol. 16:415A (2005).
Gong et al., Hepatocyte growth factor ameliorates renal interstitial inflammation in rat remnant kidney by modulating tubular expression of macrophage chemoattractant protein-1 and RANTES. Kidney Int. 69:1166-1174-81 (2006).
Guijarro and Egido, Transcription factor-κ B (NF-κB) and renal disease. Kidney Int. 59:415-24 (2001).
Haefner, A model for NF-κB regulation by GSK-3 β. Drug Discov. Today 8:1062-3 (2003).
Heemann et al., Lipopolysaccharide pretreatment protects from renal ischemia/reperfusion injury : possible connection to an interleukin-6-dependent pathway. Am. J. Pathol. 156:287-93 (2000).
Hershkoviz et al., Activated T lymphocytes and macrophages secrete fibronectin which strongly supports cell adhesion. Cell Immunol. 141:352-61 (1992).
Hoeflich et al., Requirement for glycogen synthase kinase-3β in cell survival and NF-κB activation. Nature 406:86-90 (2000).

(Continued)

*Primary Examiner* — Lisa Cook

(74) *Attorney, Agent, or Firm* — Ropes & Gray LLP

(57) ABSTRACT

Renal injury and inflammation is diagnosed by detecting an elevation in GSK3b level or activity. Inflammation of bodily tissues such as renal tissue is inhibited by administration of GSK3b inhibitory compositions.

34 Claims, 19 Drawing Sheets

OTHER PUBLICATIONS

Holschermann et al., Statins prevent NF-κB transactivation independently of the IKK-pathway in human endothelial cells. Atherosclerosis 185(2):240-5 (2006).

Igarashi et al., Kidney-specific gene targeting, J. Am. Soc. Nephrol. 15:2237-2239 (2004).

Jankovic et al., Cation-induced immunosuppression: the effect of lithium or Arthus reactivity, delayed hypersensitivity and antibody production in the rat. Adv. Exp. Med. Biol. 114:339-44 (1979).

Jope and Johnson, The glamour and gloom of glycogen synthase kinase-3. Trends Biochem. Sci. 29:95-102 (2004).

Junaid and Amara, Osteopontin: correlation with interstitial fibrosis in human diabetic kidney and PI3-kinase-mediated enhancement of expression by glucose in human proximal tubular epithelial cells. Histopathology 44:136-46 (2004).

Kok et al., Specific delivery of captopril to the kidney with the prodrug captopril-lysozyme. J. Pharmacol. Exp. Ther. 288 (1):281-5 (1999).

Lan, Tubular epithelial-myofibroblast transdifferentiation mechanisms in proximal tubule cells. Curr. Opin. Nephrol. Hypertens. 12:25-29 (2003).

Lax et al., DEffects of salt restriction on renal growth and glomerular injury in rats with remnant kidneys. Kidney Int. 41:1527-34 (1992).

Levine and Saltzman, Inhibition of experimental allergic encephalomyelitis by lithium chloride: specific effect or nonspecific stress? Immunopharmacology 22:207-13 (1991).

Lin et al., Wnt/β-Catenin Signaling Modulates Survival of High Glucose-Stressed Mesangial Cells. J. Am. Soc. Nephrol. 17:2812-20 (2006).

Lloberas et al., Postischemic renal oxidative stress induces inflammatory response through PAF and oxidized phospholipids. Prevention by antioxidant treatment. FASEB J. 16:908-10 (2002).

Main et al., T cells and macrophages and their role in renal injury. Semin. Nephrol. 12:395-407 (1992).

Martin et al., Toll-like receptor-mediated cytokine production is differentially regulated by glycogen synthase kinase 3. Nat. Immunol. 6:777-84 (2005).

Martinez et al., First non-ATP competitive glycogen synthase kinase 3β (GSK-3β) inhibitors: thiadiazolidinones (TDZD) as potential drugs for the treatment of Alzheimer's disease. J. Med. Chem. 45:1292-9 (2002).

Martinez et al., Glycogen synthase kinase 3 (GSK-3) inhibitors as new promising drugs for diabetes, neurodegeneration, cancer, and inflammation. Med. Res. Rev. 22:373-84 (2002).

Nangaku, Mechanisms of tubulointerstitial injury in the kidney: final common pathways to end-stage renal failure. Intern. Med. 43:9-17 (2004).

Nathan, Points of control in inflammation. Nature 420:846-52 (2002).

Nathan, Secretory products of macrophages. J. Clin. Invest. 79:319-26 (1987).

Navarro et al., Tumor necrosis factor-alpha gene expression in diabetic nephropathy: relationship with urinary albumin excretion and effect of angiotensin-converting enzyme inhibition. Kidney Int. Suppl. S98-102 (2005).

Nikoulina et al., Potential role of glycogen synthase kinase-3 in skeletal muscle insulin resistance of type 2 diabetes. Diabetes 49:263-71 (2000).

O'Riordan et al., Effect of lithium therapy on inflammatory response. Inflammation 10:49-57 (1986).

O'Riordan et al., Endothelial cell dysfunction: the syndrome in making. Kidney Int. 67:1654-8 (2005).

Remuzzi and Bertani, Pathophysiology of progressive nephropathies. N. Engl. J. Med. 339:1448-56 (1998).

Ricardo and Diamond, The role of macrophages and reactive oxygen species in experimental hydronephrosis. Semin. Nephrol. 18:612-21 (1998).

Rodriguez-Iturbe et al., Role of immunocompetent cells in nonimmune renal diseases. Kidney Int. 59:1626-40 (2001).

Schwabe and Brenner, Role of glycogen synthase kinase-3 in TNF-α-induced NF-κB activation and apoptosis in hepatocytes. Am. J. Physiol. Gastrointest. Liver Physiol. 283:G204-11 (2002).

Shirota et al., Characterization of novel kidney-specific delivery system using an alkylglucoside vector, J. Pharmacol. Exp. Ther. 299(2):459-67 (2001).

Smith et al., Anticonvulsants as a cause of Fanconi syndrome. Nephrol. Dial. Transplant 10:543-5 (1995).

Smith, Leukocyte-endothelial cell interactions. Semin Hematol 30:45-53 (1993).

Steinbrecher et al., Glycogen synthase kinase 3β functions to specify gene-specific, NF-κB-dependent transcription. Mol. Cell. Biol. 25:8444-55 (2005).

Taal et al., Proinflammatory gene expression and macrophage recruitment in the rat remnant kidney. Kidney Int. 58:1664-76 (2000).

Terzi et al., Subtotal but not unilateral nephrectomy induces hyperplasia and protooncogene expression. Am. J. Physiol. 268:F793-801 (1995).

Timmer and Sands, Lithium intoxication. J. Am. Soc. Nephrol. 10:666-74 (1999).

To and Tsao, The roles of hepatocyte growth factor/scatter factor and met receptor in human cancers (Review). Oncol. Rep. 5:1013-24 (1998).

Utimura et al., Mycophenolate mofetil prevents the development of glomerular injury in experimental diabetes. Kidney Int. 63:209-16 (2003).

Vaage and Lindblad, Production of collagen type I by mouse peritoneal macrophages. J. Leukoc. Biol. 48:274-80 (1990).

Wang et al., Induction of monocyte chemoattractant protein-1 by albumin is mediated by nuclear factor κB in proximal tubule cells. J. Am. Soc. Nephrol. 10:1204-13 (1999).

Weber and Erl, Modulation of vascular cell activation, function, and apoptosis: role of antioxidants and nuclear factor-κB. Curr. Top. Cell. Regul. 36:217-35 (2000).

Whittle et al., Reduction of experimental colitis in the rat by inhibitors of glycogen synthase kinase-3β. Br. J. Pharmacol. 147:575-82 (2006).

Woodgett and Ohashi, GSK3: an in-Toll-erant protein kinase? Nat. Innmunol. 6:751-2 (2005).

Ziolkowska et al., Valproic acid prevents skin disease and attenuates severity of kidney disease in MrI-lpr/lpr lupus-like mouse model. Am. College of Rheumatol. 1686 (2006).

Matsumoto and Nakamura, 2002, Renotropic role and therapeutic potential of HGF in the kidney, Nephrol. Dial. Transplant 17(9):59-61.

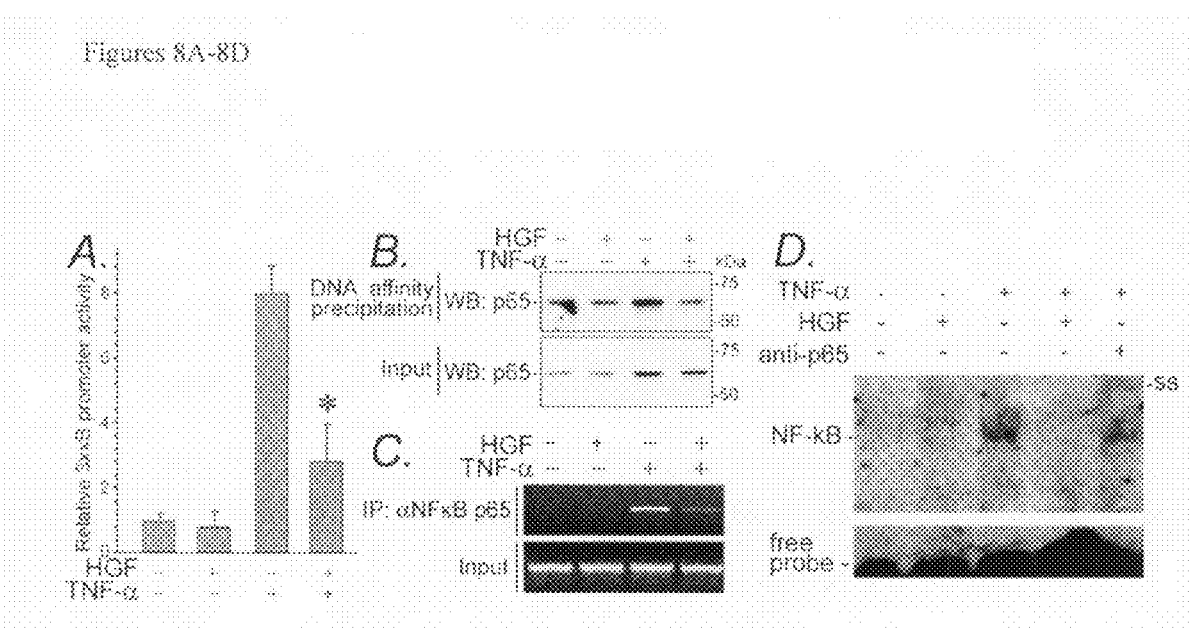

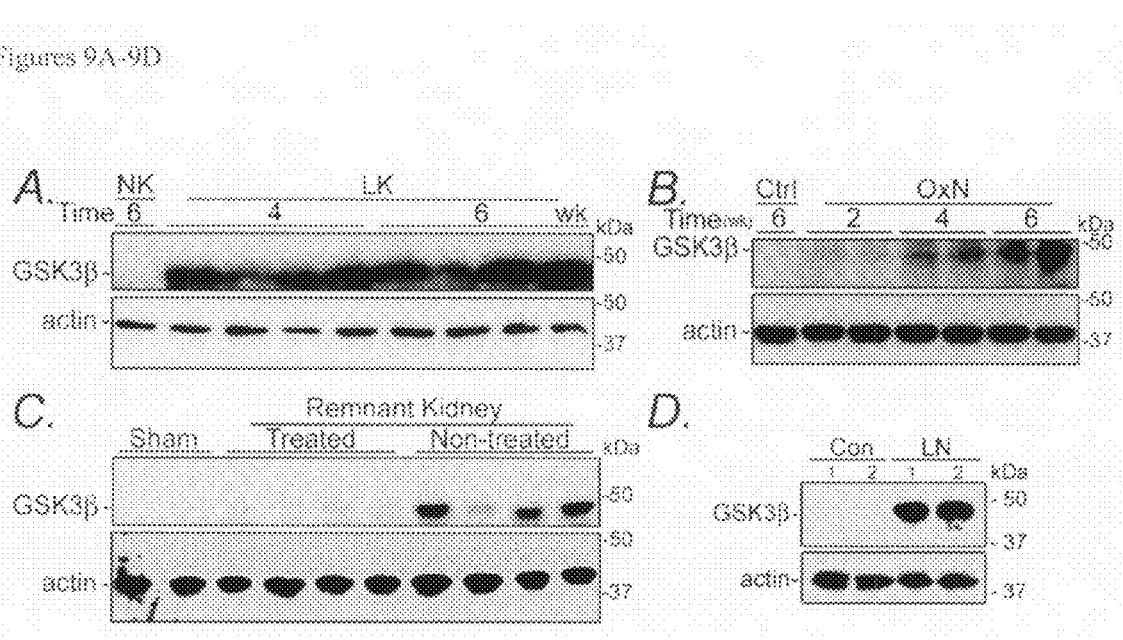

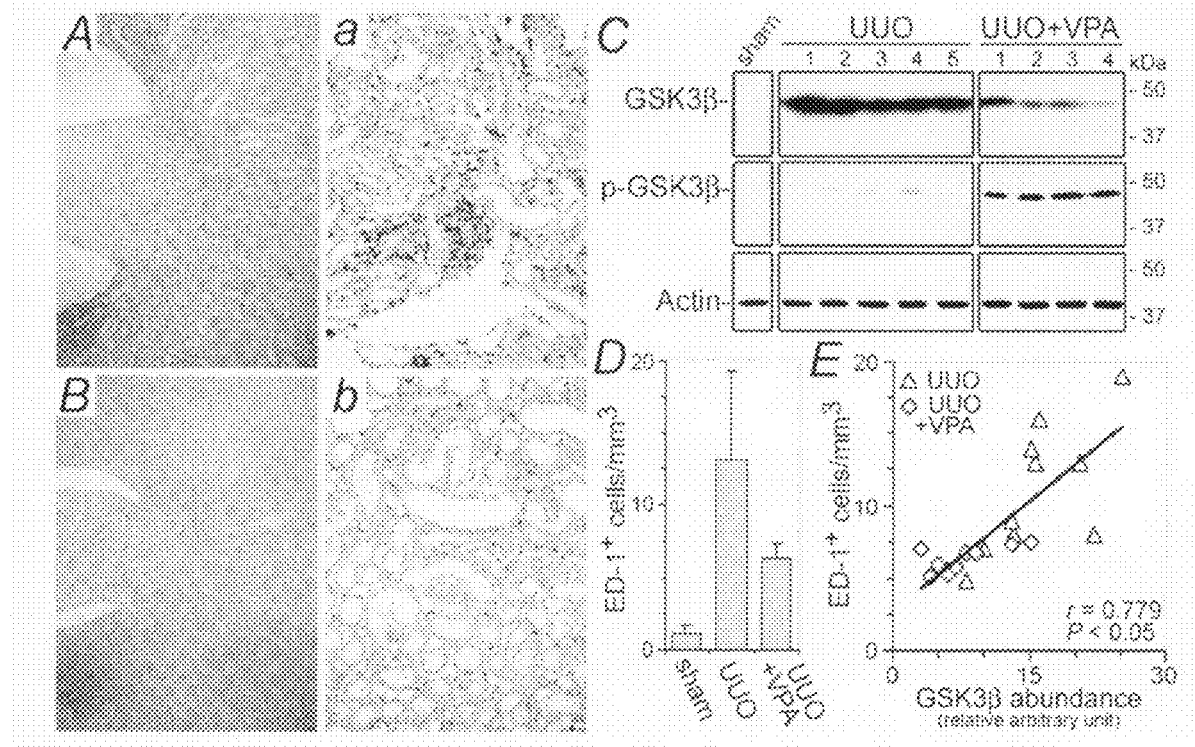

COMPOSITIONS AND METHODS FOR DETECTING AND TREATING RENAL INJURY AND INFLAMMATION

RELATED APPLICATION

This application claims the benefit of U.S. Provisional Patent Application Ser. No. 60/828,378, filed on Oct. 5, 2006, the entire disclosure of which is incorporated herein by this reference.

SEQUENCE LISTING

The instant application contains a Sequence Listing which has been submitted in ASCII format via EFS-Web and is hereby incorporated by reference in its entirety. Said ASCII copy, created on Feb. 11, 2011, is named LHSD-140-101 _Text_SL and is 1,877 bytes in size.

FIELD OF THE INVENTION

The present invention relates to inflammatory conditions and kidney injury and disease.

BACKGROUND OF THE INVENTION

Inflammation (irritation with swelling and presence of increased numbers of immune cells) caused by immune responses to toxins, medications, infection, or other disorders may injure the structures of the kidney, leading to various types of glomerulonephritis or acute tubular necrosis (tissue death). Autoimmune disorders may also damage the kidneys. Injury to the kidney may result in short-term damage with minimal or no symptoms, or it can be life-threatening as in the case of acute renal failure or chronic renal failure.

Most forms of chronic kidney disease (CKD) progress inexorably to end stage renal disease (ESRD), which has considerable morbidity and a 20% annual mortality. While the initiators of CKD vary, it is generally accepted that secondary processes common to all renal diseases ensue, establishing a vicious cycle of progressive nephron destruction leading to glomerulosclerosis and tubulo-interstitial fibrosis. A growing body of evidence suggests that renal inflammation is a key secondary process driving progression of such disorders.

Immunosuppressants including glucocorticoids, which directly inhibit NF-kB activity are widely used to treat patients with excessive acute or chronic renal inflammation. However, these drugs often prove to be marginally effective and have been associated with significant adverse side effects. There is an urgent need for effective treatments of kidney inflammation and disease with fewer adverse side effects.

SUMMARY OF THE INVENTION

The invention represents a major advance in the diagnosis and treatment of an inflammatory condition such as that associated with renal injury or disease. Such conditions include acute and chronic kidney disease including glomerulonephritis, glomerulosclerosis, and diabetic nephropathy. A method of diagnosing renal injury in a mammal is carried out by detecting a level of Glycogen synthase kinase-3β (GSK3b; GENBANK accession number CAG38748, AAH12760, NP002084, P49841, AAH00251, or AAM88578) in a bodily fluid or bodily tissue. An increase in GSK3b level of expression or enzymatic activity in the tissue or fluid sample from the mammal compared to a normal control level indicates that the mammal has a renal injury or inflammation of renal tissue. For example, the level of GSK3b expression or activity is increased by at least 10%, 20%, 50%, 75%, 2-fold, 6-fold, 8-fold, 10-fold or more compared to a normal control level. A normal control level of GSK3b in kidney tissue is a negligible amount (barely detectable). An advantage of this diagnostic method is that it permits very early detection of injury and/or inflammation. For example, the test subject is characterized as having a creatinine level or a urinary protein level in a normal range (standard measures of renal pathology) but an elevated GSK3b level compared to normal GSK3b level. Normal creatinine levels are in the range of 0.6 to 1.4 mg/dl. Normal urine protein levels are less than approximately 30 mg/gram of creatinine.

Mammals to be diagnosed and treated as described herein include humans, cats, dogs, horses, cows or other animals. Bodily samples to be tested include blood, serum, plasma, urine, saliva as well as tissue samples such as those obtained by surgical biopsy procedures. Testing is generally done in vitro by measuring the abundance of GSK3B, e.g., by Western blotting or by immunohistochemistry or by other methods known in the art to determine the protein level of GSK.

GSK3b levels are measured by detecting presence of the protein, nucleic acid transcript, and/or enzyme activity. For example, GSK3b levels are measured by Western blot or immunohistochemical assays to detect protein or by PCR, e.g., real time PCR, to detect nucleic acid transcripts.

The method includes a step of contacting a bodily fluid or bodily tissue with a detectable composition that binds to GSK3b. For example, the composition is an antibody or antibody fragment or other compositions that bind to GSk3b under conditions sufficient to form an immune complex or binding complex and detecting the immune or other binding complex to determine a GSK level. Alternatively, the method includes a step of contacting the fluid or tissue with a substrate of the GSK3b enzyme and detecting enzymatic activity such as NF-kB p65 phosphorylation or IkB phosphorylation and degradation.

A method or prognosis of renal injury or inflammatory condition of a mammal is carried out by detecting a level of GSK3b in a bodily fluid or bodily tissue in a plurality of sample over time. An increase in the level over time indicates an adverse prognosis or an increase in severity of disease/inflammation.

Also within the invention if a kit containing a GSK3b ligand, a detectable marker, a sealed vial containing a predetermined level of GSK3b (protein or enzymatic activity), and instructions for evaluating renal or other inflammation as it correlates with GSK3b concentration or activity.

A method of reducing inflammation of a bodily tissue involves administering to a mammal that has been diagnosed as suffering from or at risk of developing an inflamed tissue a GSK3b inhibitory compound. The mammal to be treated is diagnosed as having an elevated level of GSK3b compared to a normal control level. The inflamed tissue is renal tissue. Alternatively, the tissue is lung, liver, a gastrointestinal tissue such as bowel tissue. The mammal is diagnosed as suffering from or at risk of developing an acute kidney injury or infection such as repeated kidney infections, or a chronic condition, e.g., diabetes or hypertension, that may lead to chronic kidney disease. Other subjects to be treated include those diagnosed with or suffering form glomerulonephritis, glomerulosclerosis, diabetic nephropathy, polycystic kidney disease, a congenital kidney pathology, Lupus or other diseases that affect the body's immune system, and obstructions such as kidney stones, tumors or an enlarged prostate gland.

Administration is preferably oral or by injection, e.g., intravenous, intramuscular, subcutaneously injection.

GSK3b inhibitors include lithium and valproic acid as well as other selective or non-selective GSK3b inhibitors. Preferably, the inhibitory compound does not substantially alter c-AMP signaling. The advantage of GSK3b inhibition over present therapeutic strategies to treat renal inflammation, e.g., corticosteroids, is that they are better tolerated and are less toxic.

The antibodies described herein are purified. By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., a GSK3b specific antibody. A purified antibody is obtained, for example, by affinity chromatography using recombinantly-produced protein or conserved motif peptides and standard techniques. Preferably, the antibody binds specifically to human GSK3b.

In certain aspects, the disclosure provides a method of detecting whether a subject has
renal injury or disease comprising:
 (a) obtaining a sample of a fluid or bodily tissue from said subject;
 (b) assessing the level of GSK3b,
wherein an increase in said level in said subject compared to a normal control level is indicative that the subject has renal injury or disease. In certain embodiments, said subject is a human. In certain embodiments, an increase of at least 10% compared to said normal control indicates that said subject comprises a renal injury or disease. In certain embodiments, an increase of at least 50% compared to said normal control indicates that said subject comprises a renal injury or disease. In certain embodiments, an increase of at least 2-fold compared to said normal control indicates that said subject comprises a renal injury or disease.

In certain embodiments, said subject comprises a creatinine level or a urinary protein level in a normal range. In certain embodiments, said bodily fluid is selected from the group consisting of blood, serum, plasma, urine, saliva, cerebral spinal fluid, joint fluid, fluid from the pleural space, and peritoneal fluid. In certain embodiments, said bodily tissue is a tissue biopsy. In certain embodiments, the presence of GSK3b is a detectable level of GSK3b. In certain embodiments, said bodily fluid or bodily tissue is contacted with a detectable composition that binds to GSK3b.

In certain embodiments, said composition is an antibody. In certain embodiments, said antibody and said bodily fluid or bodily tissue are contacted under conditions sufficient to form an immune complex and detecting the immune complex to determine a GSK level. In certain embodiments, said antibody or antigen binding fragment thereof is selected from the group consisting of a polyclonal antibody, a monoclonal antibody or antibody fragment, a diabody, a chimerized or chimeric antibody or antibody fragment, a humanized antibody or antibody fragment, a deimmunized human antibody or antibody fragment, a fully human antibody or antibody fragment, a single chain antibody, an Fv, an Fd, an Fab, an Fab', and an F(ab')2. In certain embodiments, said antibody or antigen binding fragment thereof is a monoclonal antibody. In certain embodiments, the antibody or antigen binding fragment thereof is covalently linked to an additional functional moiety. In certain embodiments, the additional functional moiety is a detectable label. In certain embodiments, the detectable label is selected from a fluorescent or chromogenic label. In certain embodiments, the detectable label is selected from horseradish peroxidase or alkaline phosphatase.

In certain aspects, the disclosure provides a method of developing a prognosis for a patient suffering from renal injury or disease comprising:
 (a) obtaining a sample from said subject;
 (b) assessing the level of GSK3b in said sample,
wherein a high level of GSK3b is indicative of a poor prognosis. In certain embodiments, said subject is a human. In certain embodiments, an increase in said level over time indicates an adverse prognosis or an increase in severity of disease.

In certain embodiments, said subject comprises a creatinine level or a urinary protein level in a normal range. In certain embodiments, said bodily fluid is selected from the group consisting of blood, serum, plasma, urine, saliva, cerebral spinal fluid, joint fluid, fluid from the pleural space, and peritoneal fluid. In certain embodiments, said bodily tissue is a tissue biopsy. In certain embodiments, the presence of GSK3b is a detectable level of GSK3b. In certain embodiments, said bodily fluid or bodily tissue is contacted with a detectable composition that binds to GSK3b.

In certain embodiments, said composition is an antibody. In certain embodiments, said antibody and said bodily fluid or bodily tissue are contacted under conditions sufficient to form an immune complex and detecting the immune complex to determine a GSK level. In certain embodiments, said antibody or antigen binding fragment thereof is selected from the group consisting of a polyclonal antibody, a monoclonal antibody or antibody fragment, a diabody, a chimerized or chimeric antibody or antibody fragment, a humanized antibody or antibody fragment, a deimmunized human antibody or antibody fragment, a fully human antibody or antibody fragment, a single chain antibody, an Fv, an Fd, an Fab, an Fab', and an F(ab')2. In certain embodiments, said antibody or antigen binding fragment thereof is a monoclonal antibody. In certain embodiments, the antibody or antigen binding fragment thereof is covalently linked to an additional functional moiety. In certain embodiments, the additional functional moiety is a detectable label. In certain embodiments, the detectable label is selected from a fluorescent or chromogenic label. In certain embodiments, the detectable label is selected from horseradish peroxidase or alkaline phosphatase.

In certain aspects, the disclosure provides a kit comprising a GSK3b ligand, a detectable marker, a sealed vial comprising a predetermined level of GSK3b, and instructions for evaluating renal inflammation.

In certain aspects, the disclosure provides a method of reducing inflammation of a bodily tissue in a subject, comprising administering to said subject comprising an inflamed tissue a GSK3b inhibitory compound. In certain embodiments, said subject is a human. In certain embodiments, said GSK3b inhibitory compound blocks GSK3b-mediated phosphorylation of NFkB p65 at amino acid residue S468.

In certain embodiments, said subject is diagnosed as comprising an elevated level of GSK3b compared to a normal control level. In certain embodiments, said bodily tissue is renal tissue. In certain embodiments, said subject is diagnosed as suffering from or at risk of developing a chronic kidney disease. In certain embodiments, said GSK3b inhibitory compound selectively inhibits GSK3b compared to other enzymes.

In certain embodiments, said inhibitory compound is selected from the group consisting of lithium, valproic acid, and TDZD-8. In certain embodiments, said inhibitory compound does not substantially alter c-AMP signaling. In certain embodiments, said inhibitory compound is administered before abnormal creatinine or urine protein concentration is detected. In certain embodiments, said subject is diagnosed as suffering from or at risk of developing a disease selected from the group consisting of: hypokalemic nephropathy, remnant kidney disease, oxalate nephropathy, lupus nephritis, and unilateral urethral obstruction.

In certain embodiments, said GSK3b inhibitory compound further comprises a kidney targeting agent. In certain embodiments, the targeting agent is a peptide. In certain embodiments, the targeting agent is an aptamer.

In certain aspects, the disclosure provides a method of treating inflammatory-mediated kidney disease in a subject, comprising administering to said subject a GSK3b inhibitory compound. In certain embodiments, said subject is a human. In certain embodiments, said GSK3b inhibitory compound blocks GSK3b-mediated phosphorylation of NFkB p65 at amino acid residue S468.

In certain embodiments, said kidney disease selected from the group consisting of: glomerlilar nephritis, lupus nephritis, and interstitial nephritis. In certain embodiments, said kidney disease is a chronic kidney disease.

In certain embodiments, said GSK3b inhibitory compound selectively inhibits GSK3b compared to other enzymes. In certain embodiments, said inhibitory compound is selected from the group consisting of lithium, valproic acid, and TDZD-8. In certain embodiments, said inhibitory compound does not substantially alter c-AMP signaling. In certain embodiments, said inhibitory compound is administered before abnormal creatinine or urine protein concentration is detected.

In certain embodiments, said GSK3b inhibitory compound further comprises a kidney targeting agent. In certain embodiments, the targeting agent is a peptide. In certain embodiments, the targeting agent is an aptamer.

In certain aspects, the disclosure provides a composition for the treatment of kidney disease, wherein said composition blocks GSK3b-mediated phosphorylation of NFkB p65 at amino acid residue S468.

In certain aspects, the disclosure provides an inhibitor of inflammation, wherein said inhibitor blocks GSK3b-mediated phosphorylation of NFkB p65 at amino acid residue S468.

In certain aspects, the disclosure provides an inhibitor of GSK3b, wherein said inhibitor blocks GSK3b-mediated phosphorylation of NFkB p65 at amino acid residue S468.

The invention contemplates combinations of any of the foregoing aspects and embodiments of the invention. Other embodiments are described in the description. All references cited herein are hereby incorporated by reference.

BRIEF DESCRIPTION OF THE DRAWINGS

FIGS. 8A-8D show that HGF suppresses NF-kB activation in endothelial cells and tubular epithelial cells. (A) NF-kB gene reporter assay; (B) DNA affinity precipitation assay and (C) chromatin immunoprecipitation assay (ChIP) all show that HGF blunts NF-kB activation and its target E-selectin gene in HUVEC. (D) Gel shift assay shows that TNF-a induces NF-kB activity is attenuated by HGF. ss, supershift.

FIGS. 9A-9D show that renal expression of GSK3b is markedly elevated in inflammatory kidney disease. (A) In rat hypokalemic nephropathy, GSK3b is markedly induced in the kidney beginning 4 weeks and is enhanced at 6 weeks. NK, LK, normal or low potassium diet. (B) In rat oxalate nephropathy models, renal GSK3b abundance is progressively elevated along the course of the disease. Ctrl, control; OxN, oxalate nephropathy. (C) In rat remnant kidney mode\, renal GSK3b level is markedly increased at 4 weeks after renal ablation and is attenuated by a therapeutic treatments. (D) GSK3 β is significantly induced at week 9 of disease in a murine model of lupus nephritis (LN) that was induced in (C57BL/6×DBA/2) F(1) hybrid mice injected of DBA/2 lymphocytes. Con, control.

FIGS. 13A-13E show that valproate (VPA), a selective GSK3b inhibitor, markedly ameliorates renal inflammation in rats with unilateral urethral obstruction(UUO). (A,a,B,b) Immunohistochemistry staining of ED-1, a marker of rat macrophages, showed abundant inflammatory infiltration in the obstructed kidney treated with vehicle (A, a) and diminished renal inflammation in VPA (200 mg/kg/d, ip) treated rats (B, b). (A,B) ×100 magnification; (a,b)×200 magnification. (C)Immunoblot analysis of kidmey homogenates revealed elevated renal expression of GSK3b in UUO rats as compared to those received sham operation (sham). VPA treatments substantially suppressed total GSK3b expression but enhanced its inhibitory phosphorylation. (D) absolute counting of ED-1+ cells in renal sections. P<0.05 UUO vs UUO+VPA, n=10 for each group; (E) Correlation of ED-1+ cells with abundance of renal expression of GSK3b (P<0.05.)

(FIG. 1A discloses SEQ ID NOS 5-6, respectively in order of appearance); B, After different treatments as indicated, whole cell lysates were subjected to immunoprecipitation by anti-GSK3b or anti-p65 antibody. Immunoprecipitates were then probed for different molecules. C, After transfected with different vectors, HKC cells were treated with HGF, TNF-a or in combination before whole cell lysates were collected and subjected to immunoprecipitation by anti-hemagglutin or anti-p65 antibody. Immunoprecipitates were then probed for different molecules.

DETAILED DESCRIPTION

I. Overview

Inflammation is a basic biological response to injury, rapidly subsiding after acute organ injury but often continuing in chronic diseases where it contributes to fibrosis and loss of function[20]. Almost all progressive renal diseases are characterized by an inflammatory infiltrate. Infiltrating cells secret ECM components directly contributing to matrix accumulation[21,22]. Leukocytes generate radical oxygen species, lipid mediators, and proinflammatory cytokines that damage tissues establishing a positive feedback loop[23-25]. Mononuclear cells including lymphocytes and macrophages produce profibrotic molecules such as TGF-β1, FGF, and PDGF[25]. These factors activate resident fibroblasts and generate myofibroblasts from TEC via epithelial-mesenchymal transition[26]. Heterogeneous fibroblasts proliferate and produce matrix leading to renal fibrosis. The extent of inflammation correlates with functional impairment and with long-term prognosis in patients with kidney disease[27]. Even in "non-immune" models of renal disease such as remnant kidney and diabetic nephropathy, non-specific suppression of renal inflammation is highly beneficial[28-30].

Glycogen synthase kinase-3 (GSK3) is a proline-directed serine-threonine kinase that was initially identified as a phosphorylating and inactivating glycogen synthase. Two isoforms, alpha (GSK3a) and beta, show a high degree of amino acid homology. GSK3b is involved in energy metabolism, neuronal cell development, and body pattern formation. GSK3b protein is inhibited by phosphorylation of serine-9 and is activated by phosphorylation of tyrosine-216.

GSK3b is a ubiquitously expressed serine-threonine kinase originally implicated in the regulation of glucose metabolism, It resides at the nexus of multiple signaling pathways implicated in NF-kB activation and the generation of an inflammatory response. GSK3b expression and kinase activity were found to be increased in brains of subjects with neurodegenerative disease and skeletal muscles from patients with insulin resistance.

Figure 1:
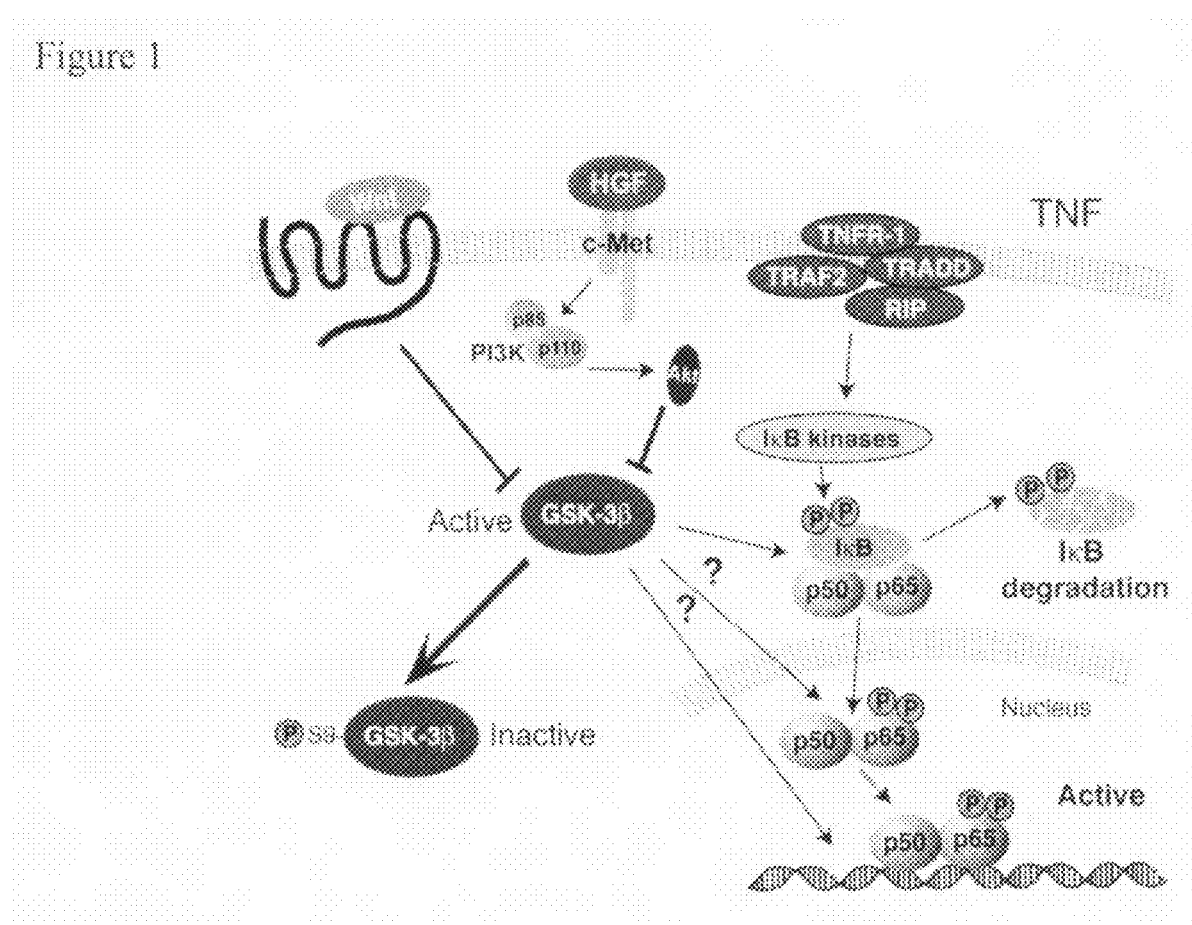
FIG. 1 illustrates that GSK3b regulates NF-κB activation and controls the expression of NF-κB target genes by undefined mechanisms, which might include NF-κB phosphorylation, nuclear translocation, DNA binding and transactivation of downstream genes. GSK3b is inactivated by inhibitory phosphorylation at serine 9, by multiple signaling pathways, e.g. Wnt and PI3K-Akt.

Nuclear factor-kB (NF-kB) is a family of dimeric transcription factors that regulate the expression of numerous genes involved in inflammation and cell proliferation in many tissues, including kidney[18]. Under basal conditions, NF-κB resides in the cytoplasm in an inactive form, complexed to an inhibitor (IκB). Active NF-kB is a homodimer or heterodimer, composed of two member proteins of the NF-κB family (p50, p52, p65, (RelA), rel B, and c-Rel). Pro-inflammatory substances such as TNF-α, IL-1β, lipopolysaccharide (LPS) and/or phorbol myristate acetate (PMA) induce the dissociation of the cytoplasmic NF-κB/IkB complex, with subsequent translocation of active NF-κB to the nucleus. In the nucleus, NF-κB binds to DNA motifs on the promoters of various genes, particularly those associated with immune or inflammatory responses. NF-κB activation is a key event in conditions in which either inflammation or proliferation are prominent, including progressive renal disease. Active NF-κB has been found in renal tubular epithelial cells and urothelial cells following a variety of pro-inflammatory stimuli. For example, albumin activates NF-κB and this may be relevant to tubular injury and fibrosis in proteinuric states[31]. Angiotensin II and endothelin also activate NF-κB in tubular cells 32. Activation of NF-κB is a complex and highly orchestrated process, regulated by many signal transducers including GSK3b[38-42] (FIG. 1).

Endothelial dysfunction, characterized by elevated expression of endothelin, de novo expression of E-selectin, and aberrant expression of other adhesion molecules[33], may promote ischemic/hypoxic injury in chronic renal disease[33]. All these molecules are under the control of NF-κB[34]. NF-κB activity can be pharmacologically modified both in vivo and in vitro. For example, the anti-inflammatory effects of steroids result from inhibition of transactivation of NF-κB dependent genes[35]. The beneficial effects of angiotensin-converting enzyme inhibitors[36] and statins[37] also depend, at least in part, on inhibition of NF-κB activation.

II. Definitions

A "subject" refers to a vertebrate, such as for example, a mammal, or a human. Though the inhibitors of the present application are primarily concerned with the treatment of human subjects, they may also be employed for the treatment of other mammalian subjects such as dogs and cats for veterinary purposes.

The term "derived from" means "obtained from" or "produced by" or "descending from".

The term "genetically altered antibodies" means antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

The term "an antigen-binding fragment of an antibody" refers to any portion of an antibody that retains the binding utility to the antigen. An exemplary antigen-binding fragment of an antibody is the heavy chain and/or light chain CDR, or the heavy and/or light chain variable region.

The term "homologous," in the context of two nucleic acids or polypeptides refers to two or more sequences or subsequences that have at least about 85%, at least 90%, at least 95%, or higher nucleotide or amino acid residue identity, when compared and aligned for maximum correspondence, as measured using the following sequence comparison method and/or by visual inspection. In certain embodiments, the "homolog" exists over a region of the sequences that is about 50 residues in length, at least about 100 residues, at least about 150 residues, or over the full length of the two sequences to be compared.

Methods of determining percent identity are known in the art. "Percent (%) sequence identity" with respect to a specified subject sequence, or a specified portion thereof, may be defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. 215:403-410 (1997); http://blast.wustl.edu/blast/README.htm-l) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported.

The term "specifically binds" is meant an antibody that recognizes and binds an antigen or antigenic domain such as a antigenic sequence in GSK3b but that does not substantially recognize and bind other antigen molecules in a sample.

The term "isolated" is meant a nucleic acid, polypeptide, or other molecule that has been separated from the components that naturally accompany it. Typically, the polypeptide is substantially pure when it is at least 60%, 70%, 80%, 90%, 95%, or even 99%, by weight, free from the proteins and naturally-occurring organic molecules with which is it naturally associated. For example, a substantially pure polypeptide may be obtained by extraction from a natural source, by expression of a recombinant nucleic acid in a cell that does not normally express that protein, or by chemical synthesis.

III. GSK3b Inhibitors

In certain embodiments, the inhibitors of GSK3b include any molecules that directly or indirectly counteract, reduce, antagonize or inhibit GSK3b biological activities. In one embodiment, the inhibitors of GSK3b compete or block the binding of GSK3b to its ligands. In certain embodiments, the inhibitors may counteract, reduce, or inhibit at least one biological activity of GSK3b, for example, ligand binding, down-stream signal transduction, and inflammatory activities. In certain embodiments, the inhibitors are neutralizing. In other embodiments, the inhibitors are non-neutralizing. In certain embodiments, the inhibitors may be used to treat kidney disease, injury or inflammation.

In one aspect, the inhibitors directly interact with GSK3b. In certain embodiments, the inhibitors are proteins. In certain embodiments, the proteins bind to GSK3b. In certain embodiments, the inhibitors are antibodies or antibody fragments that bind to GSK3b and neutralize at least one biological activity of GSK3b.

In another aspect, the inhibitors are any polypeptides or peptides that modulate GSK3b activities but do not directly interact with GSK3b. For example, the inhibitors can be mutated GSK3b molecules, such as dominant-negative mutants derived from a wild-type GSK3b by terminal truncations or amino acid substitutions. In certain embodiments, such mutated GSK3bs retain the binding ability to the signaling molecules of GSK3b but lose the ability of triggering the downstream signaling transduction of GSK3b. Therefore, the mutated GSK3B molecules can compete with the wild-type GSK3b and thus block the activities of the wild-type GSK3b. The standard mutagenesis and molecular cloning techniques can accomplish the terminal truncation and amino acid substitution. The mutated GSK3b molecules can be administered into the target cells by standard delivery means known in the art, such as, lipid or viral transfections. Additional examples are the blocking peptides or polypeptides that block the ligand-binding site of GSK3b with its ligands. In one example, such blocking polypeptides are the antibodies against the ligands of GSK3b.

Alternatively, the inhibitors interact with and regulate the upstream or downstream components of the GSK3b signaling pathway and indirectly reduce the activities of GSK3b. Accordingly, any molecules capable of regulating this pathway can be candidate inhibitors, including, but not limited to, the antibodies or other inhibitor blocking the binding and activities of these components. Yeast two-hybrid and variant screens offer methods for identifying endogenous additional interacting proteins of the components of the GSK3b signaling pathways (Finley et al. in DNA Cloning-Expression Systems: A Practical Approach, eds. Glover et al. (Oxford University Press, Oxford, England), pp. 169-203 (1996); Fashema et al., Gene 250: 1-14 (2000); Drees, CUK Opin Chem Biol 3: 64-70 (1999); Vidal et al. Nucleic Acids Res. 27:9191-29 (1999); and U.S. Pat. No. 5,928,868). Mass spectrometry is an alternative method for the elucidation of protein complexes (reviewed in, e. g., Pandley et al., Nature 405: 837-846 (2000); Yates, 3rd, Trends Genet 16: 5-8 (2000)).

In certain embodiments, the GSK3b inhibitory compound blocks GSK3b-mediated phosphorylation of NFkB p65 at amino acid residue S468. In certain embodiments, the level of phosphorylation of NFkB p65 at amino acid residue S468 is decreased. In certain embodiments, the level of phosphorylation of NFkB p65 at amino acid residue S468 is decreased by 90%, 80%, 70%, 60%, 50%, 40%, 30%, 20%, or 10%.

In yet another aspect, the inhibitors may inhibit the protein expression of GSK3b. GSK3b expression can be regulated at the level of transcription, such as, by a regulator of transcription factors of GSK3b, or at the level of mRNA splicing, translation or post-translation.

The inhibitors can also be nucleic acids, including, but not limited to, anti-sense nucleic acids of the nucleic acid sequence encoding part or all of GSK3b or having substantial sequence similarity to GSK3b. The DNA sequence of GSK3b is known in the art and disclosed herein. Anti-sense nucleic acid probes of DNAs encoding GSK3b, and the optimal condition of the anti-sense blocking can be developed by using the related techniques known to a skilled artisan in the field of molecular biology. Similarly, the nucleic acid reagent may belong to the class of short interfering RNA or siRNA. Various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

The inhibitors can also be ribozymes, which refer to an RNA based enzyme capable of targeting and cleaving particular base sequences in DNA and RNA. Ribozymes either can be targeted directly to cells, in a form of RNA oligonucleotides incorporating ribozyme sequences or introduced into a cell as an expression construct encoding the desired ribozyme RNA. The methods of delivering the ribozyme RNAs are known in the art.

The inhibitors of the present application also include small molecules, which may modulate the activity of proteins with enzymatic function, and/or the interactions of said proteins. Chemical agents, referred to in the art as "small molecule" compounds are typically organic, non-peptide molecules, having a molecular weight less than 10,000, less than 5,000, less than 1,000, or less than 500 daltons. This class of inhibitors includes chemically synthesized molecules, for instance, compounds from combinatorial chemical libraries. Synthetic compounds may be rationally designed or identified based on known or inferred properties of the GSK3b protein or may be identified by screening compound libraries. Alternative appropriate inhibitors of this class are natural products, particularly secondary metabolites from organisms such as plants or fungi, which can also be identified by screening compound libraries for GSK3b-modulating activity. Methods for generating and obtaining compounds are well known in the art (Schreiber S L, Science 151: 1964-1969(2000); Radmann J. and Gunther J., Science 151: 1947-1948 (2000)).

For the purpose of the present application, the inhibitors of GSK3b also include the inhibitors of the ligands of GSK3b as long as these ligand inhibitors modulate the biological activities of GSK3b ligand-receptor pairs. These ligand inhibitors may modulate the activities of at least one of the ligands of GSK3b, including antibodies against one of the GSK3b ligands, dominant-negative mutants, transcription regulators, anti-sense nucleic acid molecules, ribozyme RNA molecules, or small molecule inhibitors of at least one GSK3b ligand. GSK3b ligands can be identified and obtained via the standard techniques used in molecular biology and cell biology. For example, the GSK3b polypeptides or ligand binding domains may be used as a probe to screen a protein expression library in seeking novel GSK3b ligands.

Peptidomimetics can be compounds in which at least a portion of a subject polypeptide of the disclosure (such as for example, a polypeptide comprising an amino acid sequence of greater than 90% sequence identity to the amino acid sequence of a soluble portion of a naturally occurring GSK3b protein) is modified, and the three dimensional structure of the peptidomimetic remains substantially the same as that of the subject polypeptide. Peptidomimetics may be analogues of a subject polypeptide of the disclosure that are, themselves, polypeptides containing one or more substitutions or other modifications within the subject polypeptide sequence. Alternatively, at least a portion of the subject polypeptide sequence may be replaced with a nonpeptide structure, such that the three-dimensional structure of the subject polypeptide is substantially retained. In other words, one, two or three amino acid residues within the subject polypeptide sequence may be replaced by a non-peptide structure. In addition, other peptide portions of the subject polypeptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of disorders in a human or animal. It should be noted that peptidomimetics may or may not have similar two-dimensional chemical structures, but share common three-dimensional structural features and geometry. Each peptidomimetic may further have one or more unique additional binding elements.

IV. Nucleic Acid Therapeutic Agents

This disclosure relates to methods for inhibiting or reducing gene expression of GSK3b in kidney inflammation or disease. By "inhibit" or "reduce," it is meant that the expression of the gene, or level of nucleic acids or equivalent nucleic acids encoding GSK3b, is reduced below that observed in the absence of the nucleic acid therapeutic agents of the disclosure. By "gene," it is meant a nucleic acid that encodes a RNA, for example, nucleic acid sequences including but not limited to structural genes encoding a polypeptide.

As used herein, the term "nucleic acid therapeutic agent" or "nucleic acid agent" or "nucleic acid compound" refers to any nucleic acid-based compound that contains nucleotides and has a desired effect on a target gene. The nucleic acid therapeutic agents can be single-, double-, or multiple-stranded, and can comprise modified or unmodified nucleotides or non-nucleotides or various mixtures, and combinations thereof. Examples of nucleic acid therapeutic agents of the disclosure include, but are not limited to, antisense nucleic acids, dsRNA, siRNA, and enzymatic nucleic acid compounds.

In one embodiment, the disclosure features one or more nucleic acid therapeutic agents that independently or in combination modulate expression of the Glycogen synthase kinase-3β (GSK3b; GENBANK accession number CAG38748, AAH12760, NP002084, P49841, AAH00251, or AAM88578).

A. Antisense Nucleic Acids

In certain embodiments, the disclosure relates to antisense nucleic acids. By "antisense nucleic acid," it is meant a non-enzymatic nucleic acid compound that binds to a target nucleic acid by means of RNA-RNA, RNA-DNA or RNA-PNA (protein nucleic acid) interactions and alters the activity of the target nucleic acid (for a review, see Stein and Cheng, 1993 Science 261, 1004 and Woolf et al., U.S. Pat. No. 5,849, 902). Typically, antisense molecules are complementary to a target sequence along a single contiguous sequence of the antisense molecule. However, in certain embodiments, an antisense molecule can form a loop and binds to a substrate nucleic acid which forms a loop. Thus, an antisense molecule can be complementary to two (or more) non-contiguous substrate sequences, or two (or more) non-contiguous sequence portions of an antisense molecule can be complementary to a target sequence, or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49.

In addition, antisense DNA can be used to target nucleic acid by means of DNA-RNA interactions, thereby activating RNase H, which digests the target nucleic acid in the duplex. The antisense oligonucleotides can comprise one or more RNAse H activating region, which is capable of activating RNAse H to cleave a target nucleic acid. Antisense DNA can be synthesized chemically or expressed via the use of a single stranded DNA expression vector or equivalent thereof. By "RNase H activating region" is meant a region (generally greater than or equal to 4-25 nucleotides in length, preferably from 5-11 nucleotides in length) of a nucleic acid compound capable of binding to a target nucleic acid to form a non-covalent complex that is recognized by cellular RNase H enzyme (see for example Arrow et al., U.S. Pat. No. 5,849, 902; Arrow et al., U.S. Pat. No. 5,989,912). The RNase H enzyme binds to a nucleic acid compound-target nucleic acid complex and cleaves the target nucleic acid sequence.

The RNase H activating region comprises, for example, phosphodiester, phosphorothioate, phosphorodithioate, 5'-thiophosphate, phosphoramidate or methylphosphonate backbone chemistry, or a combination thereof. In addition to one or more backbone chemistries described above, the RNase H activating region can also comprise a variety of sugar chemistries. For example, the RNase H activating region can comprise deoxyribose, arabino, fluoroarabino or a combination thereof, nucleotide sugar chemistry. Those skilled in the art will recognize that the foregoing are non-limiting examples and that any combination of phosphate, sugar and base chemistry of a nucleic acid that supports the activity of RNase H enzyme is within the scope of the definition of the RNase H activating region and the instant disclosure.

Thus, the antisense nucleic acids of the disclosure include natural-type oligonucleotides and modified oligonucleotides including phosphorothioate-type oligodeoxyribonucleotides, phosphorodithioate-type oligodeoxyribonucleotides, methylphosphonate-type oligodeoxyribonucleotides, phosphoramidate-type oligodeoxyribonucleotides, H-phosphonate-type oligodeoxyribonucleotides, triester-type oligodeoxyribonucleotides, alpha-anomer-type oligodeoxyribonucleotides, peptide nucleic acids, other artificial nucleic acids, and nucleic acid-modified compounds.

Other modifications include those which are internal or at the end(s) of the oligonucleotide molecule and include additions to the molecule of the internucleoside phosphate linkages, such as cholesterol, cholesteryl, or diamine compounds with varying numbers of carbon residues between the amino groups and terminal ribose, deoxyribose and phosphate modifications which cleave, or crosslink to the opposite chains or to associated enzymes or other proteins which bind to the genome. Examples of such modified oligonucleotides include oligonucleotides with a modified base and/or sugar such as arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position).

Other examples of modifications to sugars include modifications to the 2' position of the ribose moiety which include but are not limited to 2'-O-substituted with an —O— lower alkyl group containing 1-6 saturated or unsaturated carbon atoms, or with an —O-aryl, or allyl group having 2-6 carbon atoms wherein such —O-alkyl, aryl or allyl group may be unsubstituted or may be substituted, (e.g., with halo, hydroxy, trifluoromethyl cyano, nitro acyl acyloxy, alkoxy, carboxy, carbalkoxyl, or amino groups), or with an amino, or halo group. Nonlimiting examples of particularly useful oligonucleotides of the disclosure have 2'-O-alkylated ribonucleotides at their 3', 5', or 31 and 5' termini, with at least four or five contiguous nucleotides being so modified. Examples of 2'-O-alkylated groups include, but are not limited to, 2'-O-methyl, 2'-O-ethyl, 2'-O-propyl, and 2'-O-butyls.

In certain cases, the synthesis of the natural-type and modified antisense nucleic acids can be carried out with, for example, a 381A DNA synthesizer or 394 DNA/RNA synthesizer manufactured by ABI (Applied Biosystems Inc.) in accordance with the phosphoramidite method (see instructions available from ABI, or F. Eckstein, Oligonucleotides and Analogues: A Practical Approach, IRL Press (1991)). In the phosphoramidite method, a nucleic acid-related molecule is synthesized by condensation between the 3'-terminus of a modified deoxyribonucleoside or modified ribonucleoside and the 5'-terminus of another modified deoxyribonucleoside, modified ribonucleoside, oligo-modified deoxyribonucleotide or oligo-modified-ribonucleotide by use of a reagent containing phosphoramidite protected with a group such as cyanoethyl group. The final cycle of this synthesis is finished to give a product with a protective group (e.g., dimethoxytrityl group) bound to a hydroxyl group at the 5'-terminus of the sugar moiety. The oligomer thus synthesized at room temperature is cleaved off from the support, and its nucleotide and phosphate moieties are deprotected. In this manner, the natural-type oligonucleic acid compound is obtained in a crude form. The phosphorothioate-type nucleic acids can also be synthesized in a similar manner to the above natural type by the phosphoramidite method with the synthesizer from ABI. The procedure after the final cycle of the synthesis is also the same as with the natural type.

The crude nucleic acids (natural type or modified) thus obtained can be purified in a usual manner e.g., ethanol precipitation, or reverse phase chromatography, ion-exchange chromatography and gel filtration chromatography in high performance liquid chromatography (HPLC), supercritical fluid chromatography, and it may be further purified by electrophoresis. A cartridge for reverse phase chromatography, such as tC18-packed SepPak Plus (long body/ENV) (Waters), can also be used. The purity of the natural-type and modified (e.g., phosphorothioate-type) nucleic acids can be analyzed by HPLC.

In certain embodiments, the antisense nucleic acids of the disclosure can be delivered, for example, as an expression plasmid which, when transcribed in the cell, produces RNA which is complementary to at least a unique portion of the cellular MRNA which encodes a GSK3b polypeptide. Alternatively, the construct is an oligonucleotide which is generated ex vivo and which, when introduced into the cell causes inhibition of expression by hybridizing with the mRNA and/or genomic sequences encoding a GSK3b polypeptide. Such oligonucleotide probes are optionally modified oligonucleotide which are resistant to endogenous nucleases, e.g., exonucleases and/or endonucleases, and are therefore stable in vivo. Exemplary nucleic acid compounds for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in nucleic acid therapy have been reviewed, for example, by van der Krol et al., (1988) Biotechniques 6:958-976; and Stein et al., (1988) Cancer Res 48:2659-2668.

B. dsRNA and RNAi Constructss

In certain embodiments, the disclosure relates to double stranded RNA (dsRNA) and RNAi constructs. The term "dsRNA" as used herein refers to a double stranded RNA molecule capable of RNA interference (RNAi), including siRNA (see for example, Bass, 2001, Nature, 411, 428-429; Elbashir et al., 2001, Nature, 411, 494-498; and Kreutzer et al., PCT Publication No. WO 00/44895; Zernicka-Goetz et al., PCT Publication No. WO 01/36646; Fire, PCT Publication No. WO 99/32619; Plaetinck et al., PCT Publication No. WO 00/01846; Mello and Fire, PCT Publication No. WO 01/29058; Deschamps-Depaillette, PCT Publication No. WO 99/07409; and Li et al., PCT Publication No. WO 00/44914). In addition, RNAi is a term initially applied to a phenomenon observed in plants and worms where double-stranded RNA (dsRNA) blocks gene expression in a specific and post-transcriptional manner. RNAi provides a useful method of inhibiting gene expression in vitro or in vivo.

The term "short interfering RNA," "siRNA," or "short interfering nucleic acid," as used herein, refers to any nucleic acid compound capable of mediating RNAi or gene silencing when processed appropriately be a cell. For example, the siRNA can be a double-stranded polynucleotide molecule comprising self-complementary sense and antisense regions, wherein the antisense region comprises complementarity to a target nucleic acid compound (e.g., GSK3b). The siRNA can be a single-stranded hairpin polynucleotide having self-complimentary sense and antisense regions, wherein the antisense region comprises complementarity to a target nucleic acid compound. The siRNA can be a circular single-stranded polynucleotide having two or more loop structures and a stem comprising self-complimentary sense and antisense regions, wherein the antisense region comprises complementarity to a target nucleic acid compound, and wherein the circular polynucleotide can be processed either in vivo or in vitro to generate an active siRNA capable of mediating RNAi. The siRNA can also comprise a single stranded polynucleotide having complementarity to a target nucleic acid compound, wherein the single stranded polynucleotide can further comprise a terminal phosphate group, such as a 5'-phosphate (see for example Martinez et al., 2002, Cell., 110, 563-574), or 5',3'-diphosphate.

Optionally, the siRNAs of the disclosure contain a nucleotide sequence that hybridizes under physiologic conditions of the cell to the nucleotide sequence of at least a portion of the mRNA transcript for the gene to be inhibited (the "target" gene). The double-stranded RNA need only be sufficiently similar to natural RNA that it has the ability to mediate RNAi. Thus, the disclosure has the advantage of being able to tolerate sequence variations that might be expected due to genetic mutation, strain polymorphism or evolutionary divergence. The number of tolerated nucleotide mismatches between the target sequence and the siRNA sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the siRNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

The double-stranded structure of dsRNA may be formed by a single self-complementary RNA strand, two complementary RNA strands, or a DNA strand and a complementary RNA strand. Optionally, RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

As described herein, the subject siRNAs are around 19-30 nucleotides in length, and even more preferably 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group. In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of the subject dsRNAs (e.g., siRNAs) can be carried out by chemical synthetic methods or by recombinant nucleic acid techniques. Endogenous RNA polymerase of the treated cell may mediate transcription in vivo, or cloned RNA polymerase can be used for transcription in vitro. As used herein, dsRNA or siRNA molecules of the disclosure need not be limited to those molecules containing only RNA, but further encompasses chemically-modified nucleotides and non-nucleotides. For example, the dsRNAs may include modifications to either the phosphate-sugar backbone or the nucleoside, e.g., to reduce susceptibility to cellular nucleases, improve bioavailability, improve formulation characteristics, and/or change other pharmacokinetic properties. To illustrate, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The dsRNAs may be produced enzymatically or by partial/total organic synthesis, any modified ribonucleotide can be introduced by in vitro enzymatic or organic synthesis. Methods of chemically modifying RNA molecules can be adapted for modifying dsRNAs (see, e.g., Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an dsRNA can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). In certain cases, the dsRNAs of the disclosure lack 2'-hydroxy (2'-OH) containing nucleotides.

In a specific embodiment, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In another specific embodiment, the subject dsRNA can also be in the form of a long double-stranded RNA. For example, the dsRNA is at least 25, 50, 100, 200, 300 or 400 bases. In some cases, the dsRNA is 400-800 bases in length. Optionally, the dsRNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In a further specific embodiment, the dsRNA is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

PCT application WO 01/77350 describes an exemplary vector for bi-directional transcription of a transgene to yield both sense and antisense RNA transcripts of the same transgene in a eukaryotic cell. Accordingly, in certain embodiments, the present disclosure provides a recombinant vector having the following unique characteristics: it comprises a viral replicon having two overlapping transcription units arranged in an opposing orientation and flanking a transgene for a dsRNA of interest, wherein the two overlapping transcription units yield both sense and antisense RNA transcripts from the same transgene fragment in a host cell.

C. Enzymatic Nucleic Acid Compounds

In certain embodiments, the disclosure relates to enzymatic nucleic acid compounds. By "enzymatic nucleic acid compound," it is meant a nucleic acid compound which has complementarity in a substrate binding region to a specified target gene, and also has an enzymatic activity which is active to specifically cleave a target nucleic acid. It is understood that the enzymatic nucleic acid compound is able to intermolecularly cleave a nucleic acid and thereby inactivate a target nucleic acid compound. These complementary regions allow sufficient hybridization of the enzymatic nucleic acid compound to the target nucleic acid and thus permit cleavage. One hundred percent complementarity (identity) is preferred, but complementarity as low as 50-75% can also be useful in this disclosure (see for example Werner and Uhlenbeck, 1995, Nucleic Acids Research, 23, 2092-2096; Hammann et al., 1999, Antisense and Nucleic Acid Drug Dev., 9, 25-31). The enzymatic nucleic acids can be modified at the base, sugar, and/or phosphate groups. As described herein, the term "enzymatic nucleic acid" is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid compounds with enzymatic activity. The specific enzymatic nucleic acid compounds described in the instant application are not limiting in the disclosure and those skilled in the art will recognize that all that is important in an enzymatic nucleic acid compound of this disclosure is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030).

Several varieties of naturally-occurring enzymatic nucleic acids are currently known. Each can catalyze the hydrolysis of nucleic acid phosphodiester bonds in trans (and thus can cleave other nucleic acid compounds) under physiological conditions. In general, enzymatic nucleic acids act by first binding to a target nucleic acid. Such binding occurs through the target binding portion of a enzymatic nucleic acid which is held in close proximity to an enzymatic portion of the molecule that acts to cleave the target nucleic acid. Thus, the enzymatic nucleic acid first recognizes and then binds a target nucleic acid through complementary base-pairing, and once bound to the correct site, acts enzymatically to cut the target nucleic acid. Strategic cleavage of such a target nucleic acid will destroy its ability to direct synthesis of an encoded protein. After an enzymatic nucleic acid has bound and cleaved its nucleic acid target, it is released from that nucleic acid to search for another target and can repeatedly bind and cleave new targets.

In a specific embodiment, the subject enzymatic nucleic acid is a ribozyme designed to catalytically cleave an mRNA transcripts to prevent translation of mRNA (see, e.g., PCT International Publication WO90/11364, published Oct. 4, 1990; Sarver et al., 1990, Science 247:1222-1225; and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNAs have the following sequence of two bases: 5'-UG-3'. The construction and production of hammerhead ribozymes is well known in the art and is described more fully in Haseloff and Gerlach, 1988, Nature, 334:585-591. The ribozymes of the present disclosure also include RNA endoribonucleases (hereinafter "Cech-type ribozymes") such as the one which occurs naturally in Tetrahymena thermophila (known as the IVS or L-19 IVS RNA) and which has been extensively described (see, e.g., Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216).

In another specific embodiment, the subject enzymatic nucleic acid is a DNA enzyme. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid. Briefly, to design an ideal DNA enzyme that specifically recognizes and cleaves a target nucleic acid, one of skill in the art must first identify the unique target sequence. Preferably, the unique or substantially sequence is a G/C rich of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms. Methods of making and administering DNA enzymes can be found, for example, in U.S. Pat. No. 6,110,462.

In certain embodiments, the nucleic acid therapeutic agents of the disclosure can be between 12 and 200 nucleotides in length. In one embodiment, exemplary enzymatic nucleic acid compounds of the disclosure are between 15 and 50 nucleotides in length, including, for example, between 25 and 40 nucleotides in length (for example see Jarvis et al., 1996, J. Biol. Chem., 271, 29107-29112). In another embodiment, exemplary antisense molecules of the disclosure are between 15 and 75 nucleotides in length, including, for example, between 20 and 35 nucleotides in length (see for example Woolf et al., 1992, PNAS., 89, 7305-7309; Milner et al., 1997, Nature Biotechnology, 15, 537-541). In another embodiment, exemplary siRNAs of the disclosure are between 20 and 27 nucleotides in length, including, for example, between 21 and 23 nucleotides in length. Those skilled in the art will recognize that all that is required is that the subject nucleic acid therapeutic agent be of length and conformation sufficient and suitable for catalyzing a reaction contemplated herein. The length of the nucleic acid therapeutic agents of the instant disclosure is not limiting within the general limits stated.

V. Nucleic Acid Target Sites

Targets for useful nucleic acid compounds of the disclosure (e.g., antisense nucleic acids, dsRNA, and enzymatic nucleic acid compounds) can be determined as disclosed in Draper et al., 30 WO 93/23569; Sullivan et al., WO 93/23057; Thompson et al., WO 94/02595; Draper et al., WO 95/04818; McSwiggen et al., U.S. Pat. No. 5,525,468. Other examples include the following PCT applications inactivation of expression of disease-related genes: WO 95/23225, WO 95/13380, WO 94/02595. Rather than repeat the guidance provided in those documents here, below are provided specific examples of such methods, not limiting to those in the art.

Enzymatic nucleic acid compounds, siRNA and antisense to such targets are designed as described in those applications and synthesized to be tested in vitro and in vivo, as also described. For examples, the sequence of human GSK3b RNA is screened for optimal nucleic acid target sites using a computer-folding algorithm. Potential nucleic acid binding/cleavage sites are identified. For example, for enzymatic nucleic acid compounds of the disclosure, the nucleic acid compounds are individually analyzed by computer folding (Jaeger et al., 1989 Proc. Natl Acad. Sci. USA, 86, 7706) to assess whether the sequences fold into the appropriate secondary structure. Those nucleic acid compounds with unfavorable intramolecular interactions such as between the binding arms and the catalytic core can be eliminated from consideration.

The subject nucleic acid (e.g., antisense, RNAi, and/or enzymatic nucleic acid compound) binding/cleavage sites are identified and are designed to anneal to various sites in the nucleic acid target (e.g., GSK3b). The binding arms of enzymatic nucleic acid compounds of the disclosure are complementary to the target site sequences described above. Antisense and RNAi sequences are designed to have partial or complete complementarity to the nucleic acid target. The nucleic acid compounds can be chemically synthesized. The method of synthesis used follows the procedure for normal DNA/RNA synthesis as described below and in Usman et al., 1987 J Am. Chem. Soc., 109, 7845; Scaringe et al., 1990 Nucleic Acids Res., 18, 5433; and Wincott et al., 1995 Nucleic Acids Res. 23, 2677-2684; Caruthers et al., 1992, Methods in Enzymology 211,3-19.

Additionally, it is expected that nucleic acid therapeutic agents having a CpG motif are at an increased likelihood of causing a non-specific immune response. Generally, CpG motifs include a CG (Cytosine-Guanosine) sequence adjacent to one or more purines in the 5' direction and one or more pyrimidines in the 3' direction. Lists of known CpG motifs are available in the art. Preferred nucleic acid therapeutics will be selected so as to have a selective effect on the target gene (possibly affecting other closely related genes) without triggering a generalized immune response. By avoiding nucleic acid therapeutics having a CpG motif, it is possible to decrease the likelihood that a particular nucleic acid will trigger an immune response.

VI. Synthesis of Nucleic Acid Therapeutic Agents

Synthesis of nucleic acids greater than 100 nucleotides in length is difficult using automated methods, and the therapeutic cost of such molecules is prohibitive. In this disclosure, small nucleic acid motifs (small refers to nucleic acid motifs less than about 100 nucleotides in length, preferably less than about 80 nucleotides in length, and more preferably less than about 50 nucleotides in length (e.g., antisense oligonucleotides, enzymatic nucleic acids, and RNAi constructs) are preferably used for exogenous delivery. The simple structure of these molecules increases the ability of the nucleic acid to invade targeted regions of RNA structure.

Exemplary molecules of the instant disclosure are chemically synthesized, and others can similarly be synthesized. To illustrate, oligonucleotides (e.g., DNA) are synthesized using protocols known in the art as described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001,311. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer with a 2.5 min coupling step for 2'-O-methylated nucleotides and a 45 sec coupling step for 2'-deoxy nucleotides. Alternatively, syntheses can be performed on a 96-well plate synthesizer, such as the instrument produced by Protogene (Palo Alto, Calif.) with minimal modification to the cycle.

Optionally, the nucleic acid compounds of the present disclosure can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

Preferably, the nucleic acid compounds of the present disclosure are modified extensively to enhance stability by modification with nuclease resistant groups, for example, 2'-amino, 2'-C-allyl, 2'-flouro, 2'-O-methyl, 2'-H (for a review see Usman and Cedergren, 1992, TIBS 17, 34; Usman et al., 1994, Nucleic Acids Symp. Ser. 31, 163). Ribozymes are purified by gel electrophoresis using general methods or are purified by high pressure liquid chromatography (HPLC; See Wincott et al., Supra, the totality of which is hereby incorporated herein by reference) and are re-suspended in water VII. Optimizing Activity of the Nucleic Acid Compounds Nucleic acid compounds with modifications (e.g., base, sugar and/or phosphate) can prevent their degradation by serum ribonucleases and thereby increase their potency. There are several examples in the art describing sugar, base and phosphate modifications that can be introduced into nucleic acid compounds with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid compounds have been extensively described in the art (see Eckstein et al., PCT Publication No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. PCT Publication No. WO 93/15187; Sproat, U.S. Pat. No. 5,334,711 and Beigelman et al., 1995, J. Biol. Chem., 270, 25702; Beigelman et al., PCT publication No. WO 97/26270; Beigelman et al., U.S. Pat. No. 5,716,824; Usman et al., U.S. Pat. No. 5,627,053; Woolf et al., PCT Publication No. WO 98/13526; Thompson et al., U.S. S No. 60/082,404 which was filed on Apr. 20, 1998; Karpeisky et al., 1998, Tetrahedron Lett., 39, 1131; Earnshaw and Gait, 1998, Biopolymers (Nucleic acid Sciences), 48, 39-55; Verma and Eckstein, 1998, Annu. Rev. Biochem., 67, 99-134; and Burlina et al., 1997, Bioorg. Med. Chem., 5, 1999-2010). Similar modifications can be used to modify the nucleic acid compounds of the instant disclosure.

While chemical modification of oligonucleotide internucleotide linkages with phosphorothioate, phosphorothioate, and/or 5'-methylphosphonate linkages improves stability, an over-abundance of these modifications can cause toxicity. Therefore, the amount of these internucleotide linkages should be evaluated and appropriately minimized when designing the nucleic acid compounds. The reduction in the concentration of these linkages should lower toxicity resulting in increased efficacy and higher specificity of these molecules.

In one embodiment, nucleic acid compounds of the disclosure include one or more G-clamp nucleotides. A G-clamp nucleotide is a modified cytosine analog wherein the modifications confer the ability to hydrogen bond both Watson-Crick and Hoogsteen faces of a complementary guanine within a duplex, see for example, Lin and Matteucci, 1998, J. Am. Chem. Soc., 120, 8531-8532. A single G-clamp analog substitution within an oligonucleotide can result in substantially enhanced helical thermal stability and mismatch discrimination when hybridized to complementary oligonucleotides. The inclusion of such nucleotides in nucleic acid compounds of the disclosure results in both enhanced affinity and specificity to nucleic acid targets. In another embodiment, nucleic acid compounds of the disclosure include one or more LNA (locked nucleic acid) nucleotides such as a 2', 4'-C mythylene bicyclo nucleotide (see for example Wengel et al., PCT Publication Nos. WO 00/66604 and WO 99/14226).

In another embodiment, the disclosure features conjugates and/or complexes of nucleic acid compounds targetingGSK3b. Such conjugates and/or complexes can be used to facilitate delivery of nucleic acid compounds into a biological system, such as cells. The conjugates and complexes provided by the instant disclosure can impart therapeutic activity by transferring therapeutic compounds across cellular membranes, altering the pharmacokinetics, and/or modulating the localization of nucleic acid compounds of the disclosure.

The present disclosure encompasses the design and synthesis of novel conjugates and complexes for the delivery of molecules, including, but not limited to, small molecules, lipids, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid compounds of the disclosure into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

The term "biodegradable nucleic acid linker molecule" as used herein, refers to a nucleic acid compound that is designed as a biodegradable linker to connect one molecule to another molecule, for example, a biologically active molecule. The stability of the biodegradable nucleic acid linker molecule can be modulated by using various combinations of ribonucleotides, deoxyribonucleotides, and chemically modified nucleotides, for example, 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid compound, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus based linkage, for example, a phosphoramidate or phosphodiester linkage. The biodegradable nucleic acid linker molecule can also comprise nucleic acid backbone, nucleic acid sugar, or nucleic acid base modifications. The term "biodegradable" as used herein, refers to degradation in a biological system, for example enzymatic degradation or chemical degradation.

Therapeutic nucleic acid compounds, such as the molecules described herein, delivered exogenously are optimally stable within cells until translation of the target RNA has been inhibited long enough to reduce the levels of the undesirable protein. This period of time varies between hours to days depending upon the disease state. These nucleic acid compounds should be resistant to nucleases in order to function as effective intracellular therapeutic agents. Improvements in the chemical synthesis of nucleic acid compounds described in the instant disclosure and in the art have expanded the ability to modify nucleic acid compounds by introducing nucleotide modifications to enhance their nuclease stability as described above.

In another aspect the nucleic acid compounds comprise a 5'and/or a 3'-cap structure. By "cap structure," it is meant chemical modifications, which have been incorporated at either terminus of the oligonucleotide (see for example Wincott et al., WO 97/26270). These terminal modifications protect the nucleic acid compound from exonuclease degradation, and can help in delivery and/or localization within a cell. The cap can be present at the 5'-terminus (5'-cap) or at the 3'-terminus (3'-cap) or can be present on both termninus. In non-limiting examples, the 5'-cap includes inverted abasic residue (moiety), 4', 5'-methylene nucleotide; 1'-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al, PCT publication No. WO 97/26270). In other non-limiting examples, the 3'-cap includes, for example, 4',5'-methylene nucleotide; 1-(bela-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threopentofuranosy nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, Tetrahedron 49, 1925).

VIII. Antibodies

In one embodiment, the application discloses antibodies against GSK3b. These antibodies may be in a polyclonal or monoclonal form and may be immunoreactive with at least one epitope of GSK3b, such as for example, a human GSK3b and/or mouse GSK3b. In certain embodiments, the antibodies may bind to a) a full-length GSK3b polypeptide, or b) a functionally active fragment or derivative thereof.

In one embodiment, antibodies bind a portion of GSK3b. In certain embodiments, antibodies bind the phosphorylation cite of serine-9. In certain embodiments, antibodies bind the phosphorylation cite of tyrosine-216. In certain embodiments, antibodies bind the kinase domain.

In some embodiments, the anti-GSK3b antibody binds to a GSK3b polypeptide with a $K_D$ of $1 \times 10^{-6}$ M or less. In still other embodiments, the antibody binds to a GSK3b polypeptide with a $K_D$ of $1 \times 10^{-7}$ M, $3 \times 10^{-8}$ M, $2 \times 10^{-9}$ M, $1 \times 10^{-10}$ M, $1 \times 10^{-11}$ M, or $5 \times 10^{-12}$ M or less.

The anti-GSK3b antibodies of the present application include antibodies having all types of constant regions, including IgM, IgG, IgD, IgA and IgE, and any isotype, including IgG 1, IgG2a, IgG2b, IgG3 and IgG4. The light chains of the antibodies can either be kappa light chains or lambda light chains.

In another aspect, the antibodies of the present application modulate at least one, or all, biological activities of GSK3b. The biological activities of GSK3b include: 1) signaling transduction activities, such as kinase activity; and 2) cellular responses induced by GSK3b, such as inflammatory activities.

In certain embodiments, the antibodies of the present application may have at least one activity selected from the group consisting of: 1) inhibiting kidney inflammation; 2) inhibiting kidney disease; 3) acting as a diagnostic or prognostic marker.

In one embodiment, the antibodies inhibit kidney inflammation in vivo (such as in a subject), such as for example, by at least 10%, 25%, 50%, 75%, or 90%.

In another embodiment, the antibodies inhibit kidney disease symptoms, such as for example, by at least 10%, 25%, 50%, 75%, or 90%.

The present application provides for the polynucleotide molecules encoding the antibodies and antibody fragments and their analogs described herein. Because of the degeneracy of the genetic code, a variety of nucleic acid sequences encode each antibody amino acid sequence. The desired nucleic acid sequences can be produced by de novo solid-phase DNA synthesis or by PCR mutagenesis of an earlier prepared variant of the desired polynucleotide. In one embodiment, the codons that are used comprise those that are typical for human or mouse (see, e.g., Nakamura, Y., Nucleic Acids Res. 28: 292 (2000)).

The present application includes the monoclonal antibodies that bind to substantially the same epitope as any one of the exemplified antibodies. Two antibodies are said to bind to substantially the same epitope of a protein if amino acid mutations in the protein that reduce or eliminate binding of one antibody also reduce or eliminate binding of the other antibody, and/or if the antibodies compete for binding to the protein, i.e., binding of one antibody to the protein reduces or eliminates binding of the other antibody. The determination of whether two antibodies bind substantially to the same epitope is accomplished by the methods known in the art, such as a competition assay. In conducting an antibody competition study between a control antibody (for example, one of the anti-GSK3b antibodies described herein) and any test antibody, one may first label the control antibody with a detectable label, such as, biotin, enzymatic, radioactive label, or fluorescence label to enable the subsequent identification. An antibody that binds to substantially the same epitope as the control antibody should be able to compete for binding and thus should reduce control antibody binding, as evidenced by a reduction in bound label.

The polyclonal forms of the anti-GSK3b antibodies are also included in the present application. In certain embodiments, these antibodies modulate at least one activity of GSK3b, or bind to the GSK3b epitopes as the described monoclonal antibodies in the present application. Polyclonal antibodies can be produced by the method described herein.

Antibodies against GSK3b of all species of origins are included in the present application. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal. In one embodiment, the antibody is an isolated monoclonal antibody that binds to and/or neutralizes GSK3b.

Recombinant antibodies against GSK3b are also included in the present application. These recombinant antibodies have the same amino acid sequence as the natural antibodies or have altered amino acid sequences of the natural antibodies in the present application. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety).

Antibodies can be engineered in numerous ways. They can be made as single-chain antibodies (including small modular immunopharmaceuticals or SMIPS™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

Antibodies with engineered or variant constant or Fc regions can be useful in modulating effector functions, such as, for example, antigen-dependent cytotoxicity (ADCC) and complement-dependent cytotoxicity (CDC). Such antibodies with engineered or variant constant or Fc regions may be useful in instances where GSK3b is expressed in normal tissue, for example; variant anti-GSK3b antibodies without effector function in these instances may elicit the desired therapeutic response while not damaging normal tissue.

Accordingly, certain aspects and methods of the present disclosure relate to anti-GSK3b antibodies with altered effector functions that comprise one or more amino acid substitutions, insertions, and/or deletions. In certain embodiments, such a variant anti-GSK3b antibody exhibits reduced or no effector function. In particular embodiments, a variant antibody comprises a G2/G4 construct in place of the G1 domain (see Mueller et al. Mol Immunol. 1997 Apr;34(6):441-52).

In addition to swapping the G1 domain with a G2/G4 construct as presented herein, anti-GSK3b antibodies with reduced effector function may be produced by introducing other types of changes in the amino acid sequence of certain regions of the antibody. Such amino acid sequence changes include but are not limited to the Ala-Ala mutation described by Bluestone et al. (see WO 94/28027 and WO 98/47531; also see Xu et al. 2000 Cell Immunol 200; 16-26). Thus in certain embodiments, anti-GSK3b antibodies with mutations within the constant region including the Ala-Ala mutation may be used to reduce or abolish effector function. According to these embodiments, the constant region of an anti-GSK3b antibody comprises a mutation to an alanine at position 234 or a mutation to an alanine at position 235. Additionally, the constant region may contain a double mutation: a mutation to an alanine at position 234 and a second mutation to an alanine at position 235. In one embodiment, the anti-GSK3b antibody comprises an IgG4 framework, wherein the Ala-Ala mutation would describe a mutation(s) from phenylalanine to alanine at position 234 and/or a mutation from leucine to alanine at position 235. In another embodiment, the anti-GSK3b antibody comprises an IgG1 framework, wherein the Ala-Ala mutation would describe a mutation(s) from leucine to alanine at position 234 and/or a mutation from leucine to alanine at position 235. An anti-GSK3b antibody may alternatively or additionally carry other mutations, including the point mutation K322A in the CH2 domain (Hezareh et al. 2001 J Virol. 75: 12161-8). An antibody with said mutation(s) in the constant region may furthermore be a blocking or non-blocking antibody.

Changes within the hinge region also affect effector functions. For example, deletion of the hinge region may reduce affinity for Fc receptors and may reduce complement activation (Klein et al. 1981 Proc Natl Acad Sci USA. 78: 524-528). The present disclosure therefore also relates to antibodies with alterations in the hinge region.

In particular embodiments, anti-GSK3b antibodies may be modified to either enhance or inhibit complement dependent cytotoxicity (CDC). Modulated CDC activity may be achieved by introducing one or more amino acid substitutions, insertions, or deletions in an Fc region of the antibody (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., J. Exp Med. 176:1191-1195 (1992) and Shopes, B. J. Immunol. 148:2918-2922 (1992), WO99/51642, Duncan & Winter Nature 322: 738-40 (1988); U.S. Pat. No. 5,648,260; U.S. Pat. No. 5,624,821; and WO94/29351. Homodimeric antibodies with enhanced activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

Another potential means of modulating effector function of antibodies includes changes in glycosylation. This topic has been recently reviewed by Raju who summarized the proposed importance of the oligosaccharides found on human IgGs with their degree of effector function (Raju, TS. BioProcess *International* April 2003. 44-53). According to Wright and Morrison, the microheterogeneity of human IgG oligosaccharides can affect biological functions such as CDC and ADCC, binding to various Fc receptors, and binding to C1q protein (Wright A. & Morrison SL. TIBTECH 1997, 15: 26-32). It is well documented that glycosylation patterns of antibodies can differ depending on the producing cell and the cell culture conditions (Raju, TS. BioProcess *International* April 2003. 44-53). Such differences can lead to changes in both effector function and pharmacokinetics (Israel et al. *Immunology*. 1996; 89(4):573-578; Newkirk et al. *P. Clin. Exp.* 1996; 106(2):259-64). Differences in effector function may be related to the IgGs ability to bind to the Fcγ receptors (FcγRs) on the effector cells. Shields, et al., have shown that IgG, with variants in amino acid sequence that have improved binding to FcγR, can exhibit up to 100% enhanced ADCC using human effector cells (Shields et al. *J Biol Chem*. 2001 276(9):6591-604). While these variants include changes in amino acids not found at the binding interface, both the nature of the sugar component as well as its structural pattern may also contribute to the differences observed. In addition, the presence or absence of fucose in the oligosaccharide component of an IgG can improve binding and ADCC (Shields et al. *J Biol Chem*. 2002; 277(30):26733-40). An IgG that lacked a fucosylated carbohydrate linked to $Asn^{297}$ exhibited normal receptor binding to the Fcγ receptor. In contrast, binding to the FcγRIIA receptor was improved 50% and accompanied by enhanced ADCC, especially at lower antibody concentrations.

Work by Shinkawa, et al., demonstrated that an antibody to the human IL-5 receptor produced in a rat hybridoma showed more than 50% higher ADCC when compared to the antibody produced in Chinese hamster ovary cells (CHO) (Shinkawa et al. *J Biol Chem*. 2003 278(5):3466-73). Monosaccharide composition and oligosaccharide profiling showed that the rat hybridoma-produced IgG had a lower content of fucose than the CHO-produced protein. The authors concluded that the lack of fucosylation of an IgG1 has a critical role in enhancement of ADCC activity.

A different approach was taken by Umana, et al., who changed the glycosylation pattern of chCE7, a chimeric IgG1 anti-neuroblastoma antibody (Umana et al. *Nat Biotechnol.* 1999 Feb; 17(2): 176-80). Using tetracycline, they regulated the activity of a glycosyltransferase enzyme (GnnII) which bisects oligosaccharides that have been implicated in ADCC activity. The ADCC activity of the parent antibody was barely above background level. Measurement of ADCC activity of the chCE7 produced at different tetracycline levels showed an optimal range of GnTIH expression for maximal chCE7 in vitro ADCC activity. This activity correlated with the level of constant region-associated, bisected complex oligosaccharide. Newly optimized variants exhibited substantial ADCC activity. Similarly, Wright and Morrison produced antibodies in a CHO cell line deficient in glycosylation (1994 J Exp Med 180: 1087-1096) and showed that antibodies produced in this cell line were incapable of complement-mediated cytolysis. Thus as known alterations that affect effector function include modifications in the glycosylation pattern or a change in the number of glycosylated residues, the present disclosure relates to a GSK3b antibody wherein glycosylation is altered to either enhance or decrease effector function(s) including ADCC and CDC. Altered glycosylation includes a decrease or increase in the number of glycosylated residues as well as a change in the pattern or location of glycosylated residues.

Still other approaches exist for the altering effector function of antibodies. For example, antibody-producing cells can be hypermutagenic, thereby generating antibodies with randomly altered nucleotide and polypeptide residues throughout an entire antibody molecule (see WO 2005/011735). Hypermutagenic host cells include cells deficient in DNA mismatch repair. Antibodies produced in this manner may be less antigenic and/or have beneficial pharmacokinetic properties. Additionally, such antibodies may be selected for properties such as enhanced or decreased effector function(s).

It is further understood that effector function may vary according to the binding affinity of the antibody. For example, antibodies with high affinity may be more efficient in activating the complement system compared to antibodies with relatively lower affinity (Marzocchi-Machado et al. 1999 Immunol Invest 28: 89-101). Accordingly, an antibody may be altered such that the binding affinity for its antigen is reduced (e.g., by changing the variable regions of the antibody by methods such as substitution, addition, or deletion of one or more amino acid residues). An anti-GSK3b antibody with reduced binding affinity may exhibit reduced effector functions, including, for example, reduced ADCC and/or CDC.

In certain embodiments, GSK3b antibodies utilized in the present disclosure are especially indicated for diagnostic and therapeutic applications as described herein. Accordingly, GSK3b antibodies may be used in therapies, including combination therapies, in the diagnosis and prognosis of disease, as well as in the monitoring of disease progression.

In the therapeutic embodiments of the present disclosure, bispecific antibodies are contemplated. Bispecific antibodies may be monoclonal, human or humanized antibodies that have binding specificities for at least two different antigens. In the present case, one of the binding specificities is for the GSK3b antigen on a cell, the other one is for any other antigen, such as for example, a cell-surface protein or receptor or receptor subunit.

The genetically altered anti-GSK3b antibodies should be functionally equivalent to the above-mentioned natural antibodies. In certain embodiments, modified antibodies provide improved stability or/and therapeutic efficacy. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this application can be modified post-translationally (e.g., acetylation, and/or phosphorylation) or can be modified synthetically (e.g., the attachment of a labeling group). In certain embodiments, genetically altered antibodies are chimeric antibodies and humanized antibodies.

The chimeric antibody is an antibody having a variable region and a constant region derived from two different antibodies, such as for example, derived from separate species. In certain embodiments, the variable region of the chimeric antibody is derived from murine and the constant region is derived from human.

The genetically altered antibodies used in the present application include humanized antibodies that bind to and modulate GSK3b activity. In one embodiment, said humanized antibody comprising CDRs of a mouse donor immunoglobulin and heavy chain and light chain frameworks and constant regions of a human acceptor immunoglobulin. The method of making humanized antibody is disclosed in U.S. Pat. Nos: 5,530,101; 5,585,089; 5,693,761; 5,693,762; and 6,180,370 each of which is incorporated herein by reference in its entirety.

Anti-GSK3b fully human antibodies are also included in the present application. In one embodiment of the present application, said fully human antibodies modulate the activities of GSK3b described herein.

Fragments of the anti-GSK3b antibodies, which retain the binding specificity to GSK3b, are also included in the present application. Examples of these antigen-binding fragments include, but are not limited to, partial or full heavy chains or light chains, variable regions, or CDR regions of any anti-GSK3b antibodies described herein.

In one embodiment of the application, the antibody fragments are truncated chains (truncated at the carboxyl end). In certain embodiments, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dab fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemical techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining VL- and VH-coding regions with a DNA that encodes a peptide linker connecting the VL and VH protein fragments This application provides fragments of anti-GSK3b antibodies, which may comprise a portion of an intact antibody, such as for example, the antigen-binding or variable region of the intact antibody. Examples of antibody fragments include Fab, Fab', F(ab')$_2$, and Fv fragments; diabodies; linear antibodies (Zapata et al., *Protein Eng.* 1995; 8(10): 1057-1062); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment of an antibody yields an F(ab')$_2$ fragment that has two antigen-combining sites and is still capable of cross-linking antigen.

"Fv" usually refers to the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the CDRs confer antigen-binding specificity to the antibody. However, even a single variable domain (or half of an Fv comprising three CDRs specific for an antigen) has the ability to recognize and bind antigen, although likely at a lower affinity than the entire binding site.

Thus, in certain embodiments, the antibodies of the application may comprise 1, 2, 3, 4, 5, 6, or more CDRs that recognize GSK3b.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. In certain embodiments, the Fv polypeptide further comprises a polypeptide linker between the $V_H$ and $V_L$ domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

SMIPs are a class of single-chain peptides engineered to include a target binding region and effector domain (CH2 and CH3 domains). See, e.g., U.S. Patent Application Publication No. 20050238646. The target binding region may be derived from the variable region or CDRs of an antibody, e.g., an anti-GSK3b antibody of the application. Alternatively, the target binding region is derived from a protein that binds GSK3b.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

An "isolated" antibody is one that has been identified and separated and/or recovered from a component of its natural environment. Contaminating components of its natural environment are materials that would interfere with diagnostic or therapeutic uses for the antibody, and may include enzymes, hormones, and other proteinaceous or nonproteinaceous solutes. In specific embodiments, the antibody will be purified to greater than 95% by weight of antibody as determined by the Lowry method, or greater than 99% by weight, to a degree that complies with applicable regulatory requirements for administration to human patients (e.g., substantially pyrogen-free), to a degree sufficient to obtain at least 15 residues of N-terminal or internal amino acid sequence by use of a spinning cup sequenator, or to homogeneity by SDS-PAGE under reducing or nonreducing conditions using Coomassie blue or, such as for example, silver stain. Isolated antibody includes the antibody in situ within recombinant cells, since at least one component of the antibody's natural environment will not be present. Ordinarily, however, isolated antibody will be prepared by at least one purification step, for example, an affinity chromatography step, an ion (anion or cation) exchange chromatography step, or a hydrophobic interaction chromatography step.

It is well known that the binding to a molecule (or a pathogen) of antibodies with an Fc region assists in the processing and clearance of the molecule (or pathogen). The Fc portions of antibodies are recognized by specialized receptors expressed by immune effector cells. The Fc portions of IgG1 and IgG3 antibodies are recognized by Fc receptors present on the surface of phagocytic cells such as macrophages and neutrophils, which can thereby bind and engulf the molecules or pathogens coated with antibodies of these isotypes (Janeway et al., Immunobiology 5th edition, page 147, Garland Publishing (New York, 2001)).

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; U.S. Pat. No. 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology, 10: 1455-1460 (1992), regarding primatized antibody. See, e.g., Ladner et al., U.S. Pat. No. 4,946,778; and Bird et al., Science, 242: 423-426 (1988)), regarding single chain antibodies.

In addition, functional fragments of antibodies, including fragments of chimeric, humanized, primatized or single chain antibodies, can also be produced. Functional fragments of the subject antibodies retain at least one binding function and/or modulation function of the full-length antibody from which they are derived. In certain embodiments, functional fragments retain an antigen-binding function of a corresponding full-length antibody (such as for example, ability of anti-GSK3b antibody to bind GSK3b).

Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated by reference in its entirety) to produce fusion proteins or conjugates having novel properties.

Antibodies against the ligands of GSK3b are also encompassed in the present application. These antibodies are natural antibodies, recombinant antibodies, humanized antibodies, chimeric antibodies, the fully human antibodies, antibody fragments and conjugates. In certain embodiments, these antibodies are capable of modulating the biological activities of the GSK3b ligand-receptor pairs. These modulating antibodies may inhibit or activate GSK3b activity. These antibodies can be made in the similar fashion as the making of the anti-GSK3b antibodies, and the fragments and conjugates thereof described herein.

IX. Small Molecules

The inhibitors of the present application also include small molecules, which may inhibit the activity of proteins with enzymatic function, and/or the interactions of said proteins. Chemical agents, referred to in the art as "small molecule" compounds are typically organic, non-peptide molecules, having a molecular weight less than 10,000, less than 5,000, less than 1,000, or less than 500 daltons. This class of inhibitors includes chemically synthesized molecules, for instance, compounds from combinatorial chemical libraries. Synthetic compounds may be rationally designed or identified based on known or inferred properties of the GSK3b protein or may be identified by screening compound libraries. Alternative appropriate inhibitors of this class are natural products, particularly secondary metabolites from organisms such as plants or fungi, which can also be identified by screening compound libraries for GSK3b-inhibiting activity. Methods for generating and obtaining compounds are well known in the art (Schreiber S L, Science 151: 1964-1969(2000); Radmann J. and Gunther J., Science 151: 1947-1948 (2000)). In certain embodiment, small molecules bind a portion of GSK3b. In certain embodiments, small molecules bind the phosphorylation cite of serine-9. In certain embodiments, small molecules bind the phosphorylation cite of tyrosine-216. In certain embodiments, small molecules bind the kinase domain.

In certain embodiments, the methods of the application may use known GSK3b inhibitors. Lithium (Lithium chloride) is a known inhibitor of GSK3b; however potential toxicities may limit its utility. Valproic acid, another selective GSK3b inhibitor has been used to suppress seizures, and has a more attractive side effect profile. Other GSK3b inhibitors include TDZD-8 (commercially available from A. G. Scientific, Inc., San Diego, Calif. ) have a high selectivity for GSK3b kinase and less potential to exhaust ATP compared to valproic acid. The maleimide class of GSK3b inhibitors include SB216763 and SB415286 (SmithKline Beecham). Thienyl and pheyl alpha-halomethyl ketones are also useful as inhibitors. Yet others include azakenpaullone (e.g., 1-azakenpaullone), bis-7-azaindoylylmaleimide, AR A014418, CHIR98014, and CHIR 990021 (the latter of which are available from Chiron). Structures of these and other known GSK3b inhibitors are known in the art, e.g., Cohen et al., 2004, Nature Reviews 3:479-487, hereby incorporated by reference). Other inhibitors are commercially available, e.g., 1-Azakenpaullone, Alsterpaullone, 2-Cyanoethyl, Alsterpaullone, FRATtide, GSK-3b Inhibitor VII, GSK-3b Inhibitor XI, GSK-3b Inhibitor I, GSK-3b Inhibitor II, GSK-3b Inhibitor III, GSK-3 Inhibitor IX, InSolution™ GSK-3 Inhibitor IX, GSK-3 Inhibitor X, GSK-3 Inhibitor XIII, GSK-3 Inhibitor XIV, Control, MeBIO, GSK-3b Inhibitor VI, InSolution™ GSK-3b Inhibitor VIII, GSK-3b Inhibitor XII, TWS 119, GSK-3b Inhibitor VIII, GSK-3b Peptide Inhibitor, Cell-permeable, Indirubin-3'-monoxime, and Kenpaullone (Calbiochem).

X Diagnostic Methods

GSK3b is a valid, sensitive, and specific biomarker for identifying patients with kidney disease at early stages so that timely treatment is rendered to slow, inhibit, or stop progression to end state renal disease.

In the kidney GSK3b expression is low under normal conditions and markedly elevated in human kidney disease and diverse models of kidney disease including remnant kidney disease, inflammatory kidney disease, acute kidney injury or infection such as repeated kidney infections, or a chronic condition, e.g., diabetes or hypertension, that may lead to chronic kidney disease, glomerulonephritis, glomerulosclerosis, diabetic nephropathy, polycystic kidney disease, hypokalemic nephropathy, oxalate nephropathy, a congenital kidney pathology, Lupus nephropathy or other diseases that affect the body's immune system, and obstructions such as kidney stones, tumors or an enlarged prostate gland. The level of GSK3b was found to be highly correlated with the magnitude or severity of renal inflammation.

Current biomarkers for renal injuries, e.g., serum creatinine, urine protein levels and morphology of renal biopsy, are relatively insensitive and of little prognostic value at early stage renal disease. GSK3b is rapidly and significantly induced in kidney following injury, and an increase in GSK3b level is a sensitive and early indication of renal disease.

The data described herein demonstrates that significantly higher levels of GSK3b indicate a condition of renal inflammation or injury. GSK3b protein may be detected using antibody-based assays, e.g., Western blot assays or ELISA. A normal value range of GSK3b levels in normal individuals (e.g., healthy volunteers) is determined as a baseline or control value or range. Collection of normal baseline data is carried out using conventional analytical techniques and well-known methods of statistical analysis. A "normal level" of GSK3b is a mean level of GSK3b protein, transcript, or enzyme activity in a given bodily fluid for a population of healthy individuals. A normal range is a spectrum of values among a population of healthy individuals, plus or minus 10% of the mean, or plus or minus two standard deviations from the mean. Normal ranges are preferably age-matched.

Methods of detecting the level of GSK3b in bodily fluids include contacting a component of a bodily fluid with a GSK3b-specific antibody bound to solid matrix, e.g., microtiter plate, bead, dipstick. For example, the solid matrix is dipped into a patient-derived sample of a bodily fluid, washed, and the solid matrix contacted with a reagent to detect the presence of immune complexes present on the solid matrix. Proteins in a test sample are immobilized on (bound to) a solid matrix. Methods and means for covalently or noncovalently binding proteins to solid matrices are known in the art. The nature of the solid surface may vary depending upon the assay format. For assays carried out in microtiter wells, the solid surface is the wall of the well or cup. For assays using beads, the solid surface is the surface of the bead. In assays using a dipstick (i.e., a solid body made from a porous or fibrous material such as fabric or paper) the surface is the surface of the material from which the dipstick is made. Examples of useful solid supports include nitrocellulose (e.g., in membrane or microtiter well form), polyvinyl chloride (e.g., in sheets or microtiter wells), polystyrene latex (e.g., in beads or microtiter plates, polyvinylidine fluoride (known as IMMULON™.), diazotized paper, nylon membranes, activated beads, and Protein A beads. Microtiter plates may be activated (e.g., chemically treated or coated) to covalently bind proteins. The solid support containing the antibody is typically washed after contacting it with the test sample, and prior to detection of bound immune complexes.

A common feature of all of these assays is that a GSK3b-specific binding moiety is contacted with a sample of bodily fluid under conditions that permit GSK3b to bind to the antibody forming an immune complex containing the patient GSK3b bound to a GSK3b-specific antibody. Such conditions are typically physiologic temperature, pH, and ionic strength. The incubation of the antibody with the test sample is followed by detection of immune complexes by a detectable label. For example, the label is enzymatic, fluorescent, chemiluminescent, radioactive, or a dye. Assays which amplify the signals from the immune complex are also known in the art, e.g., assays which utilize biotin and avidin.

Antibodies and nucleic acid compositions disclosed herein are useful in diagnostic and prognostic evaluation of kidney diseases and inflammation, associated with GSK3b expression.

Methods of diagnosis can be performed in vitro using a cellular sample (e.g., blood serum, plasma, urine, saliva, cerebral spinal fluid, joint fluid, fluid from the pleural space, peritoneal fluid, lymph node biopsy or tissue) from a patient or can be performed by in vivo imaging. In certain embodiments, samples may comprise resident kidney cells, infiltrating cells, or circulating cells. In certain embodiments, cells expressing GSK3b may comprise resident kidney cells, infiltrating cells, or circulating cells. In certain embodiments, resident kidney cells may be shed into a bodily fluid such as the urine.

In particular embodiments, the present application provides an antibody conjugate wherein the antibodies of the present application are conjugated to a diagnostic imaging agent. Compositions comprising the antibodies of the present application can be used to detect GSK3b, for example, by radioimmunoassay, ELISA, FACS, etc. One or more detectable labels can be attached to the antibodies. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

In certain embodiments, measurement of GSK level and activity in tissue samples is carried out as follows. Total expression of GSK3b, is measured by western immunoblot in kidney homogenates using a commercially available mouse monoclonal antibody against rat GSK3b (Santa Cruz Biotechology). Densitometric analysis of immunoblot bands is used to compare protein abundance of GSK3b in remnant kidneys and controls at each time point.

Regulation of GSK3b kinase activity is a process that occurs at multiple levels, including post-translational phosphorylation, interaction with other proteins, substrate priming and intracellular distribution. Due to its action to phosporylate glycogen synthase, overall activity of GSK3b is measured by a simple biochemical assay. GSK3b from tissue homogenates is immunoprecipitated by anti-GSK3b antibody and protein G Sepharose. Immunoprecipitates from diseased kidneys or control kidneys are washed and incubated with phospho-glycogen synthase peptide 2 (Upstate, Chicago, Ill.) and [$^{32}$P] ATP. The reaction is terminated by adding SDS lysis buffer and heating at 70° C. The reaction mixture is centrifuged, and equal amounts of the supernatant spotted onto phosphocellulose paper. Free [$^{32}$P] ATP is washed away from the filter paper and [$^{32}$P] incorporation measured by scintillation counting. Unphosphorylated glycogen synthase (Upstate) is used as negative control; non-specific [$^{32}$P] incorporation is subtracted from values obtained using the phospho-glycogen synthase peptide.

In certain embodiments, tissue sections are stained or the tissue is disrupted, e.g., homogenized, and processed as for a fluid. GSK3b and inactive GSK3b (i.e. phospho-Ser 9 GSK3b) is quantified by methods known in the art, e.g., immunoblot analysis followed by densitometry or immunohistochemistry staining and quantitative scoring of GSK3b and p-Serine 9 GSK3b in the sections. The ratio of inactive phospho-Serine 9 GSK3b to total GSK3b is calculated and compared. GSK3b inhibitors suppress GSK3b activity via inhibitory phosphorylation at the serine 9 amino acid residue.

A radiolabeled antibody in accordance with this disclosure can be used for in vitro diagnostic tests. The specific activity of an antibody, binding portion thereof, probe, or ligand, depends upon the half-life, the isotopic purity of the radioactive label, and how the label is incorporated into the biological agent. In immunoassay tests, the higher the specific activity, in general, the better the sensitivity. Radioisotopes useful as labels, e.g., for use in diagnostics, include iodine ($^{131}$I or $^{125}$I), indium ($^{111}$In), technetium ($^{99}$Tc), phosphorus ($^{32}$P), carbon ($^{14}$C), and tritium ($^{3}$H), or one of the therapeutic isotopes listed above.

The radiolabeled antibody can be administered to a patient where it is localized to kidney cells bearing the antigen with which the antibody reacts, and is detected or "imaged" in vivo using known techniques such as radionuclear scanning using e.g., a gamma camera or emission tomography. See e.g., Bradwell et al., "Developments in Antibody Imaging", Monoclonal Antibodies for Cancer Detection and Therapy, Baldwin et al., (eds.), pp. 65-85 (Academic Press 1985), which is hereby incorporated by reference. Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

Fluorophore and chromophore labeled biological agents can be prepared from standard moieties known in the art. Since antibodies and other proteins absorb light having wavelengths up to about 310 nm, the fluorescent moieties may be selected to have substantial absorption at wavelengths above 310 nm, such as for example, above 400 nm. A variety of suitable fluorescers and chromophores are described by Stryer, Science, 162:526 (1968) and Brand et al., Annual Review of Biochemistry, 41:843-868 (1972), which are hereby incorporated by reference. The antibodies can be labeled with fluorescent chromophore groups by conventional procedures such as those disclosed in U.S. Pat. Nos. 3,940,475, 4,289,747, and 4,376,110, which are hereby incorporated by reference.

In certain embodiments, antibody conjugates or nucleic acid compositions for diagnostic use in the present application are intended for use in vitro, where the composition is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. In certain embodiments, secondary binding ligands are biotin and avidin or streptavidin compounds.

In certain embodiments the diagnostic methods of the application may be used in combination with other kidney disease or inflammation diagnostic tests.

In certain embodiments, the effects on inflammation, formalin fixed and paraffin embedded tissue sections undergo immunohistochemistry staining for CD45 to label infiltrating inflammatory cells. The magnitude of inflammation is quantified by absolute counting of CD45 positive cells in each section and by western immunoblot analysis for CD45 normalized by the invariant b-actin. The densitometric values of CD45 bands quantitatively represent the extent of inflammation. Assessment of tubulo-interstitial and glomerular injury and fibrosis also provide a reference for disease assessment. Suppression of inflammation is associated with reductions in tubulo-interstitial injury and fibrosis. Detection of inflammatory mediators and cytokines is also used to assess inflammation.

In certain embodiments, NF-kB p65 phosphorylation is assessed as follows. Cell lysates with equal amounts of total protein are immunoblotted for phosphorylated NF-kB p65 or total p65. Anti-phosphorylated NF-kB p65 antibody is commercially available, e.g., from Cell Signaling, MA. Densitometric results of phosphorylated NF-kB p65 and total p65 bands as well as the ratio of pp65/p65 are compared between different transfections at different time points.

In certain embodiments, IkB phosphorylation and degradation is evaluated as follows. Cell lysates with equal amounts of total protein are immunoblotted for phosphorylated IkBa (anti-phosphorylated IkBa antibody is available from Cell Signaling. MA) or total IkBa. Densitometric results of phosphorylated IkBa and total IkBa bands are compared across the different treatments and time points.

The present application also provides for a diagnostic kit comprising anti-GSK3b antibodies or nucleic acid compositions that bind GSK3b. Such a diagnostic kit may further comprise a packaged combination of reagents in predetermined amounts with instructions for performing the diagnostic assay. Where the antibody is labeled with an enzyme, the kit will include substrates and co-factors required by the enzyme. In addition, other additives may be included such as stabilizers, buffers and the like. The relative amounts of the various reagents may be varied widely to provide for concentrations in solution of the reagents that substantially optimize the sensitivity of the assay. Particularly, the reagents may be provided as dry powders, usually lyophilized, including excipients that, on dissolution, will provide a reagent solution having the appropriate concentration.

In another aspect, the present application concerns immunoassays for binding, purifying, quantifying and otherwise generally detecting GSK3b protein components. As detailed below, immunoassays, in their most simple and direct sense, are binding assays. In certain embodiments, immunoassays are the various types of enzyme linked immunoadsorbent assays (ELISAs) and radioimmunoassays (RIA) known in the art. Immunohistochemical detection using tissue sections is also particularly useful. However, it will be readily appreciated that detection is not limited to such techniques, and Western blotting, dot and slot blotting, FACS analyses, and the like may also be used.

The steps of various useful immunoassays have been described in the scientific literature, such as, e.g., Nakamura et al., in Enzyme Immunoassays: Heterogeneous and Homogeneous Systems, Chapter 27 (1987), incorporated herein by reference.

In general, the immunobinding methods include obtaining a sample suspected of containing a protein or peptide, in this case, GSK3b and contacting the sample with a first antibody immunoreactive with GSK3b under conditions effective to allow the formation of immunocomplexes.

Immunobinding methods include methods for purifying GSK3b proteins, as may be employed in purifying protein from patients' samples or for purifying recombinantly expressed protein. They also include methods for detecting or quantifying the amount of GSK3b in a tissue sample, which requires the detection or quantification of any immune complexes formed during the binding process.

The biological sample analyzed may be any sample that is suspected of containing GSK3b such as a homogenized kidney tissue sample. Contacting the chosen biological sample with the antibody under conditions effective and for a period of time sufficient to allow the formation of primary immune complexes) is generally a matter of adding the antibody composition to the sample and incubating the mixture for a period of time long enough for the antibodies to form immune complexes with, i.e., to bind to, any GSK3b present. The sample-antibody composition is washed extensively to remove any non-specifically bound antibody species, allowing only those antibodies specifically bound within the primary immune complexes to be detected.

In general, the detection of immunocomplex formation is well known in the art and may be achieved through the application of numerous approaches. These methods are based upon the detection of radioactive, fluorescent, biological or enzymatic tags. Of course, one may find additional advantages through the use of a secondary binding ligand such as a second antibody or a biotin/avidin ligand binding arrangement, as is known in the art.

The anti-GSK3b antibody used in the detection may itself be conjugated to a detectable label, wherein one would then simply detect this label. The amount of the primary immune complexes in the composition would, thereby, be determined.

Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are washed extensively to remove any non-specifically bound labeled secondary antibodies or ligands, and the remaining label in the secondary immune complex is detected.

An enzyme linked immunoadsorbent assay (ELISA) is a type of binding assay. In one type of ELISA, anti-GSK3b antibodies used in the diagnostic method of this application are immobilized onto a selected surface exhibiting protein affinity, such as a well in a polystyrene microtiter plate. Then, a suspected neoplastic tissue sample is added to the wells. After binding and washing to remove non-specifically bound immune complexes, the bound GSK3b may be detected. Detection is generally achieved by the addition of another anti-GSK3b antibody that is linked to a detectable label. This type of ELISA is a simple "sandwich ELISA." Detection may also be achieved by the addition of a second anti-GSK3b antibody, followed by the addition of a third antibody that has binding affinity for the second antibody, with the third antibody being linked to a detectable label.

In another type of ELISA, the kidney tissue samples are immobilized onto the well surface and then contacted with the anti-GSK3b antibodies used in this application. After binding and washing to remove non-specifically bound immune complexes, the bound anti-GSK3b antibodies are detected. Where the initial anti-GSK3b antibodies are linked to a detectable label, the immune complexes may be detected directly. Alternatively, the immune complexes may be detected using a second antibody that has binding affinity for the first anti-GSK3b antibody, with the second antibody being linked to a detectable label.

Irrespective of the format employed, ELISAs have certain features in common, such as coating, incubating or binding, washing to remove non-specifically bound species, and detecting the bound immune complexes.

The radioimmunoassay (RIA) is an analytical technique which depends on the competition (affinity) of an antigen for antigen-binding sites on antibody molecules. Standard curves are constructed from data gathered from a series of samples each containing the same known concentration of labeled antigen, and various, but known, concentrations of unlabeled antigen. Antigens are labeled with a radioactive isotope tracer. The mixture is incubated in contact with an antibody. Then the free antigen is separated from the antibody and the antigen bound thereto. Then, by use of a suitable detector, such as a gamma or beta radiation detector, the percent of either the bound or free labeled antigen or both is determined. This procedure is repeated for a number of samples containing various known concentrations of unlabeled antigens and the results are plotted as a standard graph. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In an analysis, the sample in which the concentration of antigen is to be determined is mixed with a known amount of tracer antigen. Tracer antigen is the same antigen known to be in the sample but which has been labeled with a suitable radioactive isotope. The sample with tracer is then incubated in contact with the antibody. Then it can be counted in a suitable detector which counts the free antigen remaining in the sample. The antigen bound to the antibody or immunoadsorbent may also be similarly counted. Then, from the standard curve, the concentration of antigen in the original sample is determined.

In certain embodiments, immunocytochemical techniques are used as follows. Cells or tissue sections are processed for labeling. For example, cells are plated on chamber slides for 24 h, then serum deprived for another 24 h. Cells are rinsed with PBS and fixed in 4% paraformadehyde for 20 min. Cells are then treated with 1% Triton X-100 for 10 min. followed by incubation with preimmune serum in PBS to block non-specific binding. Primary antibodies are diluted in 3% normal donkey serum and incubated with cells for 1 h. Finally fluorescent labeled secondary antibodies are applied for 30 min. Slides are examined by fluorescence microscopy.

In certain embodiments, Enzyme-linked Immunosorbent assay (ELISA) is used to evaluate GSK3b proten level. For example, rat kidneys were homogenized in RIPA [1% Nonidet P-40, 0.1% SDS, 100ug/ml phenylmethysulfonyl fluoride (PMSF), 0.5% sodium deoxycholate, 1 mM sodium orthovanadate, 2 ug/ml aprotin, 2 ug/ml leupeptin, 5 mM EDTA in PBS] buffer. Chemokine levels in homogenates of equal amounts of total protein were measured using specific sandwich enzyme immunometric assay kits for rat. Chemokines in conditioned media from HKC were determined by specific sandwich ELISA kits for human (R&D Systems) according to the manufacturer's instructions. Results were normalized for protein amounts in kidney homogenates, or for cell number in cultures.

In certain embodiments, western immunoblot analysis is carried out using well known methods. For example, cells or tissues were solubilized or homogenized in RIPA buffer at 4° C. for 20 min. The supernatants are collected after centrifugation at 13,000×g for 10 min at 4° C. Protein concentration is determined using a bicinchoninic acid protein assay kit (Sigma). Samples of equal amount of protein were mixed with Laemmli's sample buffer, fractionated by 7.5-15% SDS-polyacrylamide gels under reducing condition, and transferred to nitrocellulose membrane. The membrane is probed with specific antibodies. The blots are developed using an enhanced chemiluminescence system (Amersham).

XI. Methods of Treatment

In certain embodiments, the present disclosure provides methods of inhibiting GSK3b and methods of treating kidney inflammation and disease. These methods involve administering to the individual a therapeutically effective amount of one or more therapeutic agents as described above. These methods are particularly aimed at therapeutic and prophylactic treatments of animals, and more particularly, humans.

As described herein, kidney diseases include, but are not limited to, acute kidney injury or infection such as repeated kidney infections, or a chronic condition, e.g., diabetes or hypertension, that may lead to chronic kidney disease, glomerulonephritis, glomerulosclerosis, diabetic nephropathy, polycystic kidney disease, inflammatory kidney disease, a congenital kidney pathology, Lupus or other diseases that affect the body's immune system, and obstructions such as kidney stones, tumors or an enlarged prostate gland.

In certain embodiments of such methods, the GSK3b inhibitory compound blocks GSK3b-mediated phosphorylation of NFkB p65 at amino acid residue S468. In certain embodiments, the level of phosphorylation of NFkB p65 at amino acid residue S468 is decreased. In certain embodiments, the level of phosphorylation of NFKB p65 at amino acid residue S468 is decreased by 90%, 80%, 70%, 60%, 50%, 40%, 30%, 20%, or 10%.

In certain embodiments of such methods, one or more therapeutic agents can be administered, together (simultaneously) or at different times (sequentially). In addition, therapeutic agents can be administered with another type of compounds for treating kidney inflammation or disease.

In certain embodiments, the subject methods of the disclosure can be used alone. In certain embodiments, the methods of the application may be combined with known treatments for kidney inflammation or disease. In certain embodiments, the known treatment may include surgery, cytotoxic drugs, and/or anti-inflammatory treatment. In certain embodiments, the treatment may include corticosteroids. One of ordinary skill in the art will be able to determine the current known treatment protocols for kidney inflammation or disease.

Depending on the nature of the combinatory therapy, administration of the therapeutic agents of the disclosure may be continued while the other therapy is being administered and/or thereafter. Administration of the therapeutic agents may be made in a single dose, or in multiple doses. In some instances, administration of the therapeutic agents is commenced at least several days prior to the conventional therapy, while in other instances, administration is begun either immediately before or at the time of the administration of the conventional therapy.

XII. Methods of Administration and Pharmaceutical Compositions

In certain embodiments, the subject compositions of the present disclosure are formulated with a pharmaceutically acceptable carrier. Such therapeutic agents can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject agents include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of kidney inflammation or disease therapeutic agent and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject therapeutic agent as an active ingredient.

In solid dosage forms for oral administration (capsules, tablets, pills, dragees, powders, granules, and the like), one or more therapeutic agents of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In particular, methods of the disclosure can be administered topically, either to skin or to mucosal membranes such as those on the cervix and vagina. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject agents may be mixed under sterile conditions with a pharmaceutically acceptable carrier, and with any preservatives, buffers, or propellants which may be required. The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject therapeutic agent, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more therapeutic agents in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations for intravaginal or rectally administration may be presented as a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

In certain embodiments, the compounds of the application may further comprise a kidney targeting agent. In certain embodiments, the agent binds to any kidney cell. In certain embodiments, an alkylglucoside vector is used for the delivery of compounds to the kidney as described in Shirota et al. J Pharmacol Exp Ther. 2001 November;299(2):459-67, incorporated by reference in its entirety herein. In certain embodiments, the targeting agent is a peptide that specifically binds to kidney cells such as those described in US Patent Application No. 20050074812, incorporated by reference in its entirety herein. In certain embodiments, the peptides may be fused to the antibodies of the application. In certain embodiments, the targeting agent is an aptamer that specifically binds to kidney cells. In certain embodiments, compounds may be conjugated to low-molecular weight proteins such as lysozyme to cause accumulation in the proximal tubular cells of the kidney as described in Kok et al. J Pharmacol Exp Ther. 1999; 288 (1):281-5, incorporated by reference in its entirety herein. In certain embodiments, compounds may be directly injected into a renal vein or artery for kidney-specific delivery.

Methods for delivering the subject nucleic acid compounds are known in the art (see, e.g., Akhtar et al., 1992, Trends Cell Bio., 2, 139; and Delivery Strategies for Antisense Oligonucleotide Therapeutics, ed. Akhtar, 1995; Sullivan et al., PCT Publication No. WO 94/02595). These protocols can be utilized for the delivery of virtually any nucleic acid compound. Nucleic acid compounds can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example though the use of conjugates and biodegradable polymers. For a comprehensive review on drug delivery strategies, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400. More detailed descriptions of nucleic acid delivery and administration are provided in Sullivan et al., supra, Draper et al., PCT WO93/23569, Beigelman et al., PCT Publication No. WO99/05094, and Klimuk et al., PCT Publication No. WO99/04819.

In certain embodiments, the nucleic acids of the instant disclosure are formulated with a pharmaceutically acceptable agent that allows for the effective distribution of the nucleic acid compounds of the instant disclosure in the physical location most suitable for their desired activity. Non-limiting examples of such pharmaceutically acceptable agents include: PEG, phospholipids, phosphorothioates, P-glycoprotein inhibitors (such as Pluronic P85) which can enhance entry of drugs into various tissues, biodegradable polymers, such as poly(DL-lactide-coglycolide) microspheres for sustained release delivery after implantation (Emerich, D F et al, 1999, Cell Transplant, 8, 47-58), and loaded nanoparticles such as those made of polybutylcyanoacrylate, which can deliver drugs across the blood brain barrier and can alter neuronal uptake mechanisms (Prog Neuropsychopharmacol Biol Psychiatry, 23, 941-949, 1999).

In other embodiments, certain of the nucleic acid compounds of the instant disclosure can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 5531-4; Ojwang et al., 1992, Proc. Natl. Acad. Sci. USA, 89, 10802-6;

Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45). Those skilled in the art realize that any nucleic acid can be expressed in eukaryotic cells from the appropriate DNA/RNA vector. The activity of such nucleic acids can be augmented by their release from the primary transcript by an enzymatic nucleic acid (Draper et al, PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J. Biol. Chem., 269, 25856; all of these references are hereby incorporated in their totalities by reference herein). Gene therapy approaches specific to the CNS are described by Blesch et al., 2000, Drug News Perspect., 13, 269-280; Peterson et al., 2000, Cent. Nerv. Syst. Dis., 485-508; Peel and Klein, 2000, J. Neurosci. Methods, 98, 95-104; Hagihara et al., 2000, Gene Ther., 7, 759-763; and Herrlinger et al., 2000, Methods Mol. Med., 35, 287-312. AAV-mediated delivery of nucleic acid to cells of the nervous system is further described by Kaplitt et al., U.S. Pat. No. 6,180,613.

In another aspect of the disclosure, RNA molecules of the present disclosure are preferably expressed from transcription units (see for example Couture et al., 1996, TIG., 12, 510) inserted into DNA or RNA vectors. The recombinant vectors are preferably DNA plasmids or viral vectors. Ribozyme expressing viral vectors can be constructed based on, but not limited to, adeno-associated virus, retrovirus, adenovirus, or alphavirus. Preferably, the recombinant vectors capable of expressing the nucleic acid compounds are delivered as described above, and persist in target cells. Alternatively, viral vectors can be used that provide for transient expression of nucleic acid compounds. Such vectors can be repeatedly administered as necessary. Once expressed, the nucleic acid compound binds to the target mRNA. Delivery of nucleic acid compound expressing vectors can be systemic, such as by intravenous or intramuscular administration, by administration to target cells ex-planted from the patient followed by reintroduction into the patient, or by any other means that would allow for introduction into the desired target cell (for a review see Couture et al., 1996, TIG., 12, 510).

In one aspect, the disclosure contemplates an expression vector comprising a nucleic acid sequence encoding at least one of the nucleic acid compounds of the instant disclosure. The nucleic acid sequence is operably linked in a manner which allows expression of the nucleic acid compound of the disclosure. For example, the disclosure features an expression vector comprising: a) a transcription initiation region (e.g., eukaryotic pol I, II or III initiation region); b) a transcription termination region (e.g., eukaryotic pol I, II or III termination region); c) a nucleic acid sequence encoding at least one of the nucleic acid catalyst of the instant disclosure; and wherein said sequence is operably linked to said initiation region and said termination region, in a manner which allows expression and/or delivery of said nucleic acid compound. The vector can optionally include an open reading frame (ORF) for a protein operably linked on the 5' side or the 3'-side of the sequence encoding the nucleic acid catalyst of the disclosure; and/or an intron (intervening sequences).

In certain embodiments, the nuclei acid compounds of the application may be delivered specifically to the kidney. Exemplary modifications and methods for targeting nucleic acid compounds to the kidney are found in U.S. Patent Publication No. 20050153337, herein incorporated by reference in its entirety. In certain embodiments, nucleic acid compounds of the application may be expressed from a kidney-specific promoter (see for example Igarashi et al. J Am Soc Nephrol 15:2237-2239, 2004, herein incorporated by reference in its entirety). In certain embodiments, the targeting agent is an aptamer that specifically binds to kidney cells.

Exemplification

Inhibition of GSK-3b expression and/or activity leads to significant anti-inflammatory effects. GSK3b was markedly up-regulated in several experimental models of chronic kidney disease characterized by prominent interstitial inflammation. In the kidney, therapies such as sub-lethal injections of LPS or administration of HGF that suppress renal inflammation and injury, markedly decreased GSK3b expression. Inhibition of GSK3b kinase activity by hepatocyte growth factor, through activating PI3K-Akt mediated phosphorylation of GSK3b, profoundly ameliorating gross renal inflammation and reduced renal expression of proinflammatory molecules such as RANTES, and E-selectin, e.g., in a rat model remnant kidney disease. The data described herein indicate that GSK3b plays an important role in the pathogenesis of inflammation, and inhibition of GSK3b kinase activity suppresses inflammation and injury in renal disease.

EXAMPLE 1

Anti-inflammatory Effect of HGF in Progressive Chronic Kidney Disease: Targeting the Inflamed Vascular Endothelium We examined the molecular mechanism of HGF's anti-inflammatory actions in a model of CKD. Beginning 2 wk after $\frac{5}{6}^{th}$ nephrectomy, rats received exogenous HGF, neutralization of endogenous HGF by daily injection of an anti-HGF antibody, or preimmune IgG for 2 wk. HGF ameliorated, whereas blocking HGF worsened inflammation in remnant kidneys. There were parallel alterations in endothelial activation and inflammation, marked by de novo E-selectin expression and leukocyte adhesion to renal vascular endothelium. In vitro, HGF abrogated monocyte adhesion to TNF-α-activated endothelial monolayers and suppressed endothelial expression of E-selectin, which depended on NF-kB signaling. In addition, HGF suppressed TNF-a induced NF-kB reporter gene activity and counteracted NF-kB interaction with kB elements at the E-selectin gene level. Studies revealed that suppression of NF-kB depended HGF's inhibition of NF-kB and IkB phosphorylation and IkB degradation. In vivo, exogenous HGF markedly diminished sequestration of circulating macrophages in the remnant kidney, mimicking the action of an E-selectin blocking antibody. Thus, the GSK3b inhibitor HGF has direct anti-inflammatory effects via suppression of NF-KB and endothelial inflammation.

EXAMPLE 2

Hepatocyte Growth Factor Suppresses Acute Renal Inflammation by Inhibition of Endothelial E-selectin Vascular endothelial activation, marked by expression of E-selectin, is an essential event in the process of leukocyte extravasation and inflammation. We examined the effect of HGF on endothelial E-selectin expression in acute inflammation induced by TNF-α. In vitro, HGF suppressed TNF-α-induced expression of E-selectin in human umbilical vein endothelial cells (HUVEC) and inhibited E-selectin mediated monocytic adhesion to endothelial cells. HGF activated phosphatidylinositol 3-kinase (PI3K)-Akt that in turn inhibited its downstream transducer, GSK-3b, by phosphorylation at serine-9. Blockade of the PI3K-Akt pathway abrogated HGF induced inhibition of GSK3b and suppression of E-selectin. Inhibition of GSK3b by lithium also suppressed TNF-α-induced E-selectin expression and monocytic adhesion, mimicking the action of HGF. Ectopic expression of an uninhibitable mutant GSK3b abolished HGF suppression of E-selectin, again suggesting inhibition of GSK3b mediates HGF suppression of E-selectin. In vivo, infusion of exogenous HGF reduced endothelial expression of E-selectin induced by bolus injection of TNF-α. This was associated with less sequestration of circulating macrophages in the kidney. These findings demonstrate that GSK3b inhibition is central to HGF's suppression of acute endothelial and renal inflammation.

EXAMPLE 3

Activation of PI3K-Akt-GSK3βPathway Mediates Hepatocvte Growth Factor Inhibition of RANTES Expression in Renal Tubular Epithelial Cells.

HGF suppresses basal and TNF-α-induced expression of RANTES in a time and dose dependent fashion in HKC. HGF elicited PI3K-Akt activation and inhibited GSK3, by phosphorylation at Ser-9. Blocking PI3K-Akt abrogated HGF inhibition of RANTES, demonstrating that the PI3K-Akt pathway mediates HGF action. Specific inhibition of GSK3 activity by lithium also suppressed basal and TNF-a-induced RANTES expression, mimicking HGF. Overexpression of wild type GSK3β in HKC did not alter the inhibitory action of HGF on RANTES. In contrast, expression of an uninhibitable mutant of GSK3β (S9A-GSK3β) abolished HGF inhibition of basal and TNF-α stimulated RANTES expression. PI3K-Akt activation and subsequent inhibitory phosphorylation of GSK3β are required for HGF suppression of RANTES in HKC.

EXAMPLE 4

Hepatocyte Growth Factor Ameliorates Renal Interstitial Inflammation in Rat Remnant Kidney by Modulating Tubular Expression of MCP-1 and RANTES Continuous infusion of HGF for two weeks reduces inflammatory infiltration, tubular and glomerular injury in remnant kidney rats. Conversely, HGF neutralization worsened inflammation and scarring. HGF decreased interstitial macrophages by more than 50%, while HGF blockade markedly increased it. Renal ablation stimulated tubular expression of chemokines MCP-1 and RANTES, recruiting inflammatory cells to the renal interstitiium. HGF neutralization further enhanced expression, while HGF infusion decreased staining to normal. In human proximal tubular epithelial cells (HKC), HGF suppressed MCP-1 and RANTES in a time and dose dependent manner. TNF-α, a proinflammatory cytokine, markedly enhanced chemokine expression in HKC cells and simultaneous treatment with HGF blocked this induction. HGF also suppressed basal and TNF-α induced expression of MCP-1 and RANTES in immortalized rat proximal tubular cells (IRPTC).

EXAMPLE 5

Hepatocvte Growth Factor Ameliorates Progression of Interstitial Fibrosis in Rats with Established Renal Injury Remnant kidney rats were treated with HGF, which reduced interstitial injury. HGF did not reduce expression of transforming growth factor-beta (TGF-β), or in epithelial cell apoptosis or transdifferentiation. Rather, HGF induced fibrinolysis by increasing expression of metalloproteinase-9 (MMP-9) and decreasing levels of plasminogen activator inhibitor-1 (PAI-1) and tissue inhibitor of metalloproteinase-1 (TIMP-1). Thus, HGF inhibits progression of established renal disease by activating matrix degradative pathways.

EXAMPLE 6

Figures 2A, 2B:
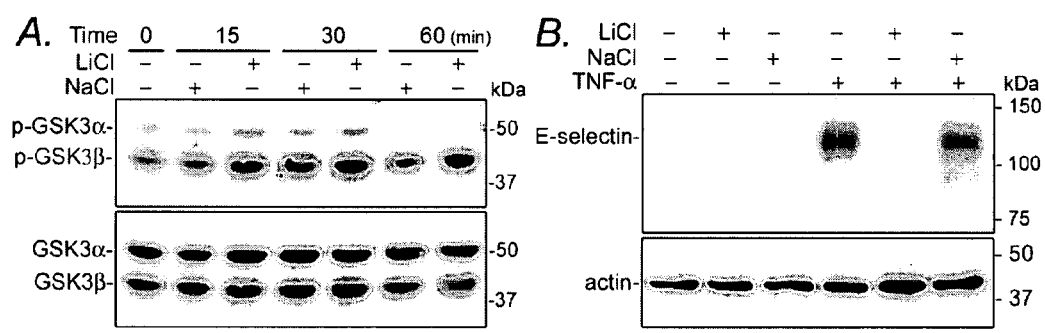
FIGS. 2A-2B show that specific inhibition of GSK3 by lithium (LiCl) suppresses TNF-α induced E-selectin expression in HUVEC cells. (A) LiCl (20 mM) induced inhibitory phosphorylation in HUVEC cells. As an osmolality control, sodium chloride (20 mM) had little or no effect. (B) Lithium (20 mM), but not sodium (20 mM), abolished TNF-a induction of E-selectin.

GSK3b Inhibition Attenuates TNF-α Induced De Novo Expression of Endothelial E-selectin At the optimal concentration not associated with apoptosis, lithium (20 mM) inhibits GSK3b activity by phosphorylation at Serine 9, and attenuates TNF-α-induced E-selectin in HUVEC (FIG. 2).

Figures 3A, 3B:
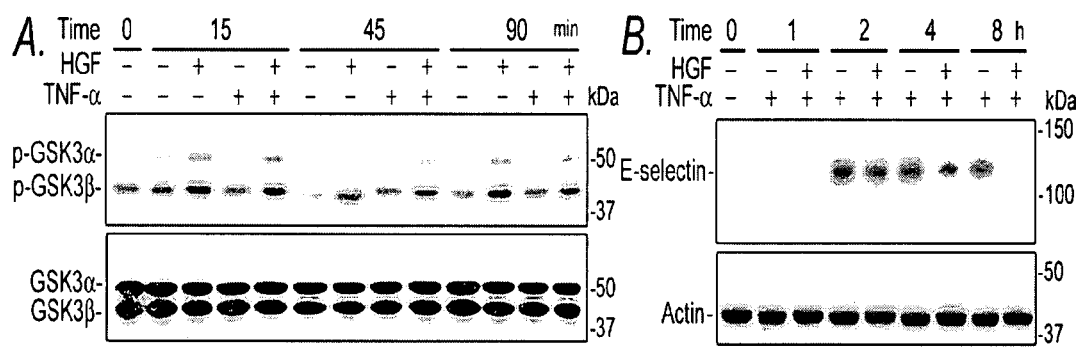
FIGS. 3A-3B show that HGF (100 ng/ml) induces inhibitory phosphorylation of GSK3b and attenuates TNF-a (0.5 ng/ml) elicited E-selectin expression in HUVEC.

We showed that HGF inactivates GSK3b by inhibitory phosphorylation at ser-9 (FIG. 3A). HGF also attenuates TNF-α elicited E-selectin expression in endothelial cells (FIG. 3B).

EXAMPLE 7

Figures 4A, 4B, 4C:
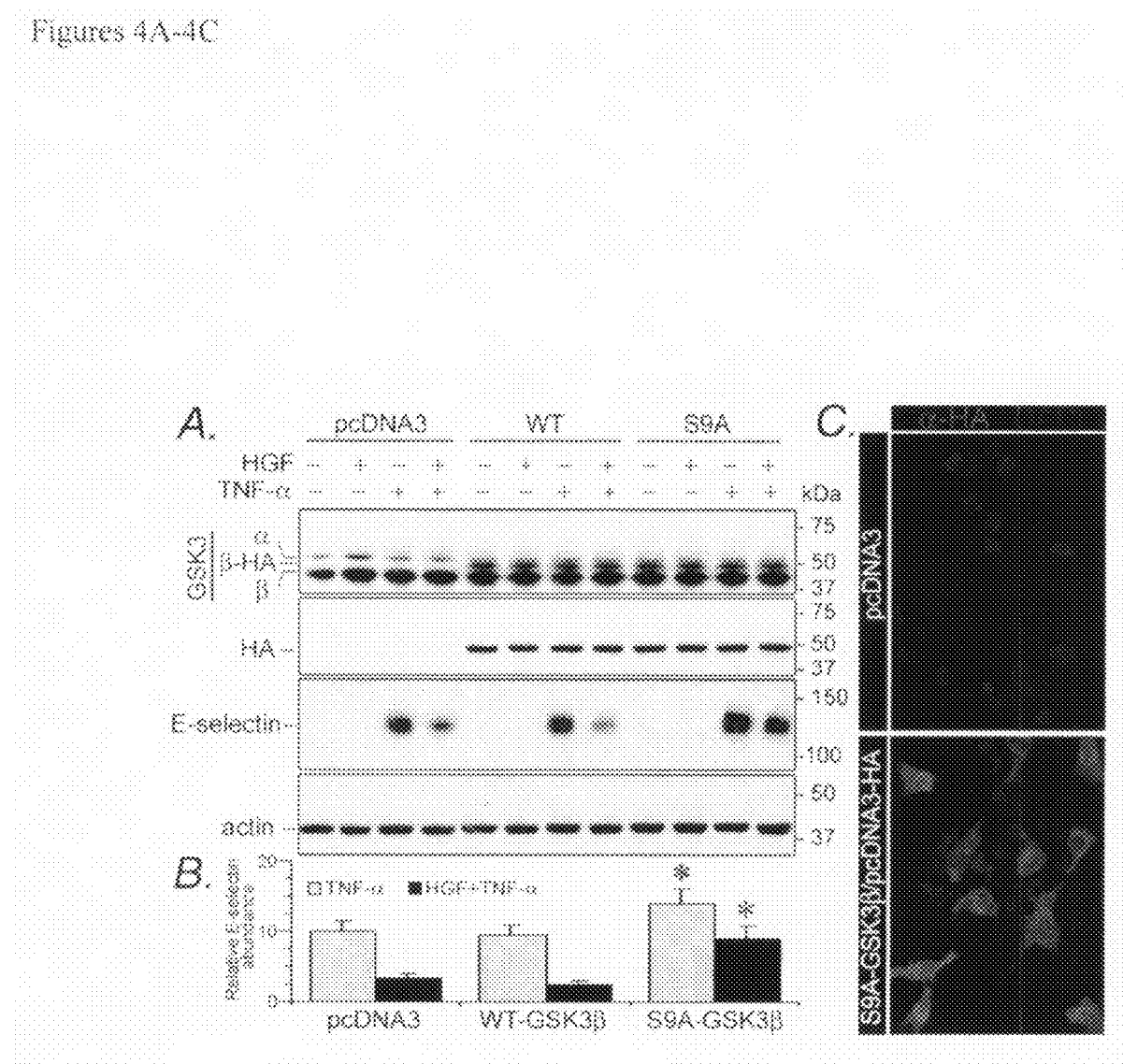
FIGS. 4A-4C shows that forced expression of uninhibitable GSK3b enhances TNF-a induced E-selectin expression and abolishes HGF inhibition of endothelial E-selectin. (A) immunoblot analysis of cell lysates 24 h after transfection. (C) HA staining in transfected cells. (B) Relative amounts of E-selectin by densitometry of the bands in (A). *P<0.01 vs cells transfected with pcDNA3 or WT (n=3).

Ectopic Expression of an Uninhibitable Mutant GSK3b Enhances TNF-α Elicited E-selectin Expression and Abolishes HGF Inhibition Vectors encoding the wild type GSK3b (WT) or an uninhibitable mutant GSK3b[64] were transfected into HUVEC with pcDNA3 as a transfection control. Whole cell lysates were analyzed by immunoblotting for hemagglutin (HA) or HA-GSK3b (FIG.4A). Immunofluorescent detection using an antibody against the HA epitope revealed that over 50% of the cells expressed the HA-tagged constructs 24 h after transfection (FIG. 4C). Shown in FIGS. 4A & B, TNF-a induced E-selectin expression was significantly enhanced in S9A-GSK3b transfected cells. HGF inhibition of E-selectin expression was evident in HUVEC cells transfected with pcDNA3 or HA-WT-GSK3b. In contrast, ectopic expression of HA-S9A-GSK3b abolished the suppressive action of HGF suggesting that phosphorylation of GSK3b at Serine-9 regulates E-selectin expression in HUVEC.

EXAMPLE 8

GSK3b Inhibitors Attenuate TNF-α Induced Chemokine Expression in TEC

Figure 5:
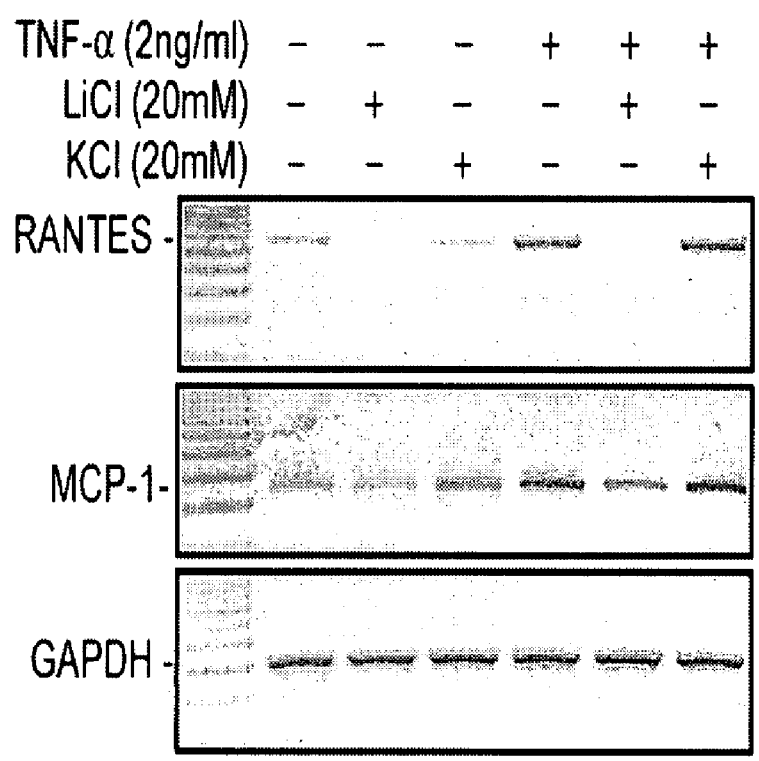
FIG. 5 shows that specific inhibition of GSK3 by lithium (LiCl) suppresses TNF-α induced chemokine expression in HKC cells. As an osmolality control, KCl had no effect.

At the optimal concentration not associated with apoptosis, lithium (20 mM) lessens TNF-a-induced RANTES and MCP-1 expression. Potassium, an osmolality control, had no effect (FIG.5).

Figure 6:
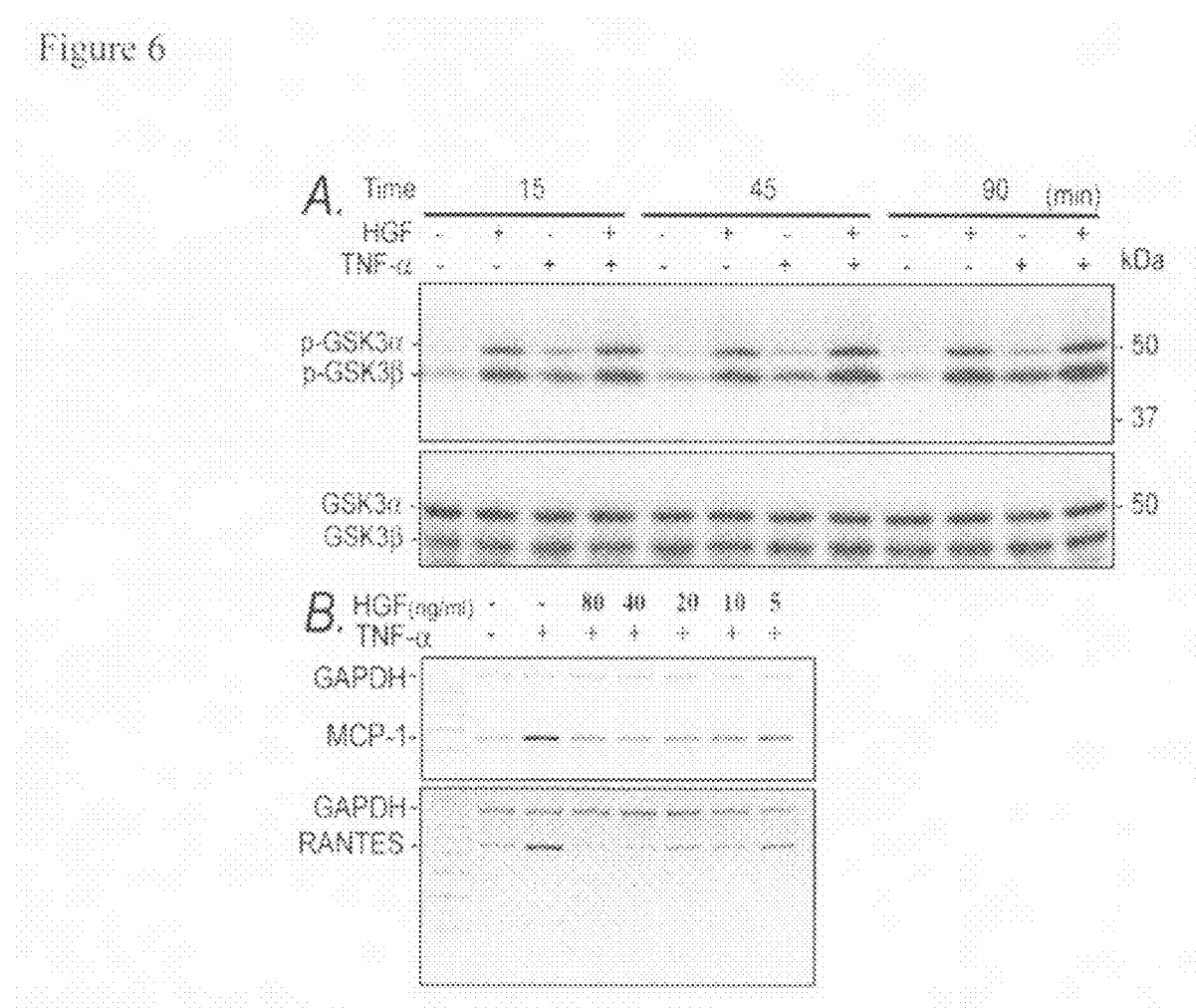
FIGS. 6A-6B shows that HGF (20 ng/ml) induces inhibitory phosphorylation of GSK3b and attenuates TNF-a (2 ng/ml) elicited chemokine expression in TEC.

HGF activates PI3K-Akt in TEC and GSK3b is inactivated by PI3K-Akt mediated inhibitory phosphorylation. HGF also attenuates TNF-α elicited chemokine expression, suggesting GSK3b inhibition accounts for HGF's effect on TEC (FIG.6).

EXAMPLE 9

Ectopic Expression of an Uninhibitable Mutant GSK3b Enhances TNF-α Induced MCP-1 and RANTES Production and Abolishes HGF's Inhibitory Effect Vectors encoding wild type or an uninhibitable GSK3b were transfected into HKC cells with pcDNA3 as control.

Figures 7A, 7B, 7C:
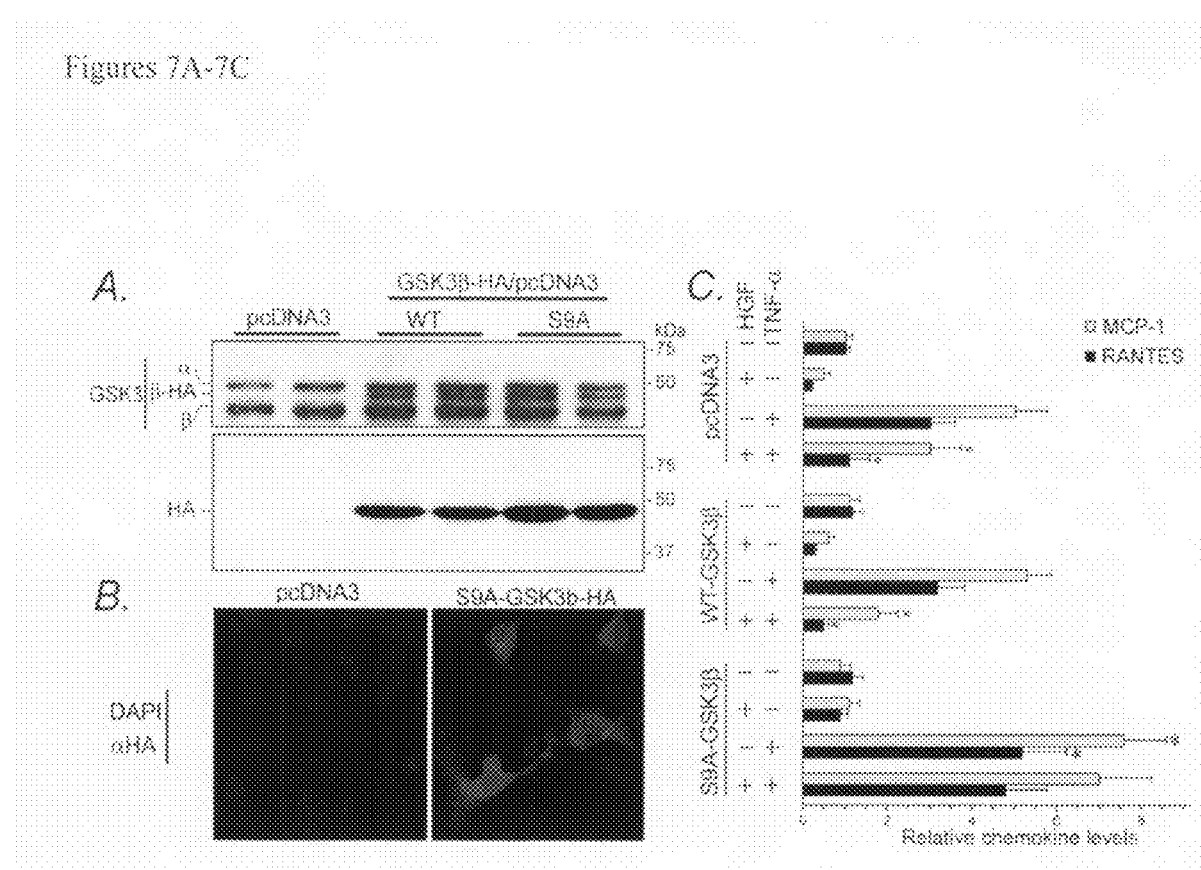
FIGS. 7A-7C show that ectopic expression of the uninhabitable mutant GSK3b (S9A) enhances TNF-α induced chemokine expression and abolishes HGF's inhibitory effect. (A) 24 hours after transfection, cell lysates were subjected to immunoblot analysis. (B) HA staining in the transfected cells. (C) Relative chemokine levels in the conditioned media was estimated by ELISA. *P<0.01 vs TNF-a treated cells but transfected with pcDNA3 or WT (n=3).#P<0.05 vs TNF treated cells with the same transfection.

Lysates were immunoblotted for hemagglutin (HA) or HA-GSK3b. Immunofluorescence revealed that over 70% of the cells expressed the HA-tagged constructs at 24 h (FIG. 7B). TNF-α induced expression of MCP-1 and RANTES was significantly enhanced in S9A-GSK3b transfected cells (FIG. 7C). HGF inhibition of chemokine expression was evident in HKC cells transfected with pcDNA3 or WT-GSK3b. In contrast, expression of S9A-GSK3b abolished HGF suppression of E-selectin. Thus, inhibitory phosphorylation of GSK3b at Serine-9 regulates chemokine expression in TEC cells.

EXAMPLE 10

HGF (GSK3b Inhibitor) Suppresses NF-κB in Endothelial Cells and TEC

To explore the role of GSK3b in HGF suppression of inflammation, we examined the effect of HGF on NF-κB activation in endothelial cells (FIG. 8A~C) and TEC (FIG. 8D). HGF significantly reduced TNF-α induced NF-κB transcription activity at 24 h as assessed by 3κB luciferase reporter gene assay. (FIG. 8A). To determine whether HGF modulation of NF-κB transcriptional activity alters target gene (E-selectin) levels, DNA affinity precipitation assay was carried out at 4 h after treatment. Proteins in cell lysates were pulled down by biotin labeled oligonucleotides with the sequence of the E-selectin promoter region spanning the κB elements. Immunoblot analysis of recipitated NF-κB p65 protein showed that HGF significantly blunted TNF-α induced NF-κB binding to E-selectin promoter sequence (FIG. 8B). To further examine the effect of HGF on NF-κB binding to the E-selectin gene in vivo, chromatin immunoprecipitation (ChIP) was applied at 4 h after treatments (FIG. 8C). PCR amplification of anti-NF-κB p65 immunoprecipitated chromatin again showed that HGF prevents NF-κB mediated transcription of E-selectin. In HKC cells, gel shift assay demonstrated that TNF-α induced binding of HKC nuclear extract to oligionucleo-tides with an NF-κB consensus sequence was markedly blunted by HGF at 4 h.

EXAMPLE 11

Renal Expression of GSK3b is Markedly Elevated in Animal Models of Renal Inflammation We found only weak GSK3b expression in normal kidney, but levels increased markedly in multiple models of CKD, including hypokalemic nephropathy (LK), oxalate nephropathy (OxN), the remnant kidney, and lupus nephritis, as probed by western immunoblot using a mouse monoclonal anti-GSK3b antibody (FIG. 9). Of note, the abundance of GSK3b correlated with the extent of inflammation and injury and was markedly suppressed by treatments that reduced renal injury and inflammation. These findings suggest that GSK3b is an important inhibitor of renal inflammation and injury.

EXAMPLE 12

Figures 10A, 10B:
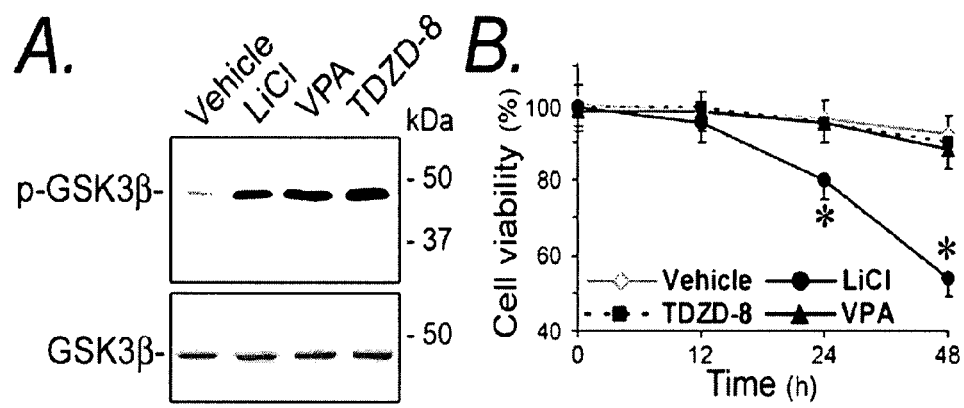
FIGS. 10A-10B show that selective GSK3b inhibition induces inhibitory phosphorylation of GSK3b in HKC cells. (A) Selective GSK3b inhibitors lithium, valproate, and TDZD-8 all induced marked GSK3b phosphorylation. (B) Only lithium significantly reduced cell viability in TNF-a (2 ng/ml) treated cells at 24 h.
Figure 11:
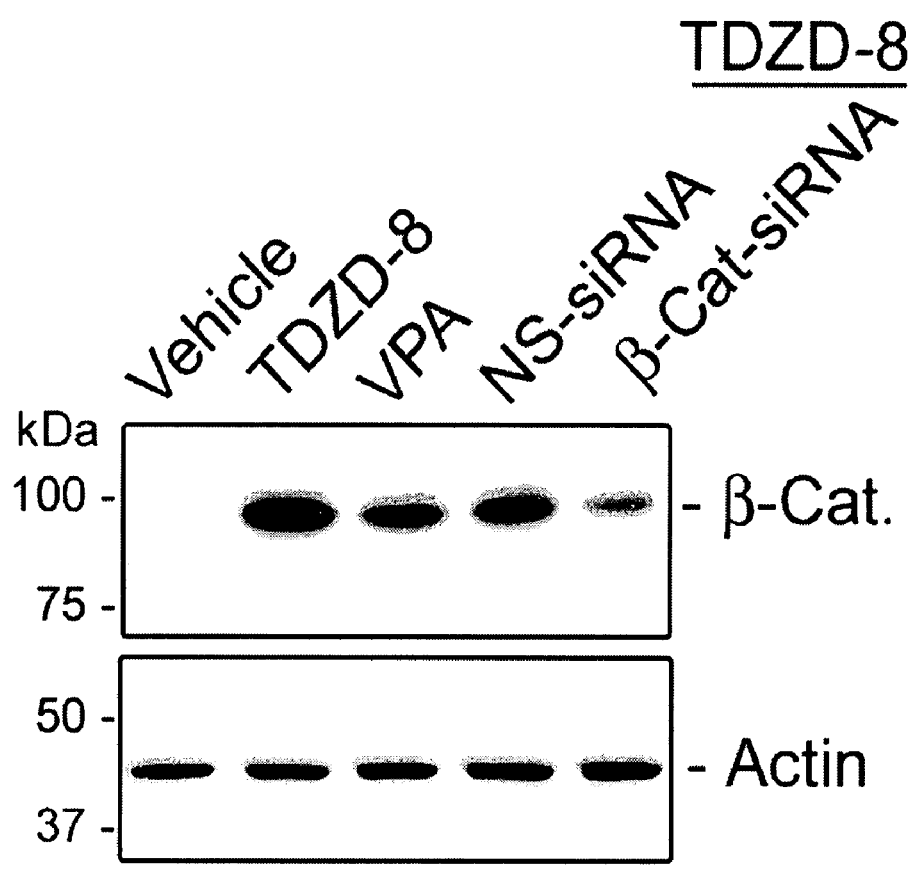
FIG. 11 shows that specific small molecule GSK3b inhibitors, including valproate (VPA) and TDZD-8, induced b-catenin (b-Cat.) accumulation in HKC. This effect was blunted by RNAi of b-Catenin. NS, non-specific siRNA.

Selective GSK3b Inhibitors Induce Inhibitory Phosphorylation of GSK3b and Raise b-Catenin in HKC Selective GSK3b inhibitors lithium, valproate, and TDZD-8 all induced marked GSK3b phosphorylation. (FIG. 10A) Of note, only lithium sensitized cells to TNF-a induced apoptosis (FIG. 10B). Inhibition of GSK3b resulted in abundant accumulation of b-catenin, a critical signaling molecule in the Wnt pathway. This was attenuated by silence of b-catenin with a specific siRNA. (FIG. 11)

EXAMPLE 13

Specific Knockdown of GSK3b Does Not Alter the Cell Viability

Figures 12A, 12B:
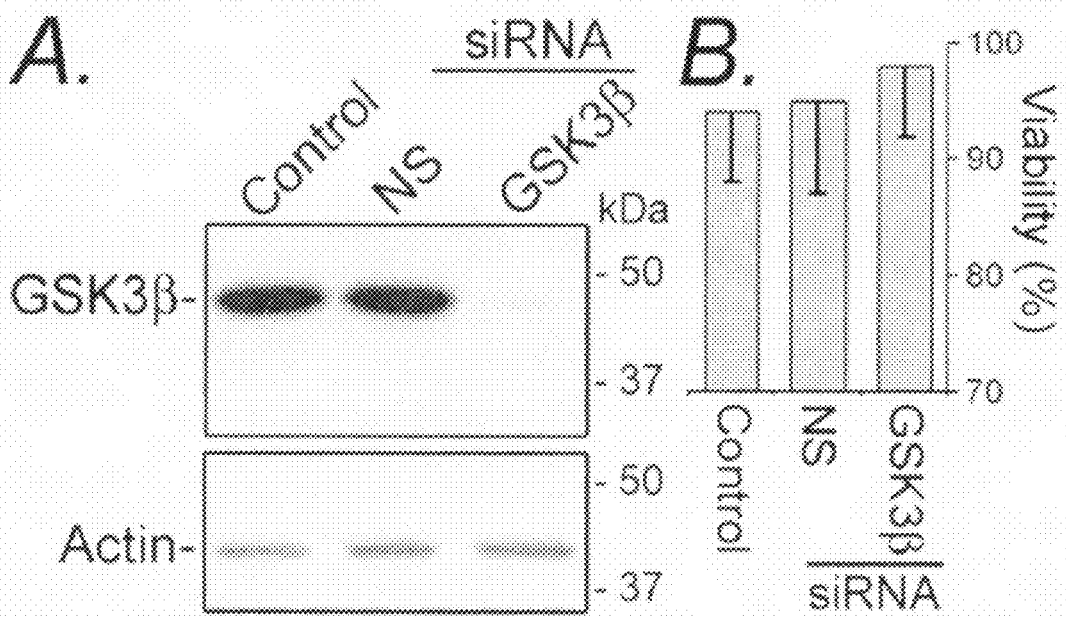
FIGS. 12A-12B shows knock down of GSK3b by RNAi in HKC cells. (A) Transfection of specific siRNA for GSK3b strikingly knocked down constitutive GSK3b expression in HKC cells, while non-specific (NS) siRNA had minor effect. (B) 48 h after RNAi of GSK3b no significant reduction in cell viability was noted.

Specific knockdown of GSK3b expression in HKC cells by RNAi did not significantly reduce cell viability (FIG. 12).

EXAMPLE 14

GSK3b Inhibition Ameliorates Acute Renal Inflammation

Florid inflammation was evident in kidneys 5 days after unilateral urethral obstruction (UUO) (FIG. 13, A,a). associated with elevated renal expression of GSK3b (FIG. 13C). Treatment with valproate for 5 days prevented inflammatory infiltration and blunted induced expression of GSK3b in the diseased kidney. Inhibitory phosphorylation of GSK3b was also much greater in VPA treated kidneys, consistent with its proposed mechanism of action. The number of infiltrating cells in the obstructed kidney was highly correlated with the level of GSK3b expression in UUO rats in both groups.

EXAMPLE 15

Figures 14A, 14B, 14C, 14D:
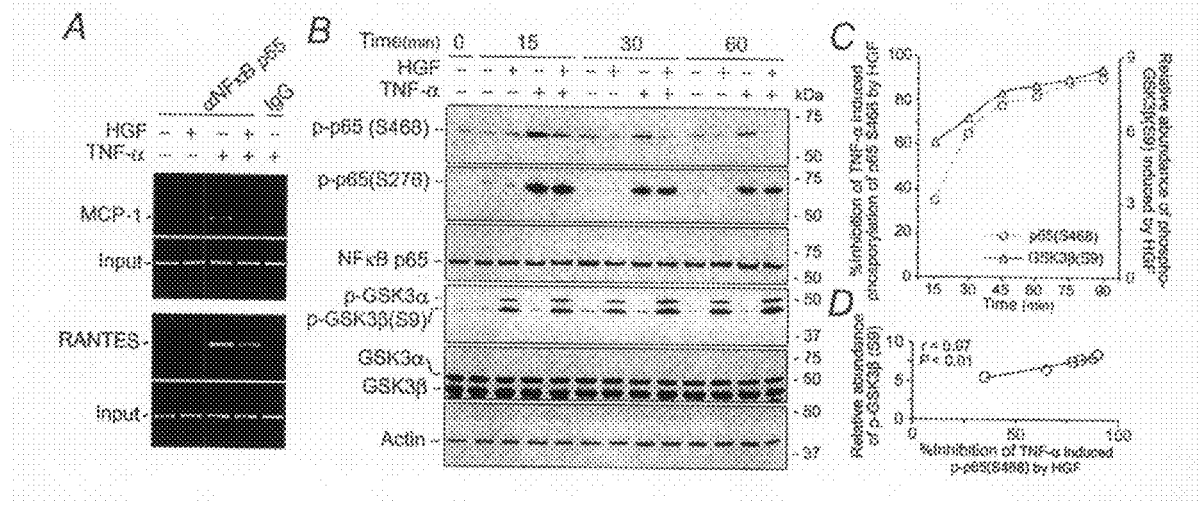
FIGS. 14A-14D show that HGF inhibits NFkB transactivative activity and NFkB phosphorylation at S468 in human kidney tubular epithelial cells, which is closely associated with HGF induced inhibitory phosphorylation of GSK3b. A, chromatin immunoprecipitation assay demonstrated that TNF-a induced recruitment of NFkB to proinflammatory genes like MCP-1 and RANTES is markedly attenuated by HGF; B, HGF suppresses NFkB phosphorylation specifically at S468 but not at other sites like S276, meanwhile HGF induces inhibitory phosphorylation of GSK3b at S9; C, Relative inhibition of TNF-a induced phosphorylation of p65 S468 by HGF and relative abundance of phosphorylated GSK3b (S9) induced by HGF; D, HGF induced inhibitory phosphorylation of GSK3b at S9 highly correlates with HGF inhibition of TNF-a elicited phosphorylation of p65 at S468.

Suppression of NFkB Activity by HGF is Associated with Inhibitory Phosphorylation of GSK3b Proinflammatory stimulation by TNF-a induced abundant recruitment of NFkB p65 to the promoter region of both MCP-1 and RANTES genes as shown by the ChIP assay (FIG. 14A). This effect was substantially attenuated by concomitant HGF treatment, suggesting that HGF suppresses NFKB activity. To further understand the molecular mechanism underlying this phenomenon, the NFKB signaling pathway was dissected. NFkB activation, characterized by phosphorylation of a number of amino acid residues in NFkB p65 subunits, is one important prerequisite for transactivation of the target genes. TNF-a treatment induced an immediate serine phosphorylation at multiple sites in NFkB p65 including 276, 468 and 536 (data not shown). HGF co-treatment markedly abolished TNF-a induced phosphorylation of S468 in a time dependent fashion, but had minimal effect on S276 (FIG. 14B) or S536 (not shown), indicating that HGF inhibition of NFkB p65 serine phosphorylation is site specific. Of note, HGF but not TNF-a could simultaneously induce GSK3b phosphorylation at $Ser_9$ (FIG. 14B), which denotes inactivation of GSK3b kinase activity. The HGF induced inhibitory GSK3b phosphorylation is in parallel with the suppression of NFkB p65 phosphorylation at S468 along the time after treatment (FIG. 14C), exhibiting a significantly strong correlationship (FIG. 14D). All these findings suggested that HGF regulates NFkB p65 phosphorylation at S468 and inhibits transactivation of its target genes. This event is associated with concomitant inhibitory phosphorylation of GSK3b induced by HGF.

EXAMPLE 16

GSK3b is Required for TNF-a Induced NFkB p65 Phosorylation at S468

Figure 15:
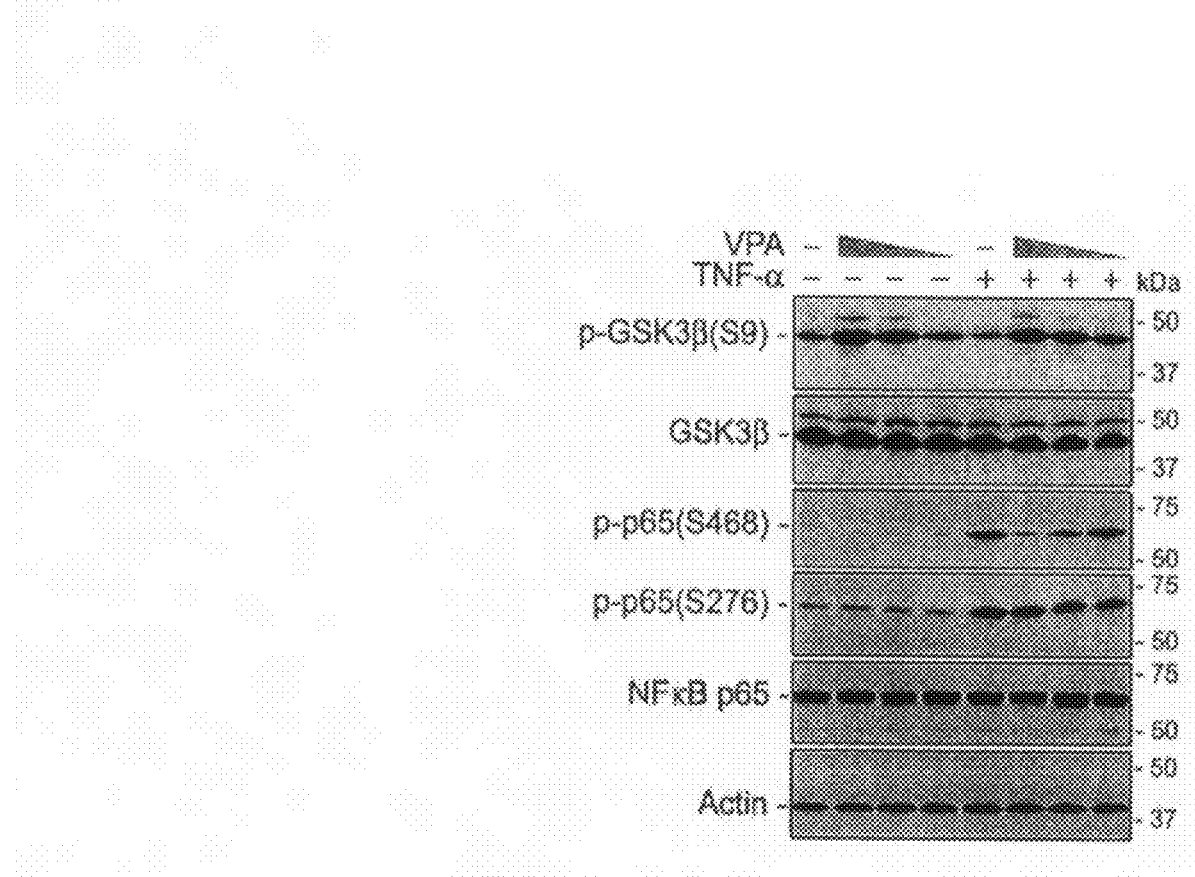
FIG. 15. Valproic acid (VPA), a selective GSK3b inhibitor, suppresses TNF-a elicited p65 phosphorylation at S468 and induces inhibitory phosphorylation of GSK3b at S9, reminiscent of the effect of HGF. HKC cells were treated with or without TNF-a (2 ng/ml) in the presence or absence of decreasing amounts (1 mM, 100 mM, 10 uM) of VPA for 60 minutes. Immunoblot assays were carried out on total cell lysates.

Sodium valproate (VPA), a selective GSK3b inhibitor, induced phosphorylation of GSK3b at $Ser_9$, which denotes inactivation of the GSk3b kinase activity. Meanwhile VPA abrogates the TNF-a induced NFkB p65 phosphorylation at $Ser_{468}$ in a dose dependent manner but minimally affected phosphorylation of p65 at other sites, reminiscent of the effect of HGF (FIG. 15). These data implied that GSK3b inactivation subsequent to inhibitory phosphorylation at $Ser_9$ is sufficient for HGF suppression of p65 phosphorylation at $Ser_{468}$ induced by TNF-a.

EXAMPLE 17

Figures 16A, 16B, 16C:
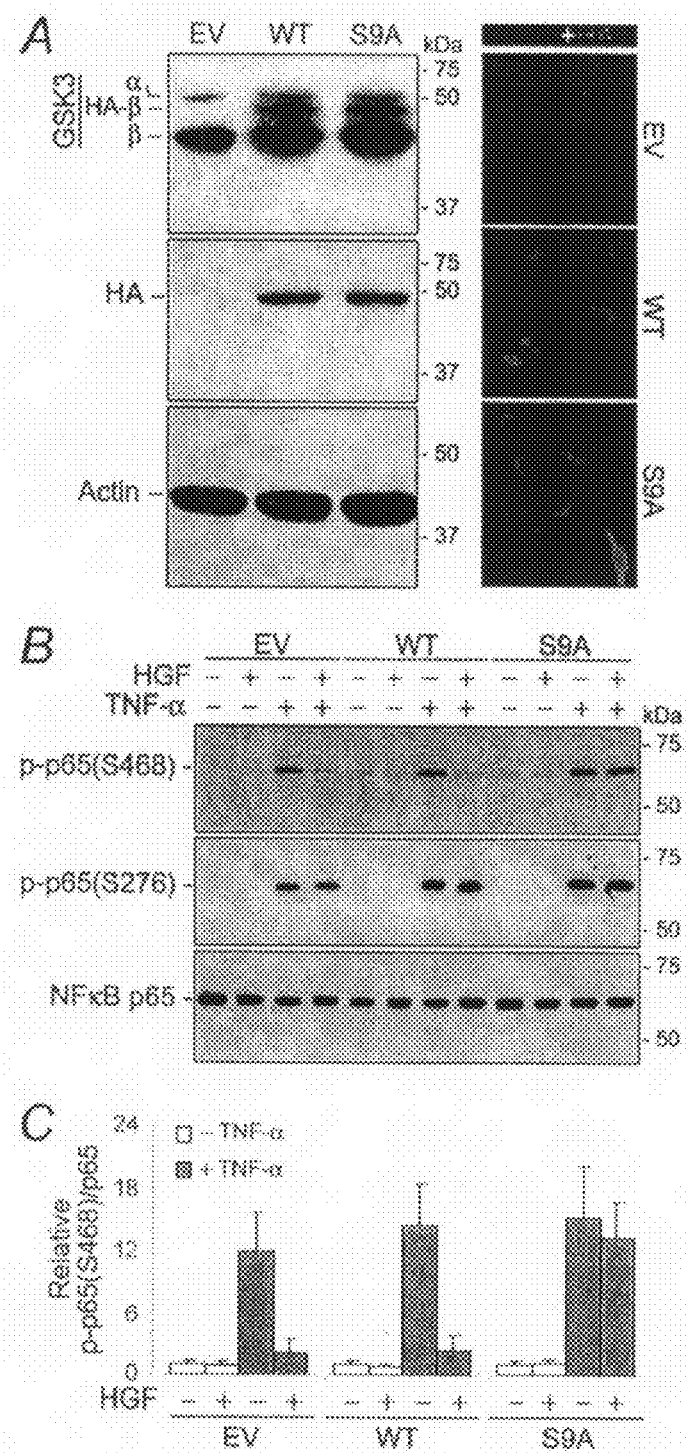
FIG. 16A-16C show that ectopic expression of the mutant uninhibitable GSK3b (S9A) largely abrogates HGF's suppressive effect on TNF-a induced phosporylation of p65 at S468. A, HKC cells were transiently transfected with the empty pcDNA3 vector (EV), or the vector encoding the hemagglutin (HA) conjugated wild type GSK3b or the mutant GSK3b in which the serine 9 was replaced by alanine. Whole cell lysates were harvested and analyzed for different molecules by western immunoblot. Fluorescent immunocytochemistry staining of HA demonstrated that ~70% cells expressed the vector. B, After transfected with different vectors, HKC cells were subjected to different treatment as indicated. Whole cell lysates underwent immunoblot assay. C, densitometric analysis of immunoblot in (B) showed that HGF's inhibitory effect on TNF-a induced phosphorylation of p65 at S468 was obliterated in HKC cells expressing GSK3b S9A.

Ectopic Expression of the Uninhibitable Mutant GSK3b Abolishes HGF Suppression of p65 Phosphorvlation at $Ser_{468}$ To further examine the role of inhibitory phosphorylation of GSK3b in HGF regulation of NFkB p65 phosphorylation, we studied the effect of forced expression of GSK3b. Vectors encoding the hemagglutin (HA) conjugated wild type GSK3b (WT) or uninhibitable mutant GSK3b, in which the regulatory $Ser_9$ residue was changed to alanine (S9A), were transfected to HKC. As a control, empty vector was used in parallel. To evaluate the levels of expression, whole cell lysates were analyzed by immunoblotting for HA or HA-GSK3b. The constructs were abundantly expressed 24 h after transfection. Immunofluorescent detection using an antibody against the HA epitope revealed that ~70% of the cells expressed the HA-tagged constructs (FIG. 16A). Shown in FIG. 16B, HGF inhibition of TNF-a-induced phosphorylation of NFkB p65 at S468 was evident in HKC transfected with EV or WT. In contrast, this suppressive effect by HGF was strikingly abolished in cells expressing S9A. The immunoblot results were further quantified by the densitometric analyses. Collectively, these findings suggest that inhibitory phosphorylation of GSK3b at S9 is required for HGF suppression of NFkB p65 phosphorylation at S468.

EXAMPLE 18

HGF Modulates the Physical Interaction Between GSK3b and NFkB p65

Figures 17A, 17B, 17C:
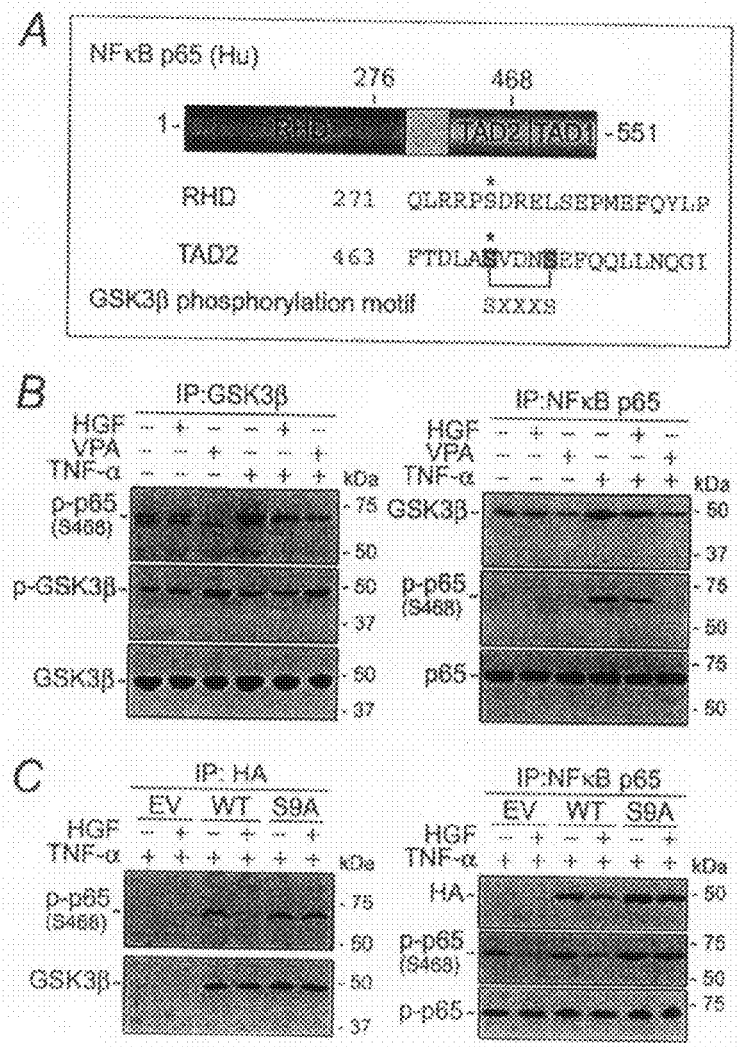
FIGS. 17A-17C show that HGF's suppressive effect on physical interaction between GSK3b and RelA/p65 mimics the action of valproic acid but is overridden in cells expression the mutant uninhibitable GSK3b. A, Sequence analysis demonstrates that S468 but not S276 is located in a GSK3b consensus motif.

Sequence analyses demonstrated that $Ser_{468}$ is situated at a typical GSK3b phosphorylation motif within the COOH-terminal transactivation domain of RelA/p65 (FIG. 17A), whereas both $Ser_{276}$ and $Ser_{563}$ (not shown) fail to match the consensus site of GSK3b, suggesting that position $Ser_{468}$ might be GSK3b's substrate. The intrinsic interaction between GSK3b and p65 was explored by co-immunoprecipitation. GSK3b was minimally detected with p65 in untreated cells but was substantially enhanced by TNF-a stimulation (FIG. 17B, right panel), suggesting that GSK3b physically interacts with p65 upon proinflammatory elicitation. TNF-a induced GSK3b to p65 interaction could be remarkably overridden by HGF, reminiscent the effect of VPA, the specific GSK3b inhibitor. Likewise, TNF-a induced more phosphorylated p65 ($Ser_{468}$) to coprecipitate with GSK3b as compared to non-treated cells (FIG. 17B, left panel), suggesting that GSK3b is closely associated with p65 phosphorylation at S468. HGF treatments abrogated TNFa induced co-precipitation, mimicking the action of VPA. To further examine whether HGF modulates the physical interaction between GSK3b and p65 through inhibitory phosphorylation of GSK3b, cells were transiently transfected with vectors encoding HA conjugated WT or S9A as well as empty vector before treatments with HGF and/or TNF-a. Upon TNF-a stimulation, ectopically expressed GSK3b that was conjugated with HA clearly co-precipitated with NFkB p65 in both WT and S9A transfected cells (FIG. 17C, right panel). HGF treatment markedly reduced HA co-precipitation with p65 in the WT transfected cells. In contrast, this inhibitory effect of HGF was considerably abrogated in HKC cells expressing S9A. Similarly, phosphorylated p65(S468) evidently co-precipitated with HA-tagged GSK3b in response to TNF-a stimulation (FIG. 17C, left panel). This co-precipitation was significantly attenuated by HGF in WT transfected cells. In contrast, HGF's action was substantially blunted in cells expressing S9A. Taken together, all these findings suggested that HGF modulates GSK3b's physical interaction with NFkB p65 through inhibitory phosphorylation of GSK3b at S9.

EXAMPLE 19

Figures 18A, 18B, 18C, 18D:
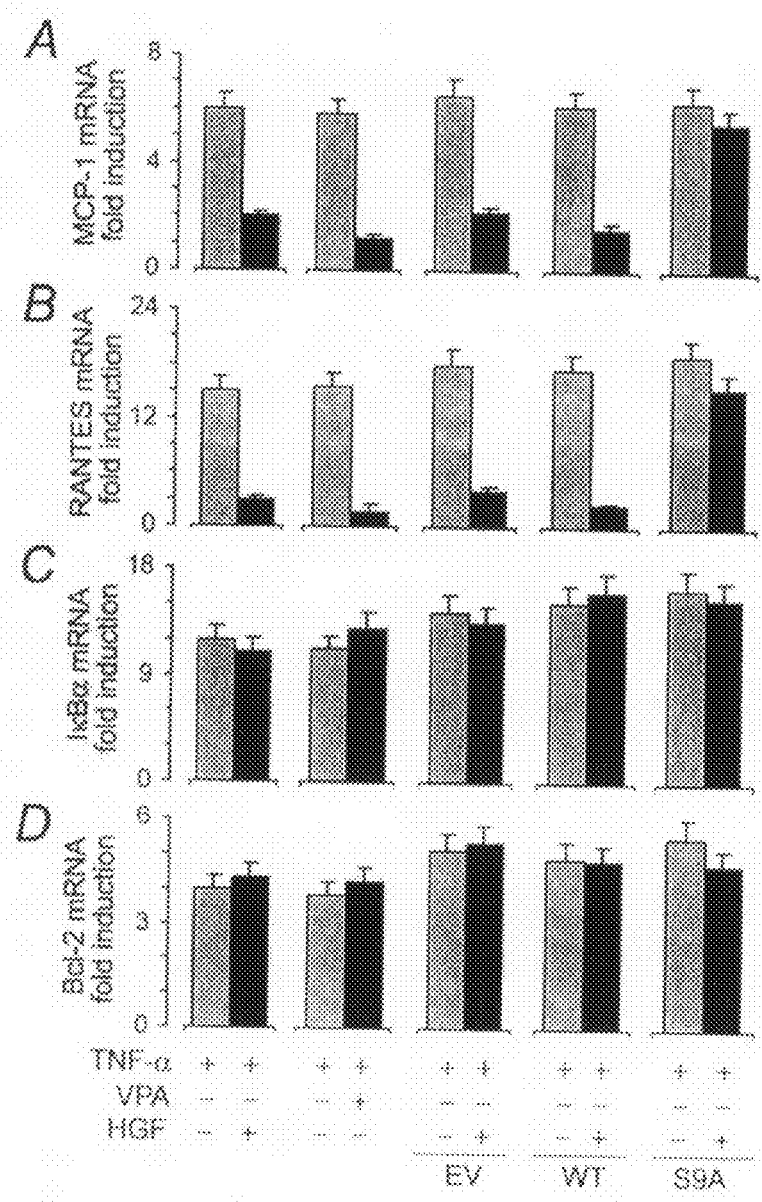
FIGS. 18A-18D show that HGF treatment selectively regulates TNF-a induced transcription of specific NFkB target genes. This effect is reminiscent of the action of the GSK3b inhibitor valproic acid and obliterated in cells expressing the mutant uninhibitable GSK3b. TNF-a stimulated HKC cells were treated with HGF or valproic acid for 12 h before mRNA extraction. In parallel, HKC cells, transfected with empty vector or vectors encoding the wild type GSK3b or the mutant uninhibitable GSK3b (S9A) in which the serine 9 position was replaced by alanine, were treated with or without HGF upon TNF-a stimulation for 12 h before mRNA extraction. Message expression of MCP-1 (A), RANTES (B), IkBa (C) or Bcl-2 (D) were profiled by real-time PCR.

GSK3b Inactivation Mediates HGF's Selective Suppression of the Expression of NFkB Dependent Proinflammatory Genes Recently, accruing evidence suggests that distinct p65 modification patterns, including serine phosphorylation at multiple newly identified positions (e.g. $Ser_{468}$), control the transcription of distinct subsets of NFkB target genes. Moreover, Steinbrecher et al lately found that GSK3b functions to specify gene specific, NFkB-dependent transcription. In our study, the aforementioned results indicated that HGF is able to modulate p65 phosphorylation at $Ser_{468}$ through inactivating GSK3b. Therefore; it is rational to speculate that HGF might distinctly regulate the transcription of subsets of NFkB target genes. To address this issue, NFkB was stimulated by TNF-a, a prototype NFkB activator, in the presence or absence of HGF in HKC cells. As shown in FIG. 18, mRNA expression of four NFkB target genes, including MCP-1, RANTES, IkBa and Bcl-2, was profiled by real time RT-PCR. HGF strikingly attenuated TNF-a induced mRNA expression of MCP-1 and RANTES, two proinflammatory chemoattractant cytokines. Similar suppressive effect by HGF was also observed on the induced mRNA expression of other proinflammatory genes like IL-8 (data not shown). In contrast, TNF-a induced mRNA expression of IkBa, an anti-inflammatory transcription factor, as well as Bcl-2, a pro-survival factor, was not remarkably affected by HGF concomitant treatment. Of note, consistent with HGF's inhibitory effect on GSK3b, VPA, the specific GSK3b inhibitor, mimicked the action of HGF on the expression of these genes. Similar studies were further carried out in cells transfected with WT or S9A as well as empty vector. The suppressive effect of HGF on TNF-a induced MCP-1 and RANTES expression was present in cells transfected with EV or WT but was obliterated in cells expressing S9A, implying that inhibitory phosphorylation of GSK3b at $S_{erg}$ is required for HGF suppression of RANTES and MCP-1 expression. Collectively, these findings suggest that HGF selectively inhibits the induced expression of a subset of NFkB target proinflammatory genes.

EXAMPLE 20

GSK3b Inactivation Correlates With HGF Receptor Activity and Loss of RelA/p65 Phoslphorylation at $Ser_{468}$ as Well as Pathologic Changes in Diseased Human Kidney Recent studies demonstrated that HGF is a potent anti-inflammatory cytokine that ameliorates acute and chronic inflammation and injury in multiple organs including the kidney. In addition, epidemiologic data revealed that HGF/c-Met signaling activity correlates with improved renal pathology in human kidney disease. To gain further insight into the pathophysiologic significance of the GSK3b mediated HGF regulation of NFkB activity, we next examined the expression of key components of the HGF/c-Met-GSK3b-NFkB signaling pathway in biopsy specimens of chronic allograft nephropathy (CAN). HGF functions in the kidney predominantly on the tubular epithelial cells, which abundantly express its cognate receptor, c-Met. Activation of HGF/c-Met signaling axis, as denoted by intense staining of phosphorylated c-Met, was found to correlate with intensified GSK3b inactivation and reduced RelA/p65 phosphorylation at $Ser_{468}$. In contrast, decreased GSK3b inactivation in parallel with magnified p65 phosphorylation at $Ser_{468}$ was observed in tubules with low HGF receptor activity. Of note, in concordance with the renoprotecive effect of HGF, activation of HGF/c-Met-GSK3b-NFkB p65 signaling pathway was found to inversely associate with the magnitude of renal injuries and pathologic changes in CAN according to Banff criteria. Thus, enhanced GSK3b inactivation, which was associated with elevated c-Met activity and loss of NFkB p65 phosphorylation at $Ser_{468}$, significantly correlated with low-grade or subsiding CAN; whereas, less GSK3b inactivation, which was associated with diminished c-Met activity and increased NFkB p65 phosphorylation at $Ser_{468}$, markedly correlated with high-grade or worsened CAN.

TABLE 1

Relationship between tubular expression of p-Met, p-GSK3β, and p-NFκB p65 in human kidneys with chronic allograft nephropathy.

|  | GSK3b (pS9) Low | GSK3b (pS9) High | P value |
|---|---|---|---|
| c-Met (pY1349) |  |  |  |
| Low | 8 | 2 |  |
| High | 1 | 9 |  |
|  |  |  | .005 |
| RelA/p65 (pS468) |  |  |  |
| Low | 1 | 7 |  |
| High | 9 | 3 |  |
|  |  |  | .02 |
| CAN grade (Banff) |  |  |  |
| I | 2 | 6 |  |
| II | 3 | 1 |  |
| III | 7 | 1 |  |
|  |  |  | .04 |

Figures 19A, 19B, 19C, 19D, 19E, 19F:
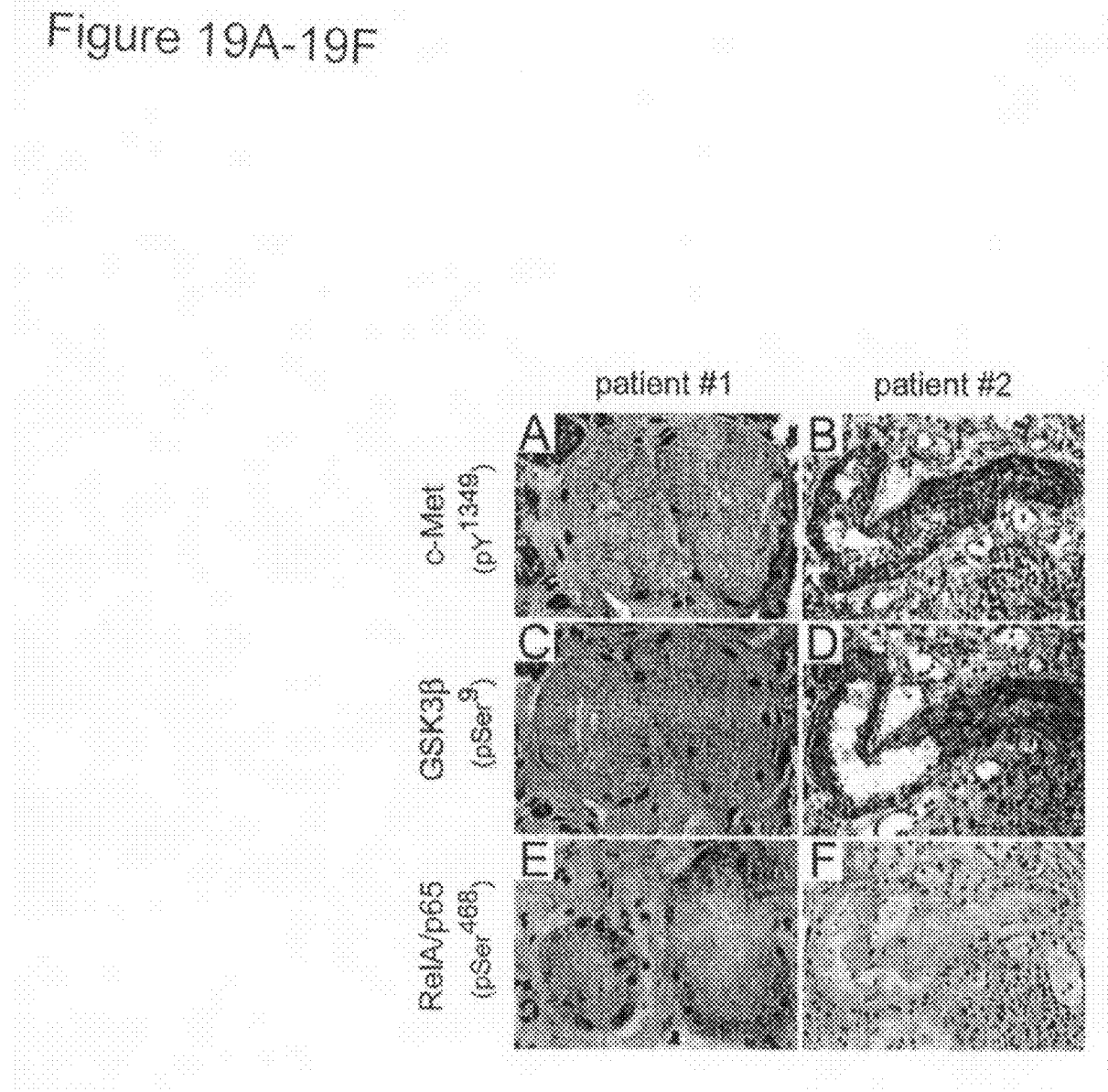
FIGS. 19A-19F show that the magnitudes of HGF receptor c-Met activation correlate with the extent of GSK3b inactivation and loss of NFKB phosphorylation at Ser468 in human diseased kidney. Representative immunohistochemistry micrographs depict that renal biopsy specimens from 2 patients with chronic allograft nephropathy express phosphorylated c-Met (Y1349) (A, B), phosphorylated GSk3b (S9) (C, D) and phosphorylated RelA/p65 (S468) (E, F) in tubules with different intensity.

The expression patterns of the 3 molecules in human CAN biopsy specimens were determined by immunohistochemistry staining as shown in FIG. 19. The correlation between GSK3b (pS9) and c-Met (pY1349), RelA/p65 and CAN grade were analyzed by Fisher's exact probability test.

EXAMPLE 21

Materials and Methods

Cell Culture

Human proximal TEC (HKC-8) (courtesy of Dr. L. Racusen of John Hopkins University, Baltimore, Md.) were maintained in Dulbecco's modified Eagle's medium (DMEM)/F12 supplemented with 5% fetal bovine serum (FBS). Cells were plated at approximately 70% confluence in the media containing 5% FBS for 24 h and then underwent serum starvation for another 24 h. Human recombinant HGF and human recombinant TNF-α (R&D systems, Minneapolis, Minn.) were added to the culture with fresh serum-free medium at a final concentration of 20 ng/ml and 2 ng/ml respectively, or otherwise as indicated. Cell viability was assessed by Trypan blue exclusion. At different time points, cells and conditioned media were harvested for further investigation.

Chromatin Immunoprecipitation Assay (ChIP)

The in situ interaction between NFκB and its target genes in HKC cells was examined by ChIP assay (35) using a commercially available kit (Upstate Biotechnology, Charlottesville, Va.) according to manufacturer's instructions. Briefly, HKC cells were fixed and crosslinked with 4% formaldehyde. After collection of cell pellets and sonication, aliquots of the samples were set aside as input fraction and the rest subjected to immunoprecipitation using an anti-NFκB p65 antibody or preimmune IgG and Protein A agarose used to pull down the immune complexes. After elution, precipitated chromatin as well as the input fraction was heated at 65° C. to reverse crosslinks and the DNA extracted with Qiagen PCR purification kit (Qiagen, Valencia, Calif.). DNA sequences spanning the κB responsive elements in the promoter region were amplified by PCR using specific primers (MCP-1, forward 5'-acccttctgtgcctcagttg-3' (SEQ ID NO: 1), reverse 5'-ctgcagaagaaatgccagtg-3'(SEQ ID NO: 2), Genbank accession number Y18933; RANTES, forward 5'-gactcgaatttccggagcta-3' (SEQ ID NO: 3), reverse 5'-ccctttataggcgcagttga-3' (SEQ ID NO: 4), Genbank accession number S64885) for a number of cycles in the exponential phase as estimated in pilot experiments. DNA samples extracted from input fractions were amplified in parallel for normalization. PCR products resolved in ~1.5 to 2% agarose gels were photographed under ultraviolet light.

Western Immunoblot Analysis

After different treatments, HKC cells were washed with PBS and lysed with RIPA buffer supplemented with protease inhibitors [1% Nonidet P-40, 0.1% SDS, 100 ug/ml phenylmethysulfonyl fluoride (PMSF), 0.5% sodium deoxycholate, 1mM sodium orthovanadate, 2 ug/ml aprotin, 2 ug/ml leupeptin, 5mM EDTA in PBS]. Protein concentration was determined by using a bicinchoninic acid protein assay kit (Sigma). All samples with equal amounts of total protein (50 ug/ml) were fractionated by 7.5~15% SDS-polyacrylamide gels under reducing condition and analyzed by western immunoblot as described previously (30). The antibodies against p-GSK3b, p-NFkB p65, p-IkBa were purchased from Cell Signaling Technology (Beverly, Mass.) and those for GSK3b, hemagglutin were from Santa Cruz Biotechnology (Santa Cruz, Calif.).

Transient Transfection

The expression vectors encoding the HA tagged wild type (WT-GSK3b-HA/pcDNA3) and uninhibitable mutant (S9A-GSK3b-HA/pcDNA3) GSK3b were respectively provided by Dr. Jim Woodgett (University of Toronto, Toronto, Ontario, Canada) and Dr. Gail V. W. Johnson (University of Alabama at Birmingham, Birmingham, Ala.). Transient transfection of HKC cells was carried out by using the Lipofectamine 2000 according to the instructions specified by the manufacturer (Invitrogen, Carlsbad, Calif.). After transfection with equal amounts of expression plasmid or empty vector pcDNA3 (Invitrogen), HKC cells were subjected to different treatment as indicated.

Immunoprecipitation

Immunoprecipitation was carried out by using an established method as described previously. Briefly, cells were washed with ice cold PBS and then lysed with RIPA buffer.

After preclearing with normal IgG, cell lysates with equal amount of total protein (0.5 mg of protein) were incubated overnight at 4° C. with 4 µg specific agarose-conjugated antibodies. The precipitated complexes were collected, washed, and separated on SDS-polyacrylamide gels and blotted with various antibodies as indicated.

Fluorescent Immunocytochemistry

Indirect immunofluorescence staining was performed using an established procedure. Briefly, cells cultured on coverslips were washed twice with cold PBS and fixed with cold methanol/acetone (1:1) for 10 minutes at −20° C. Following three extensive washings with PBS containing 0.5% BSA, the cells were blocked with 20% normal donkey serum in PBS buffer for 30 minutes at room temperature and then incubated with the specific primary antibodies. Finally cells were double stained with DAPI (4',6-diamidino-2-phenylindole) to visualize the nuclei. Stained cells were mounted with Vectashield mounting medium (Vector Laboratories, Burlingame, Calif., USA). Results were interpreted using a fluorescence microscope.

Immunohistochemistry

Human tissues were obtained from discarded transplant kidney biopsy specimens obtained from patients with pathology-proven chronic allograft nephropathy. Formalin-fixed tissues were embedded in paraffin and prepared in 3-µm-thick sections. Immunohistochemical staining for phosphorylated c-Met, GSK3b and RelA/p65 was carried out as described previously by using a Vectastain ABC kit (Vector Laboratories, Burlingame, Calif.). As a negative control, the primary antibody was replaced by nonimmune serum from the same species; no staining occurred. The extent of staining was graded on a scale based on low or high.

RNA Extraction, Reverse Transcription and Real Time Polymerase Chain Reaction (PCR)

Total RNA was extracted from approximately $1 \times 10_6$ cultured HKC cells using TRIzol solution (Invitrogen, Carlsbad, Calif.) according to the instructions specified by the manufacturer. RNA was then diluted to 3µg/µl in RNase free distilled water. The first strand cDNA was prepared using 3 µg RNA, Superscript RT reverse transcriptase (Invitrogen) and oligo (dT) primer according to the manufacture's instruction. Quantitative real time PCR was carried out on a Stratagene Mx4000® multiplex quantitative PCR system (Stratagene, La Jolla, Calif.) using primers specific for human MCP-1, RANTES, IkBa, Bcl-2 and GAPDH. All reactions were performed in triplicate with Brilliant® SYBR® Green QPCR Master Mix (Stratagene). Fluorescence values of SYBR Green I dye, representing the amount of product amplified at that point in the reaction, were recorded in real time at both the annealing step and the extension step of each cycle. The Ct value, defined as the point at which the fluorescence signal was statistically significant above background, was calculated for each amplicon in each experimental sample using Stratagene Mx4000 software. This value was then used to determine the relative amount of amplification in each sample by interpolating from the standard curve. Transcript level of each specific gene was normalized to GAPDH amplification.

Statistics

For immunoblot analysis, bands were scanned and the integrated pixel density was determined using a densitometer and the NIH image analysis program. All data are expressed as mean±SD. Statistical analysis of the data from multiple groups was performed by ANOVA followed by Student-Newman-Kuels tests. Data from two groups were compared by Students'-t test. Linear regression analysis was applied to examine possible relationships between two parameters. $P<0.05$ was considered significant.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Remuzzi, G. & Bertani, T. Pathophysiology of progressive nephropathies. N Engl J Med 339, 1448-56 (1998).
2. Main, I. W., Nikolic-Paterson, D. J. & Atkins, R. C. T cells and macrophages and their role in renal injury. Semin Nephrol 12, 395-407 (1992).
3. Eddy, A. A. Molecular basis of renal fibrosis. Pediatr Nephrol 15, 290-301 (2000).
4. Junaid, A. & Amara, F. M. Osteopontin: correlation with interstitial fibrosis in human diabetic kidney and P13-kinase-mediated enhancement of expression by glucose in human proximal tubular epithelial cells. Histopathology 44, 136-46 (2004).
5. Nangaku, M. Mechanisms of tubulointerstitial injury in the kidney: final common pathways to end-stage renal failure. Intern Med 43, 9-17 (2004).
6. Eddy, A. A. Proteinuria and interstitial injury. Nephrol Dial Transplant 19, 277-81 (2004).
7. Lloberas, N. et al. Postischemic renal oxidative stress induces inflammatory response through PAF and oxidized phospholipids. Prevention by antioxidant treatment. Faseb J 16, 908-10 (2002).
8. Daha, M. & vanKooten, C. Is the proximal tubular cell a proinflammatory cell? Nephron Exp Nephrol 15, 41-43 (2000).
9. Smith, C. W. Leukocyte-endothelial cell interactions. Semin Hematol 30, 45-53; discussion 54-5 (1993).
10. Gong, R. et al. Hepatocyte growth factor ameliorates renal interstitial inflammation in rat remnant kidney by modulating tubular expression of macrophage chemoattractant protein-1 and RANTES. J Am Soc Nephrol 15, 2868-81 (2004).
11. Gong, R., Rifai, A. & Dworkin, L. D. Activation of PI3K-Akt-GSK3beta pathway mediates hepatocyte growth factor inhibition of RANTES expression in renal tubular epithelial cells. Biochem Biophys Res Commun 330, 27-33 (2005).
12. Gong, R., Rifai, A. & Dworkin, L. D. Hepatocyte growth factor (HGF) suppresses acute renal inflammation by inhibition of endothelial E-selectin. J Am Soc Nephrol 16, 415A (2005).
13. To, C. T. & Tsao, M. S. The roles of hepatocyte growth factor/scatter factor and met receptor in human cancers (Review). Oncol Rep 5, 1013-24 (1998).
14. Dugo, L. et al. GSK-3beta inhibitors attenuate the organ injury/dysfunction caused by endotoxemia in the rat. Crit Care Med 33, 1903-12 (2005).
15. Fink, M. What do insulin, estrogen, valproic acid, and TDZD-8 have in common? Crit Care Med 33, 2115-7 (2005).
16. Martin, M., Rehani, K., Jope, R. S. & Michalek, S. M. Toll-like receptor-mediated cytokine production is differentially regulated by glycogen synthase kinase 3. Nat Immunol 6, 777-84 (2005).
17. Woodgett, J. R. & Ohashi, P. S. GSK3: an in-Toll-erant protein kinase? Nat Immunol 6, 751-2 (2005).

18. Guijarro, C. & Egido, J. Transcription factor-kappa B (NF-kappa B) and renal disease. Kidney Int 59, 415-24 (2001).

19. Martinez, A., Castro, A., Dorronsoro, I. & Alonso, M. Glycogen synthase kinase 3 (GSK-3) inhibitors as new promising drugs for diabetes, neurodegeneration, cancer, and inflammation. Med Res Rev 22, 373-84 (2002).

20. Nathan, C. Points of control in inflammation. Nature 420, 846-52 (2002).

21. Hershkoviz, R., Alon, R., Gilat, D. & Lider, O. Activated T lymphocytes and macrophages secrete fibronectin which strongly supports cell adhesion. Cell Immunol 141, 352-61 (1992).

22. Vaage, J. & Lindblad, W. J. Production of collagen type I by mouse peritoneal macrophages. J Leukoc Biol 48, 274-80 (1990).

23. Ricardo, S. D. & Diamond, J. R. The role of macrophages and reactive oxygen species in experimental hydronephrosis. Semin Nephrol 18, 612-21 (1998).

24. Austen, K. F. The role of arachidonic acid metabolites in local and systemic inflammatory processes. Drugs 33 Suppl 1, 10-7 (1987).

25. Nathan, C. F. Secretory products of macrophages. J Clin Invest 79, 319-26 (1987).

26. Lan, H. Y. Tubular epithelial-myofibroblast transdifferentiation mechanisms in proximal tubule cells. Curr Opin Nephrol Hypertens 12, 25-9 (2003).

27. Bohle, A. et al. The long-term prognosis of the primary glomerulonephritides. A morphological and clinical analysis of 1747 cases. Pathol Res Pract 188, 908-24 (1992).

28. Rodriguez-Iturbe, B., Pons, H., Herrera-Acosta, J. & Johnson, R. J. Role of immunocompetent cells in nonimmune renal diseases. Kidney Int 59, 1626-40 (2001).

29. Fujihara, C. K., Malheiros, D. M., Zatz, R. & Noronha, I. D. Mycophenolate mofetil attenuates renal injury in the rat remnant kidney. Kidney Int 54, 1510-9 (1998).

30. Utimura, R. et al. Mycophenolate mofetil prevents the development of glomerular injury in experimental diabetes. Kidney Int 63, 209-16 (2003).

31. Wang, Y., Rangan, G. K., Tay, Y. C. & Harris, D. C. Induction of monocyte chemoattractant protein-1 by albumin is mediated by nuclear factor kappaB in proximal tubule cells. J Am Soc Nephrol 10, 1204-13 (1999).

32. Gomez-Garre, D. et al. Activation of NF-kappaB in tubular epithelial cells of rats with intense proteinuria: role of angiotensin II and endothelin-1. Hypertension 37, 1171-8 (2001).

33. O'Riordan, E. et al. Endothelial cell dysfunction: the syndrome in making. Kidney Int 67, 1654-8 (2005).

34. Weber, C. & Erl, W. Modulation of vascular cell activation, function, and apoptosis: role of antioxidants and nuclear factor-kappa B. Curr Top Cell Regul 36, 217-35 (2000).

35. de Haij, S., Daha, M. R. & van Kooten, C. Mechanism of steroid action in renal epithelial cells. Kidney Int 65, 1577-88 (2004).

36. Cao, Z. & Cooper, M. E. Role of angiotensin II in tubulointerstitial injury. Semin Nephrol 21, 554-62 (2001).

37. Holschermann, H. et al. Statins prevent NF-kappaB transactivation independently of the IKK-pathway in human endothelial cells. Atherosclerosis (2005).

38. Haefner, B. A model for NF-kappa B regulation by GSK-3 beta. Drug Discov Today 8, 1062-3 (2003).

39. Demarchi, F., Bertoli, C., Sandy, P. & Schneider, C. Glycogen synthase kinase-3 beta regulates NF-kappa B1/p105 stability. J Biol Chem 278, 39583-90 (2003).

40. Deng, J. et al. Crossregulation of NF-kappaB by the APC/GSK-3betalbeta-catenin pathway. Mol Carcinog 39, 139-46 (2004).

41. Buss, H. et al. Phosphorylation of serine 468 by GSK-3beta negatively regulates basal p65 NF-kappaB activity. J Biol Chem 279, 49571-4 (2004).

42. Steinbrecher, K. A., Wilson, W., 3rd, Cogswell, P. C. & Baldwin, A. S. Glycogen synthase kinase 3beta functions to specify gene-specific, NF-kappaB-dependent transcription. Mol Cell Biol 25, 8444-55 (2005).

43. Jope, R. S. & Johnson, G. V. The glamour and gloom of glycogen synthase kinase-3. Trends Biochem Sci 29, 95-102 (2004).

44. Cohen, P. & Frame, S. The renaissance of GSK3. Nat Rev Mol Cell Biol 2, 769-76 (2001).

45. Ali, A., Hoeflich, K. P. & Woodgett, J. R. Glycogen synthase kinase-3: properties, functions, and regulation. Chem Rev 101, 2527-40 (2001).

46. Hoeflich, K. P. et al. Requirement for glycogen synthase kinase-3beta in cell survival and NF-kappaB activation. Nature 406, 86-90 (2000).

47. Schwabe, R. F. & Brenner, D. A. Role of glycogen synthase kinase-3 in TNF-alpha-induced NF-kappaB activation and apoptosis in hepatocytes. Am J Physiol Gastrointest Liver Physiol 283, G204-11 (2002).

48. Nikoulina, S. E. et al. Potential role of glycogen synthase kinase-3 in skeletal muscle insulin resistance of type 2 diabetes. Diabetes 49, 263-71 (2000).

49. Doble, B. W. & Woodgett, J. R. GSK-3: tricks of the trade for a multi-tasking kinase. J Cell Sci 116, 1175-86 (2003).

50. Dugo, L. et al. Glycogen synthase kinase-3beta inhibitors protect against the organ injury and dysfunction caused by hemorrhage and resuscitation. Shock 25, 485-91 (2006).

51. Whittle, B. J. et al. Reduction of experimental colitis in the rat by inhibitors of glycogen synthase kinase-3beta. Br J Pharmacol 147, 575-82 (2006).

52. O'Riordan, J. W., Kelleher, D., Williams, Y. & Bloomfield, F. J. Effect of lithium therapy on inflammatory response. Inflammation 10, 49-57 (1986).

53. Aleksandrov, P. N. & Speranskaia, T. V. [Dynamics of carrageenin-induced inflammation after use of lithium oxybutyrate]. Biull Eksp Biol Med 106, 233-5 (1988).

54. Jankovic, B. D., Popeskovic, L. & Isakovic, K. Cation-induced immunosuppression: the effect of lithium or Arthus reactivity, delayed hypersensitivity and antibody production in the rat. Adv Exp Med Biol 114, 339-44 (1979).

55. Levine, S. & Saltzman, A. Inhibition of experimental allergic encephalomyelitis by lithium chloride: specific effect or nonspecific stress? Immunopharmnacology 22, 207-13 (1991).

56. Heemann, U. et al. Lipopolysaccharide pretreatment protects from renal ischemia/reperfusion injury: possible connection to an interleukin-6-dependent pathway. Am J Pathol 156, 287-93 (2000).

57. Timmer, R. T. & Sands, J. M. Lithium intoxication. J Am Soc Nephrol 10, 666-74 (1999).

58. Gitlin, M. Lithium and the kidney: an updated review. Drug Saf 20, 231-43 (1999).

59. Cohen, P. & Goedert, M. GSK3 inhibitors: development and therapeutic potential. Nat Rev Drug Discov 3, 479-87 (2004).

60. Smith, G. C., Balfe, J. W. & Kooh, S. W. Anticonvulsants as a cause of Fanconi syndrome. Nephrol Dial Transplant 10, 543-5 (1995).

61. Ziolkowska, A. et al. Valproic acid prevents skin disease and attenuates severity of kidney disease in Mrl-lpr/lpr lupus-like mouse model. Am College of Rheumatol 1686 (2006).

62. Lin, C. L. et al. Wnt/beta-Catenin Signaling Modulates Survival of High Glucose-Stressed Mesangial Cells. J Am Soc Nephrol 17, 2812-20 (2006).

63. Martinez, A., Alonso, M., Castro, A., Perez, C. & Moreno, F. J. First non-ATP competitive glycogen synthase kinase 3 beta (GSK-3beta) inhibitors: thiadiazolidinones (TDZD) as potential drugs for the treatment of Alzheimer's disease. J Med Chem 45, 1292-9 (2002).

64. Cho, J. H. & Johnson, G. V. Primed phosphorylation of tau at Thr231 by glycogen synthase kinase 3beta (GSK3beta) plays a critical role in regulating tau's ability to bind and stabilize microtubules. J Neurochem 88, 349-58 (2004).

65. Taal, M. W. et al. Proinflammatory gene expression and macrophage recruitment in the rat remnant kidney. Kidney Int 58, 1664-76 (2000).

66. Navarro, J. F. et al. Tumor necrosis factor-alpha gene expression in diabetic nephropathy: relationship with urinary albumin excretion and effect of angiotensin-converting enzyme inhibition. Kidney Int Suppl, S98-102 (2005).

67. Dworkin, L. D. et al. Hepatocyte growth factor ameliorates progression of interstitial fibrosis in rats with established renal injury. Kidney Int 65, 409-19 (2004).

68. Lax, D. S., Benstein, J. A., Tolbert, E. & Dworkin, L. D. Effects of salt restriction on renal growth and glomerular injury in rats with remnant kidneys. Kidney Int 41, 1527-34 (1992).

69. Terzi, F. et al. Subtotal but not unilateral nephrectomy induces hyperplasia and protooncogene expression. Am J Physiol 268, F793-801 (1995).

What is claimed is:

1. A method of detecting whether a subject has renal injury or disease comprising:
   (a) obtaining a sample of a fluid or bodily tissue from said subject;
   (b) assessing the level of GSK3b, Glycogen synthase kinase-3β
wherein an increase in said level in said subject compared to a normal control level is indicative that the subject has renal injury or disease.

2. The method of claim 1, wherein said subject is a human.

3. The method of claim 1, wherein an increase of at least 10% compared to said normal control indicates that said subject comprises a renal injury or disease.

4. The method of claim 1, wherein an increase of at least 50% compared to said normal control indicates that said subject comprises a renal injury or disease.

5. The method of claim 1, wherein an increase of at least 2-fold compared to said normal control indicates that said subject comprises a renal injury or disease.

6. The method of claim 1, wherein said subject comprises a creatinine level or a urinary protein level in a normal range.

7. The method of claim 1, wherein said bodily fluid is selected from the group consisting of blood, serum, plasma, urine, saliva, cerebral spinal fluid, joint fluid, fluid from the pleural space, and peritoneal fluid.

8. The method of claim 1, wherein said bodily tissue is a tissue biopsy.

9. The method of claim 1, wherein the presence of GSK3b is a detectable level of GSK3b.

10. The method of claim 1, wherein said bodily fluid or bodily tissue is contacted with a detectable composition that binds to GSK3b.

11. The method of claim 10, wherein said composition is an antibody.

12. The method of claim 11, wherein said antibody and said bodily fluid or bodily tissue are contacted under conditions sufficient to form an immune complex and detecting the immune complex to determine a GSK level.

13. The method of claim 11, wherein said antibody or antigen binding fragment thereof is selected from the group consisting of a polyclonal antibody, a monoclonal antibody or antibody fragment, a diabody, a chimerized or chimeric antibody or antibody fragment, a humanized antibody or antibody fragment, a deimmunized human antibody or antibody fragment, a fully human antibody or antibody fragment, a single chain antibody, an Fv, an Fd, an Fab, an Fab', and an F(ab')2.

14. The method of claim 13, wherein said antibody or antigen binding fragment thereof is a monoclonal antibody.

15. The method of claim 14, wherein the antibody or antigen binding fragment thereof is covalently linked to an additional functional moiety.

16. The method of claim 15, wherein the additional functional moiety is a detectable label.

17. The method of claim 16, wherein the detectable label is selected from a fluorescent or chromogenic label.

18. The method of claim 16, wherein said detectable label is selected from horseradish peroxidase or alkaline phosphatase.

19. A method of developing a prognosis for a patient suffering from renal injury or disease comprising:
   (a) obtaining a sample from said subject;
   (b) assessing the level of GSK3b, Glycogen synthase kinase-3β in said sample,
wherein a high level of GSK3b is indicative of a poor prognosis.

20. The method of claim 19, wherein said subject is a human.

21. The method of claim 19, wherein an increase in said level over time indicates an adverse prognosis or an increase in severity of disease.

22. The method of claim 19, wherein said subject comprises a creatinine level or a urinary protein level in a normal range.

23. The method of claim 19, wherein said bodily fluid is selected from the group consisting of blood, serum, plasma, urine, saliva, cerebral spinal fluid, joint fluid, fluid from the pleural space, and peritoneal fluid.

24. The method of claim 19, wherein said bodily tissue is a tissue biopsy.

25. The method of claim 19, wherein the presence of GSK3b is a detectable level of GSK3b.

26. The method of claim 19, wherein said bodily fluid or bodily tissue is contacted with a detectable composition that binds to GSK3b.

27. The method of claim 26, wherein said composition is an antibody.

28. The method of claim 27, wherein said antibody and said bodily fluid or bodily tissue are contacted under conditions sufficient to form an immune complex and detecting the immune complex to determine a GSK level.

29. The method of claim 27, wherein said antibody or antigen binding fragment thereof is selected from the group consisting of a polyclonal antibody, a monoclonal antibody or antibody fragment, a diabody, a chimerized or chimeric antibody or antibody fragment, a humanized antibody or antibody fragment, a deimmunized human antibody or antibody fragment, a fully human antibody or antibody fragment, a single chain antibody, an Fv, an Fd, an Fab, an Fab', and an F(ab')2.

30. The method of claim 29, wherein said antibody or antigen binding fragment thereof is a monoclonal antibody.

31. The method of claim 30, wherein the antibody or antigen binding fragment thereof is covalently linked to an additional functional moiety.

32. The method of claim 31, wherein the additional functional moiety is a detectable label.

33. The method of claim 32, wherein the detectable label is selected from a fluorescent or chromogenic label.

34. The method of claim 32, wherein said detectable label is selected from horseradish peroxidase or alkaline phosphatase.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acccttctgt gcctcagttg                                                       20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgcagaaga aatgccagtg                                                       20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gactcgaatt tccggagcta                                                       20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccctttatag ggccagttga                                                       20

<210> SEQ ID NO 5
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Leu Arg Arg Pro Ser Asp Arg Glu Leu Ser Glu Pro Met Glu Phe
1               5                   10                  15

Gln Tyr Leu Pro
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Thr Asp Leu Ala Ser Val Asp Asn Ser Glu Phe Gln Gln Leu Leu
1               5                   10                  15

Asn Gln Gly Ile
            20
```